United States Patent [19]
Potempa

[11] Patent Number: 5,939,529
[45] Date of Patent: Aug. 17, 1999

[54] METHODS AND KITS FOR STIMULATING PRODUCTION OF MEGAKARYOCYTES AND THROMBOCYTES

[75] Inventor: Lawrence A. Potempa, Deerfield, Ill.

[73] Assignee: Immtech International Inc., Evanston, Ill.

[21] Appl. No.: 08/548,974

[22] Filed: Oct. 27, 1995

Related U.S. Application Data

[63] Continuation-in-part of application No. 08/202,033, Feb. 23, 1994, Pat. No. 5,547,931.
[51] Int. Cl.$^6$ .......................... A61K 35/14; A61K 38/16; C12N 15/00
[52] U.S. Cl. .......................... 530/380; 530/402; 530/830; 514/2; 514/8; 514/21; 435/69.1; 435/69.6; 435/172.1
[58] Field of Search ...................... 514/2, 8, 21; 530/380, 530/402, 830; 435/69.1, 69.6, 172.1, 810, 975, 69.7; 436/18, 64

[56] References Cited

U.S. PATENT DOCUMENTS

| | | | |
|---|---|---|---|
| 4,946,437 | 8/1990 | Sredni et al. | 604/49 |
| 5,032,396 | 7/1991 | Williams | 424/85.2 |
| 5,126,325 | 6/1992 | Kishimoto et al. | 514/12 |
| 5,128,245 | 7/1992 | Greenberg et al. | 435/29 |
| 5,221,628 | 6/1993 | Anderson et al. | 436/507 |
| 5,250,732 | 10/1993 | Kogan et al. | 564/221 |
| 5,260,417 | 11/1993 | Grant et al. | 530/351 |
| 5,272,258 | 12/1993 | Siegel et al. | 530/388.25 |
| 5,283,238 | 2/1994 | Potempa et al. | 514/12 |
| 5,290,762 | 3/1994 | Lezdey et al. | 514/8 |

FOREIGN PATENT DOCUMENTS

| | | |
|---|---|---|
| 89/09628 | 10/1989 | WIPO . |
| 93/10799 | 6/1993 | WIPO . |
| 93/10800 | 6/1993 | WIPO . |
| 93/21944 | 11/1993 | WIPO . |

OTHER PUBLICATIONS

Asano et al., *Blood*, 75:1602 (1990).
Beaucage and Caruthers, *Tetrahedron Letters*, 22:1859 (1981).
*Bio/Technology*, pp. 636–639 (Jul. 1984).
Birnboim et al., *Nucleic Acids Res.*, 7:1513–1523 (1979).
Botstein et al., *Science*, 229:1193 (1985).
Brake et al., *Proc. Natl. Acad. Sci. USA*, 81:4642–46 (1984).
Bravo et al., *J. Rheumatology*, 8:291–294 (1981).
Bray et al., *Clin. Immunol. Newsletter*, 8:137–140 (1987).
Burstein et al., *J. Cellular Phys.*, 122:159 (1985).
Carrington et al., *Blood*, 77:34 (1991).
Carter et al., *Radiation Research*, 132:74–81 (1992).
*Chemical Modifications of Proteins*, G.E. Means and R.E. Feeney, Holden–Day, Inc. San Francisco, CA (1971).
*Chemistry of Protein Conjugation and Cross–linking*, S.S. Wong, CRC Press Boca Raton, FL (1991).
Chesebro and Metzger, *Biochemistry*, 11:766 (1972).
Chu et al., *Proc. Amer. Acad. Cancer Res.*, 28:344a (1987).
Chu et al., *Proc. Amer. Acad. Cancer Res.*, 29:371a (1988).
Chudwin et al., *J. Allergy Clin. Immunol.*, 77:216a (1986).
*Current Protocols In Molecular Biology*, Chapter 8, (Ansubel ed. 1987).
de Beer et al., *J. Immunol. Meth.*, 50:17–31 (1982).
Denney et al., *Amplifications*, 4:25–26 (1990).
Dixon et al., *Scand. J. Rheumatology*, 13:39–44 (1984).
Egenhofer et al., *Hepatology*, 18:1216 (1993).
Fiedel et al., *Clin. Exp. Immunol.*, 50:215–22 (1982).
Fiedel et al., *Immunology*, 45:439–447 (1982).
Fiedel et al., *J. Immunol.*, 131:1416 (1983).
Fiedel, *Blood*, 65:264–69 (1985).
Fiedel, *Fed. Proc.*, 44:1190a (1985).
Harrison's *Principles of Internal Medicine*, 9th Ed., McGraw–Hill, New York, 1980.
Hoffman et al., *Yale J. Biol. Med.*, 63:411–418 (1990).
Horton et al., *BioTechniques*, 8:528–535 (1990).
Hu et al., *Biochem.*, 25:7834–39 (1986).
Hu et al., *J. Biol. Chem.*, 263:1500–1504 (1988).
Ishibashi et al., *Blood*, 74:1241 (1989).
Ito et al., *Nucleic Acids Res.*, 10:1755–69 (1982).
Kilpatrick et al., *Immunol. Res.*, 10:43–53 (1991).
Kresl et al., *FASEB J.*, 5:633a (1991).
Kunkel et al., *Methods Enzymol.*, 154:367–82 (1987).
Lei et al., *J. Biol. Chem.*, 260:13377–13383 (1985).
Maniatis et al., *Molecular Cloning: A Laboratory Manual* (1982).
Mantzouranis et al., *Ped. Res.*, 18:260a (1984).
Marchasin et al., *California Medicine*, 101:95–100 (1964).
Matteucci and Caruthers, *Tetrahedron Letters*, 21:719 (1980).
Matteucci and Caruthers, *J. Amer. Chem. Soc.*, 103:3185 (1981).
Metcalf, D., *In Hematopoietic Colony Stimulating Factors*, Elsevier/North Holland, Amersterdam (1984).
Miller, *Experiments in Molecular Genetics*, (1972).
Miyazawa et al., *J. Immunol.*, 141:570–74 (1988).
Mizoguchi et al., *Exp. Hematol.*, 7:346 (1979).
Moore et al., *Blood*, 78:1 (1991).
Murphy, *Hematol. Oncol. Clin. North Am.*, 3:465–478 (1989).

(List continued on next page.)

*Primary Examiner*—Ponnathapura Achutamurthy
*Assistant Examiner*—P. Ponnaluri
*Attorney, Agent, or Firm*—Sheridan Ross P.C.

[57] ABSTRACT

The invention provides methods for stimulating thrombocytopoiesis in a mammal comprising administering to the mammal an effective amount of modified C-reactive protein ("mCRP") or mutant protein expressing neo-CRP antigenicity. Methods for treating thrombocytopenia, and for promoting megakaryocyte growth and maturation in vitro are also provided. Kits and articles of manufacture are further provided which include mCRP or mutant protein expressing neo-CRP antigenicity.

3 Claims, 31 Drawing Sheets

OTHER PUBLICATIONS

Osmand et al., *Proc. Natl. Acad. Sciences, U.S.A.*, 74:739–743 (1977).
Pepys et al., *Advances in Immunology*, 34:141–212 (1983).
Podja et al., *Exp. Hematol.*, 18:1034 (1990).
Potempa et al., *Fed. Proc.*, 44:1190a (1985).
Potempa et al., *Proc. Amer. Acad. Cancer Res.*, 28:344a (1987).
Potempa et al., *Protides Biol. Fluids*, 34:287–290 (1987).
Potempa et al., *FASEB J.*, 2:731a (1988).
Potempa et al., *Inflammation*, 12:391–405 (1988).
Potempa et al., *Mol. Immunol.*, 20:1165–75 (1983).
Potempa et al., *Mol. Immunol.*, 24:531–541 (1987).
Rees et al., *Fed. Proc.*, 45:263a (1986).
Rosenberg et al., *Gene*, 56:125–135 (1987).
Saiki et al., *Science*, 239:487–491 (1988).
Samols et al., *Prot. Biol. Fluids*, 34:263–66 (1986).
Samols et al., *Biochem. J.*, 227:759–65 (1985).
Sanger et al., *J. Mol. Biol.*, 94:441–448 (1975).
Smith & Gillam, *Genetic Engineering Principles And Methods*, 3:1–32 (1981).
Sonoda et al., *PNAS USA*, 85:4360 (1988).
Studier et al., *J. Mol. Biol.*, 189:113–130 (1986).
Tatsumi et al., *Clin. Chim. Acta*, 172:85 (1988).
Teramura et al., *Blood*, 79:327 (1992).
The Platelet, International Academy of Pathology Monograph, published by Williams & Wilkins Company, 1971.
Thompson et al., *Blood*, 72:1 (1988).
Tillett and Francis, *J. Exp. Med.*, 52:561–71 (1930).
Tucci et al., *J. Immunol.*, 131:2416–19 (1983).
Vigo, *J. Biol. Chem.*, 260:3418 (1985).
Volanakis et al., *J. Immunol.*, 113:9–17 (1974).
Walker et al., *J. Clin. Path.*, 37:1022–1026 (1984).
Wang et al., *J. Biol. Chem.*, 257:13610–13615 (1982).
Whitehead et al., *Biochem. J.*, 266:283–290 (1990).
Williams, *Immunol. Ser.*, 49:215–229 (1990).
Woo et al., *J. Biol. Chem.*, 260:13384–88 (1985).
Yanisch–Perron et al., *Gene*, 33:103–119 (1985).
Ying et al., *Mol. Immunol.*, 29:677–687 (1992).
Ying et al., *J. Immunol.*, 143:221–28 (1989).
Yonemura et al., *Exp. Hematol.*, 20:1011 (1992).
Zeller et al., *Fed. Proc.*, 46:1033a (1987).
Zhang, *J. Immunol.*, 138:575 (1987).
Zoller & Smith, *Nucleic Acids Res.*, 10:6487–6500 (1982).
Zoller et al., *Methods Enzymol.*, 100:468–500 (1983).
Zoller & Smith, *DNA*, 3:479–88 (1984).
de Sauvage et al., *Nature*, 369:533–538 (1994).
"Discovery of key blood protein raises hope for cancer treatment," *Chicago Tribune*, Thursday, Jun. 16, 1994, Section 1, p. 3.
Kaushansky et al., *Nature*, 369:568–571 (1994).
King et al., "Two Companies Claim Victory In Platelet Race," *Wall Street Journal*, Thursday, Jun. 16, 1994, B3.
Lok et al., *Nature*, 369:565–568 (1994).
Metcalf, *Nature*, 369:519–520 (1994).
"Scientists Identify, Clone Thrombopoietin," *BioWorld Today*, 5, Thursday, Jun. 16, 1994.
Shields, *Immunol. Res.*, 12:37–47 (1993).
Wendling et al., *Nature*, 369:571–574 (1994).
Stryer., Biochemistry., pp. 23 and 32., Third Edition., W. H. Freeman and Company/New York.

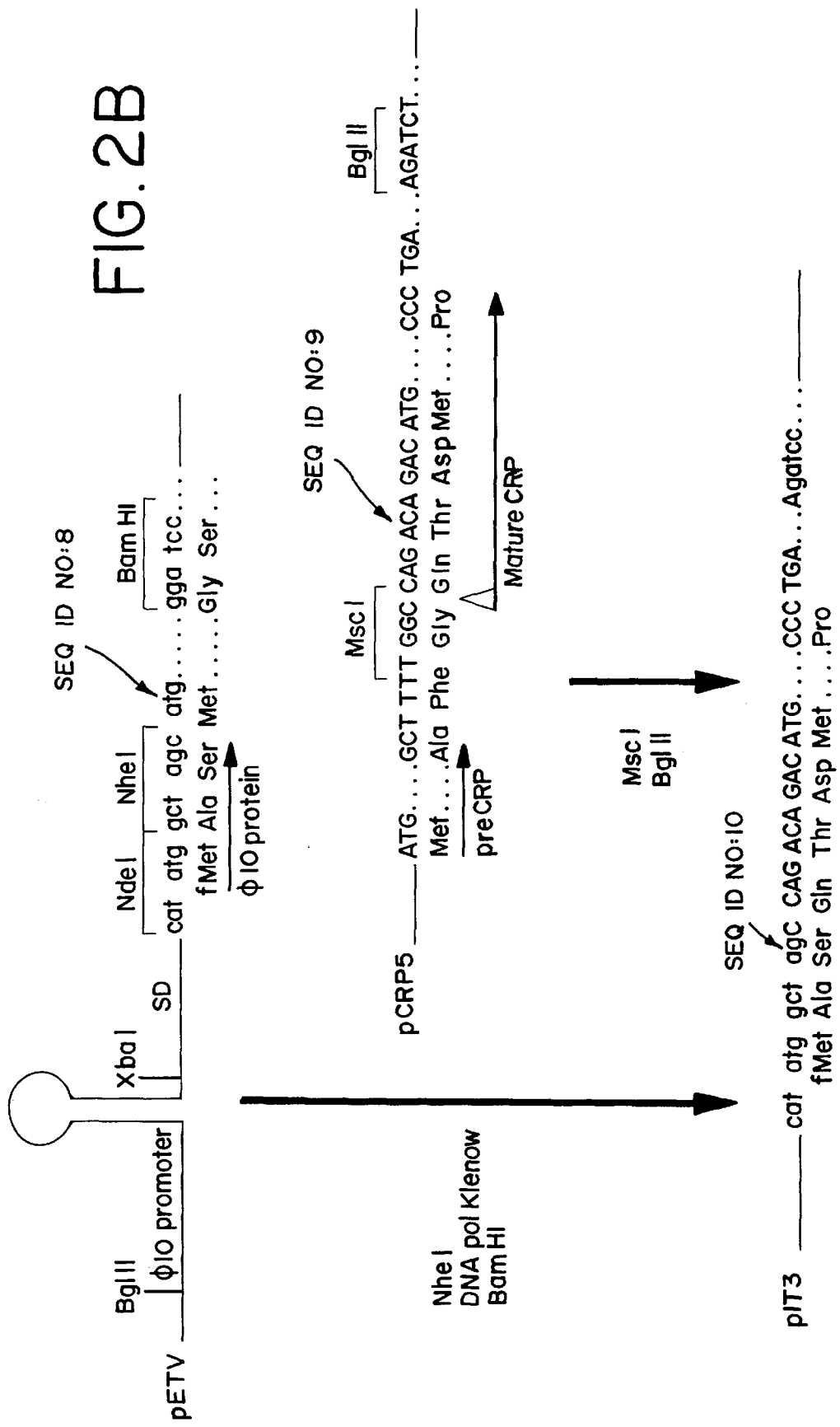

Control - 5 Day Culture

EFFECT OF mCRP ON MURINE THROMBOPOIESIS
CYCLOPHOSPHAMIDE-TREATED – ONE S.C. INJECTION/DAY

EFFECT OF mCRP ON MURINE THROMBOPOIESIS
CHANGES IN PLATELET NUMBER AFTER CHEMOTHERAPY

EFFECT OF mCRP ON MURINE THROMBOPOIESIS
MICE EXPOSED TO 2 GYS (200 RADS) X-IRRADIATION

EFFECT OF mCRP ON MURINE THROMBOPOIESIS
CHANGE IN PLATELET MASS AFTER 2 GY X-IRRADIATION

SEQUENCE LISTING (1) GENERAL INFORMATION:

(iii) NUMBER OF SEQUENCES: 24

(2) INFORMATION FOR SEQ ID NO:1:

(i) SEQUENCE CHARACTERISTICS:
        (A) LENGTH: 28 base
pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

GGGCCATATG CAGACAGACA TGTCGAGG

28

(2) INFORMATION FOR SEQ ID NO:2:

(i) SEQUENCE CHARACTERISTICS:
        (A) LENGTH: 20 base
pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:2:

GAAGCGCCAC AGTGAAGGCT

20

(2) INFORMATION FOR SEQ ID NO:3:

(i) SEQUENCE CHARACTERISTICS:
        (A) LENGTH: 16 base
pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

CACTGTGGCG CTCCAC

16

(2) INFORMATION FOR SEQ ID NO:4:

(i) SEQUENCE CHARACTERISTICS:
        (A) LENGTH: 19 base
pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

TTGTCGCGAT GTGTACTGG

19

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CACATCGCGA CAAGCTG

17

(2) INFORMATION FOR SEQ ID NO:6:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:6:

GGCGAGATCT GAGGTACCTT CAGG

24

(2) INFORMATION FOR SEQ ID NO:7:

(i) SEQUENCE CHARACTERISTICS:
        (A) LENGTH: 12 base pairs
        (B) TYPE: nucleic acid
        (C) STRANDEDNESS: double
        (D) TOPOLOGY: circular (ii) MOLECULE TYPE: cDNA (xi) SEQUENCE DESCRIPTION: SEQ ID NO:7:

TTTGGCCAGA CA

12

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: double
        (D) TOPOLOGY: circular (ii) MOLECULE TYPE: cDNA (xi) SEQUENCE DESCRIPTION: SEQ ID NO:8:

CATATGGCTA GCATG

15

(2) INFORMATION FOR SEQ ID NO:9:

(i) SEQUENCE CHARACTERISTICS:
    (A) LENGTH: 21 base pairs
    (B) TYPE: nucleic acid
    (C) STRANDEDNESS: double
    (D) TOPOLOGY: circular (ii) MOLECULE TYPE: cDNA (xi) SEQUENCE DESCRIPTION: SEQ ID NO:9:

GCTTTTGGCC AGACAGACAT G                      21

(2) INFORMATION FOR SEQ ID NO:10:

(i) SEQUENCE CHARACTERISTICS:
    (A) LENGTH: 24 base pairs
    (B) TYPE: nucleic acid
    (C) STRANDEDNESS: double
    (D) TOPOLOGY: circular (ii) MOLECULE TYPE: cDNA (xi) SEQUENCE DESCRIPTION: SEQ ID NO:10:

CATATGGCTA GCCAGACAGA CATG                   24

(2) INFORMATION FOR SEQ ID NO:11:

(i) SEQUENCE CHARACTERISTICS:
    (A) LENGTH: 10 amino acids
    (B) TYPE: amino acid
    (D) TOPOLOGY: linear (ii) MOLECULE TYPE: protein (xi) SEQUENCE DESCRIPTION: SEQ ID NO:11:

Leu Ser Ser Thr Arg Gly Tyr Ser Ile Phe
 1               5                  10

(2) INFORMATION FOR SEQ ID NO:12:

(i) SEQUENCE CHARACTERISTICS:
    (A) LENGTH: 7 amino acids
    (B) TYPE: amino acid
    (D) TOPOLOGY: linear (ii) MOLECULE TYPE: peptide (xi) SEQUENCE DESCRIPTION: SEQ ID NO:12:

Ser Tyr Phe Gly Leu Arg Ile
 1               5

(2) INFORMATION FOR SEQ ID NO:13:

(i) SEQUENCE CHARACTERISTICS:
    (A) LENGTH: 27 amino acids
    (B) TYPE: amino acid
    (D) TOPOLOGY: linear (ii) MOLECULE TYPE: peptide (xi) SEQUENCE DESCRIPTION: SEQ ID NO:13:

Thr Arg Gly Tyr Ser Ile Phe Ser
Tyr Ala Thr Lys Arg Gln Asp Asn
    1
5
  10
  15

Glu Ile Leu Ile Phe Trp Ser Lys
Asp Ile Gly
              20
              25

(2) INFORMATION FOR SEQ ID NO:14:

(i) SEQUENCE CHARACTERISTICS:
        (A) LENGTH: 81 base
pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

ACCCGTGGGT ACAGTATTTT CTCGTATGCC ACCAAGAGAC AAGACAATGA GA
TTCTCATA      60

TTTTGGTCTA AGGATATAGG A

81

(2) INFORMATION FOR SEQ ID NO:15:

(i) SEQUENCE CHARACTERISTICS:
        (A) LENGTH: 25 amino
acids
        (B) TYPE: amino acid
        (D) TOPOLOGY: linear (ii) MOLECULE TYPE: peptide (xi) SEQUENCE DESCRIPTION: SEQ ID NO:15:

Thr Arg Gly Thr Val Phe Ser Arg
Met Pro Pro Arg Asp Lys Thr Met
    1
5
  10
  15

Arg Phe Ser Tyr Phe Gly Leu Arg
Ile
              20
              25

(2) INFORMATION FOR SEQ ID NO:16:

(i) SEQUENCE CHARACTERISTICS:
        (A) LENGTH: 80 base
pairs
        (B) TYPE: nucleic acid
        (C) STRANDEDNESS: double
        (D) TOPOLOGY: circular (ii) MOLECULE TYPE: cDNA (xi) SEQUENCE DESCRIPTION: SEQ ID NO:16:

ACCCGGGGTA CAGTATTTTC TCGTATGCCA CCAAGAGACA AGACAATGAG AT
TCTCATAT      60

TTTGGTCTAA GGATATAGGA

80

(2) INFORMATION FOR SEQ ID NO:17:

(i) SEQUENCE CHARACTERISTICS:
        (A) LENGTH: 27 amino acids
        (B) TYPE: amino acid
        (D) TOPOLOGY: linear (ii) MOLECULE TYPE: peptide (xi) SEQUENCE DESCRIPTION: SEQ ID NO:17:

Thr Arg Gly Thr Val Phe Ser Arg Met Pro Pro Arg Asp Lys Thr Met
1     5     10     15

Arg Phe Phe Ile Phe Trp Ser Lys Asp Ile Gly
     20     25

(2) INFORMATION FOR SEQ ID NO:18:

(i) SEQUENCE CHARACTERISTICS:
        (A) LENGTH: 81 base pairs
        (B) TYPE: nucleic acid
        (C) STRANDEDNESS: double
        (D) TOPOLOGY: unknown (ii) MOLECULE TYPE: cDNA (xi) SEQUENCE DESCRIPTION: SEQ ID NO:18:

ACCCGGGGTA CAGTATTTTC TCGTATGCCA CCAAGAGACA AGACAATGAG AT TCTTCATA 60

TTTTGGTCTA AGGATATAGG A

81

(2) INFORMATION FOR SEQ ID NO:19:

(i) SEQUENCE CHARACTERISTICS:
        (A) LENGTH: 28 base pairs
        (B) TYPE: nucleic acid
        (C) STRANDEDNESS: double
        (D) TOPOLOGY: circular (ii) MOLECULE TYPE: cDNA (xi) SEQUENCE DESCRIPTION: SEQ ID NO:19:

CCTCGACCCG GGGTACAGTA TTTTCTCG

28

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

CCTCGACCCG TGGTTACAGC ATTTTCTCG
            29

(2) INFORMATION FOR SEQ ID NO:21:

(i) SEQUENCE CHARACTERISTICS:
         (A) LENGTH: 25 base
pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:21:

CCCGCGAAAT TAATACGACT CACTA
            25

(2) INFORMATION FOR SEQ ID NO:22:

(i) SEQUENCE CHARACTERISTICS:
         (A) LENGTH: 29 base
pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:22:

CGAGAAAATG CTGTAACCAC GGGTCGAGG
            29

(2) INFORMATION FOR SEQ ID NO:23:

(i) SEQUENCE CHARACTERISTICS:
         (A) LENGTH: 26 base
pairs
         (B) TYPE: nucleic acid
         (C) STRANDEDNESS: single
         (D) TOPOLOGY: linear (ii) MOLECULE TYPE: cDNA (xi) SEQUENCE DESCRIPTION: SEQ ID NO:23:

CTTTGTTAGC AGCCGGATCC GAGGTA
            26

(2) INFORMATION FOR SEQ ID NO:24:

(i) SEQUENCE CHARACTERISTICS:
         (A) LENGTH: 23 amino
acids
         (B) TYPE: amino acid
         (D) TOPOLOGY: linear (ii) MOLECULE TYPE: peptide (xi) SEQUENCE DESCRIPTION: SEQ ID NO:24:

-continued

```
    Arg Gly Thr Val Phe Ser Arg Met
Pro Pro Arg Asp Lys Thr Met Arg
      1
 5
  10
  15

Phe Ser Tyr Phe Gly Leu Lys
                  20
```

METHODS AND KITS FOR STIMULATING PRODUCTION OF MEGAKARYOCYTES AND THROMBOCYTES

This application is a continuation in part of application Ser. No. 08/202,033, filed Feb. 23, 1994 which issued as U.S. Pat. No. 5,547,931, on Aug. 20, 1996.

FIELD OF INVENTION

The invention relates to methods of stimulating megakaryocytopoiesis and thrombocytopoiesis with modified C-reactive protein ("mCRP") and mutant protein expressing neo-CRP antigenicity. The invention also relates to methods of treating thrombocytopenia, and to kits containing mCRP and the mutant protein.

BACKGROUND OF THE INVENTION

1. CRP Structure and Activity

C-reactive protein was first described by Tillett and Francis [*J. Exp. Med.*, 52:561–71 (1930)] who observed that sera from acutely ill patients precipitated with the C-polysaccharide of the cell wall of *Streptococcus pneumonia*. Other investigators subsequently identified the reactive serum factor as protein, hence the designation "C-reactive protein" or "CRP." Kilpatrick et al., *Immunol. Res.*, 10:43–53 (1991), provides a recent review of CRP.

CRP is a pentameric molecule which consists of five identical subunits [Osmand et al., *Proc. Natl. Acad. Sciences. U.S.A.*, 74:739–743 (1977)]. This pentameric form of CRP is sometimes referred to as "native CRP."

The gene sequence for human CRP has been cloned [Lei et al., *J. Biol. Chem.*, 260:13377–13383 (1985)]. In addition, the primary sequences for rabbit CRP [Wang et al., *J. Biol. Chem.*, 257:13610–13615 (1982)] and murine CRP have been reported [Whitehead et al., *Biochem. J.*, 266:283–290 (1990)], and is under investigation for rat, dog, horse, goat, and sheep. Clinical and laboratory observations have determined that the acute phase response, classically defined by the well-defined changes of the blood [Pepys et al., *Advances in Immunology*, 34:141–212 (1983)], develops during various states of disease and injury including malignant neoplasia, ischemic necrosis, and bacterial, viral, or fungal parasitic infections. Measurement of serum acute phase reactants such as CRP have been utilized in clinical tests for diagnosis and clinical management of patients with various conditions, including systemic lupus erythematosus (SLE) [Bravo et al., *J. Rheumatology*, 8:291–294 (1981)], rheumatoid arthritis [Dixon et al., *Scand. J. Rheumatology*, 13:39–44 (1984)], graft versus host disease [Walker et al., *J. Clin. Path.*, 37:1022–1026 (1984)], as well as many other diseases.

2. Modified-CRP Structure and Activity

In about 1983, another form of CRP was discovered which is referred to as "modified C-reactive protein" or "mCRP." mCRP has significantly different charge, size, solubility and antigenicity characteristics as compared to native CRP [Potempa et al., *Mol. Immunol.*, 20:1165–75 (1983)]. mCRP also differs from native CRP in its binding characteristics. For instance, mCRP does not bind phosphorylcholine [Id.; Chudwin et al., *J. Allergy Clin. Immunol.*, 77:216a (1986)].

The distinctive antigenicity of mCRP has been referred to as "neo-CRP." Neo-CRP antigenicity is known to be expressed on:

1) CRP treated with acid, urea or heat under certain conditions;
2) the primary translation product of DNA coding for human and rabbit CRP; and
3) CRP immobilized on plastic surfaces [Potempa et al., *Mol. Immunol.*, 20:1165–75 (1983); Mantzouranis et al., *Ped. Res.*, 18:260a (1984); Samols et al., *Biochem. J.*, 227:759–65 (1985); Potempa et al., *Mol. Immunol.*, 24:531–541 (1987)]. A molecule reactive with polyclonal antibody specific for neo-CRP has been identified on the surface of 10–25% of peripheral blood lymphocytes (predominantly NK and B cells), 80% of monocytes, and 60% of neutrophils, and as well as at sites of tissue injury [Potempa et al., *FASEB J.*, 2:731a (1988); Bray et al., *Clin. Immunol. Newsletter*, 8:137–140 (1987); Rees et al., *Fed. Proc.*, 45:263a (1986)].

Furthermore, mCRP differs from native CRP in its biological activity. It has been reported that mCRP can influence the development of monocyte cytotoxicity, improve the accessory cell function of monocytes, potentiate aggregated IgG-induced phagocytic cell oxidative metabolism, and increase the production of interleukin-1, prostaglandin E and lipoxygenase products by monocytes [Potempa et al., *Protides Biol. Fluids*, 34:287–290 (1987); Potempa et al., *Inflammation*, 12:391–405 (1988); Chu et al., *Proc. Amer. Acad. Cancer Res.*, 28:344a (1987); Potempa et al., *Proc. Amer. Acad. Cancer Res.*, 28:344a (1987); Zeller et al., *Fed. Proc.*, 46:1033a (1987); Chu et al., *Proc. Amer. Acad. Cancer Res.*, 29:371a (1988)].

In vivo experiments with mCRP were performed to determine if mCRP was capable of providing a protective effect against lethal doses of *Streptococcal pneumonia* [Chudwin et al., *J. Allergy Clin. Immunol.*, 77:216a (1986)]. These studies demonstrated that intravenous administration of mCRP not only protected the animals from lethal *S. pneumonia* doses but that mCRP efficacy was 3 to 4 fold greater than native CRP.

3. Hematopoietic Cell Production and Activity

Pluripotent stem cells in the bone marrow of mammals have the potential to give rise to different types of blood cells which circulate in the peripheral blood. The pluripotent stem cells differentiate into various cell lineages through multiple maturational stages, thereby giving rise to committed blood cell types.

One cell lineage differentiated in the bone marrow is the megakaryocytic lineage. The earliest recognizable member of the megakaryocytic lineage is the megakaryoblast. A morphologic classification commonly applied to the megakaryocyte lineage refers to the megakaryoblast as the earliest cell form, the promegakaryocyte or basophilic megakaryocyte as the intermediate cell form, and the mature megakaryocyte as the final cell form. The mature megakaryocyte then forms and extends filaments of cytoplasm (also called pseudopods) that detach and fragment into individual thrombocytes or platelets. The process of thrombocyte formation, starting from the earliest blast cell stage, typically takes about three days.

Thrombocytes generally circulate in the peripheral blood and play an important role in the body's response to injury or trauma. For example, thrombocytes can become activated and aggregate at the site of injury or trauma. Thrombocytes are also secretory cells, containing various granules which are the secretory organelles of the cell. Such granules include alpha granules, dense granules, and lysosomal granules [Harrison's *Principles of Internal Medicine*, 9th Ed., McGraw-Hill, New York, 1980].

Alpha granules are typically the first granules released from thrombocytes. The alpha granules contain several proteins, including platelet factor 4, beta-thromboglobulin, and fibrinogen. The dense granules are usually released after the alpha granules. The dense granules contain calcium, ADP, serotonin, and catecholamines. The lysosomal granules are usually released last and contain enzymes such as phosphatase, beta-glucuronidase, and cathespin. These proteins and enzymes are released from the thrombocyte granules in response to certain stimuli and assist in potentiating thrombus, or blood clot, formation.

The effects of native CRP and altered forms of CRP on the activation, aggregation, and secretory function of circulating thrombocytes has been the subject of several reports. Fiedel et al., *Immunology*, 45:439–447 (1982), describe that thermally-aggregated CRP induced isolated platelets to aggregate and secrete in in vitro culture. Fiedel et al. also discuss the ability of aggregated CRP to initiate platelet responsiveness and enhance platelet activation in plasma stimulated by various platelet agonists [See also, Fiedel et al., *Clin. Exp. Immunol.*, 50:215–22 (1982)].

Miyazawa et al., *J. Immunol.*, 141:570–74 (1988), report that FA-CRP (defined as human CRP treated with an $Fe^{2+}$-ascorbate) in combination with suboptimal doses of platelet-activating factor and other stimulator agents activated platelets in vitro. The authors also observed that the FA-CRP did not show activity toward rabbit platelets, and therefore, concluded that the activity was species specific.

Fiedel, *Blood*, 65:264–69 (1985), disclose that aggregated human CRP in combination with suboptimal concentrations of ADP in platelet-rich plasma induced platelets to aggregate, secrete dense and alpha-granule constituents, and generate thromboxane $A_2$.

Potempa et al., *Inflammation*, 12:391–405 (1988), disclose that mCRP is capable of activating platelets, PMNL, and monocytes in vitro. The authors also report that in certain culture conditions, mCRP activated platelets to aggregate.

Other investigations have focused on examining the processes by which thrombocytes are made and the factors which influence those processes. The production of thrombocytes has typically been viewed as a process involving two different stages. The first stage is directed to proliferation or differentiation of megakaryocytes. The second stage is directed to maturation or release of the megakaryocytes into thrombocytes. A review of thrombocytopoiesis and megakaryocytopoiesis is provided in *The Platelet*, an International Academy of Pathology Monograph, published by The Williams & Wilkins Company, 1971.

It is generally recognized that different factors are needed for each stage of the production of thrombocytes [See, e.g., Murphy, *Hematol. Oncol. Clin. North Am.*, 3:465–478 (1989)]. A first factor is an inducer of the proliferation or clonal growth of megakaryocyte progenitors. This factor is sometimes referred to as Megakaryocyte Colony Stimulating Factor (Meg-CSF). A second factor is a promoter of maturation of megakaryocytes and formation and release of platelets. This factor is sometimes referred to as a Megakaryocyte-Potentiator (Meg-POT) factor. Factors which exhibit Megakaryocyte-potentiator activity typically have the ability to promote megakaryocyte colony formation in the presence of Meg-CSF, to stimulate megakaryocyte polyploidization, and induce the maturation of megakaryocytes.

Thrombocytopoiesis and megakaryocytopoiesis may be adversely affected by different diseases or pathological conditions. Cell production may also be adversely affected by radiation, drugs, or surgery. While therapies such as surgery, chemotherapy, and radiation have improved, they are nonetheless often accompanied by damage to bone marrow and/or other blood cell-producing tissues.

In diagnosing such conditions or monitoring the effects of certain therapies, platelet counts in the peripheral blood are typically measured. A decrease in the number of platelets in the blood can occur in certain medical disorders [Marchasin et al., *California Medicine*, 101:95–100 (1964)]. Thrombocytopenia, a medical condition characterized by a low platelet count in the blood, can result from impaired production of platelets by the bone marrow, platelet sequestration in the spleen, or increased destruction of platelets in the peripheral circulation. Further, for patients receiving large volumes of rapidly administered platelet-poor blood products, thrombocytopenia can develop due to dilution of the blood.

In addition to measuring platelet numbers, platelet volume, also referred to as mean platelet volume ("MPV"), can be measured. An increase in MPV has been associated with increased megakaryocyte size in response to thrombopoietic stress [Thompson et al., *Blood*, 72:1 (1988)]. It has also been observed that platelet count and MPV are inversely related, i.e., patients with low platelet counts tend to have larger MPV and patients with high platelet counts tend to have smaller MPV [Id.]. This inverse relationship has been interpreted as one mechanism by which the body maintains a relatively stable platelet mass. The "platelet mass" is determined by multiplying the platelet number by the mean platelet volume.

Thrombocytopenia and other conditions characterized by abnormal platelet numbers or volume have been treated in various ways. One method employed to treat thrombocytopenia is platelet transfusion. Platelet transfusions can be effective in some circumstances, but are undesirable because of the costs and risk of infections.

Certain cytokines, humoral factors, and chemical compounds have been identified as inducing thrombocyte production and megakaryocyte growth [See, for example, U.S. Pat. No. 5,126,325 (human B cell differentiation factor); U.S. Pat. No. 5,032,396 (interleukin-7); U.S. Pat. No. 5,250,732 (ketamine analogues); U.S. Pat. No. 5,260,417 (megakaryocyte growth promoting factor, "MGPA")]. In vitro, interleukin-3 (IL-3), interleukin 6 (IL-6) interleukin-11 (IL-11) and granulocyte-macrophage colony-stimulating factor (GM-CSF) have been reported to increase the number and size of megakaryocyte colonies [Williams, *Immunol. Ser.*, 49:215–229 (1990); Hoffman et al., *Yale J. Biol. Med.*, 63:411–418 (1990); Yonemura et al., *Exp. Hematol*, 20:1011 (1992); Teramura et al., *Blood*, 79:327 (1992); Carrington et al., *Blood*, 77:34 (1991)]. IL-3 is believed to principally affect the differentiation (earliest) phase of the thrombopoiesis process [Moore et al., *Blood*, 78:1 (1991); Sonoda et al., *PNAS USA*, 85:4360 (1988)]. In contrast, IL-11 has been reported to influence thrombopoiesis principally at the maturation (later) phase [Teramura et al., *Blood*, 79:327 (1992); Yonemura et al., *Exp. Hematol.*, 20:1011 (1992)].

Several investigators have reported that in vivo administration of interleukin-6 increased thrombocyte counts in the peripheral blood of primates [Asano et al., *Blood*, 75:1602 (1990)] and mice [Podja et al., *Exp. Hematol.*, 18:1034 (1990); Ishibashi et al., *Blood*, 74:1241 (1989)]. Carter et al. reported that administration of exogenous thrombopoietin decreased the severity and duration of radiation-induced thrombocytopenia in mice [*Radiation Research*, 132:74–81 (1992)].

SUMMARY OF THE INVENTION

The invention provides a method of stimulating thrombocytopoiesis in a mammal comprising administering to the mammal an effective amount of modified C-reactive protein or mutant protein expressing neo-CRP antigenicity in a pharmaceutically-acceptable carrier.

The invention also provides a method of treating thrombocytopenia comprising administering to a mammal diagnosed as having thrombocytopenia an effective amount of modified C-reactive protein or mutant protein expressing neo-CRP antigenicity in a pharmaceutically-acceptable carrier.

The invention also provides a method for promoting maturation of megakaryocytes in vitro. The method comprises the steps of providing hematopoietic cells in a cell culture medium and culturing the cells in the presence of an effective amount of modified C-reactive protein or mutant protein expressing neo-CRP antigenicity.

The invention further provides an article of manufacture and kit containing materials useful for stimulating thrombocytopoiesis and megakaryocytopoiesis. The article of manufacture comprises a container, a label on the container, and a composition contained within the container, the composition being effective for stimulating thrombocytopoiesis and megakaryocytopoiesis, and the label on the container indicating that the composition can be used for stimulating thrombocytopoiesis and megakaryocytopoiesis. The active agent in the composition comprises modified C-reactive protein or mutant protein expressing neo-CRP antigenicity. The kit comprises the container holding the composition effective for stimulating thrombocytopoiesis and megakaryocytopoiesis, as well as other compositions such as buffers and diluents.

BRIEF DESCRIPTION OF THE DRAWINGS

FIGS. 2A and 2B illustrate the preparation of plasmid pIT3.

DETAILED DESCRIPTION OF THE PRESENTLY PREFERRED EMBODIMENTS

Figure 1A:
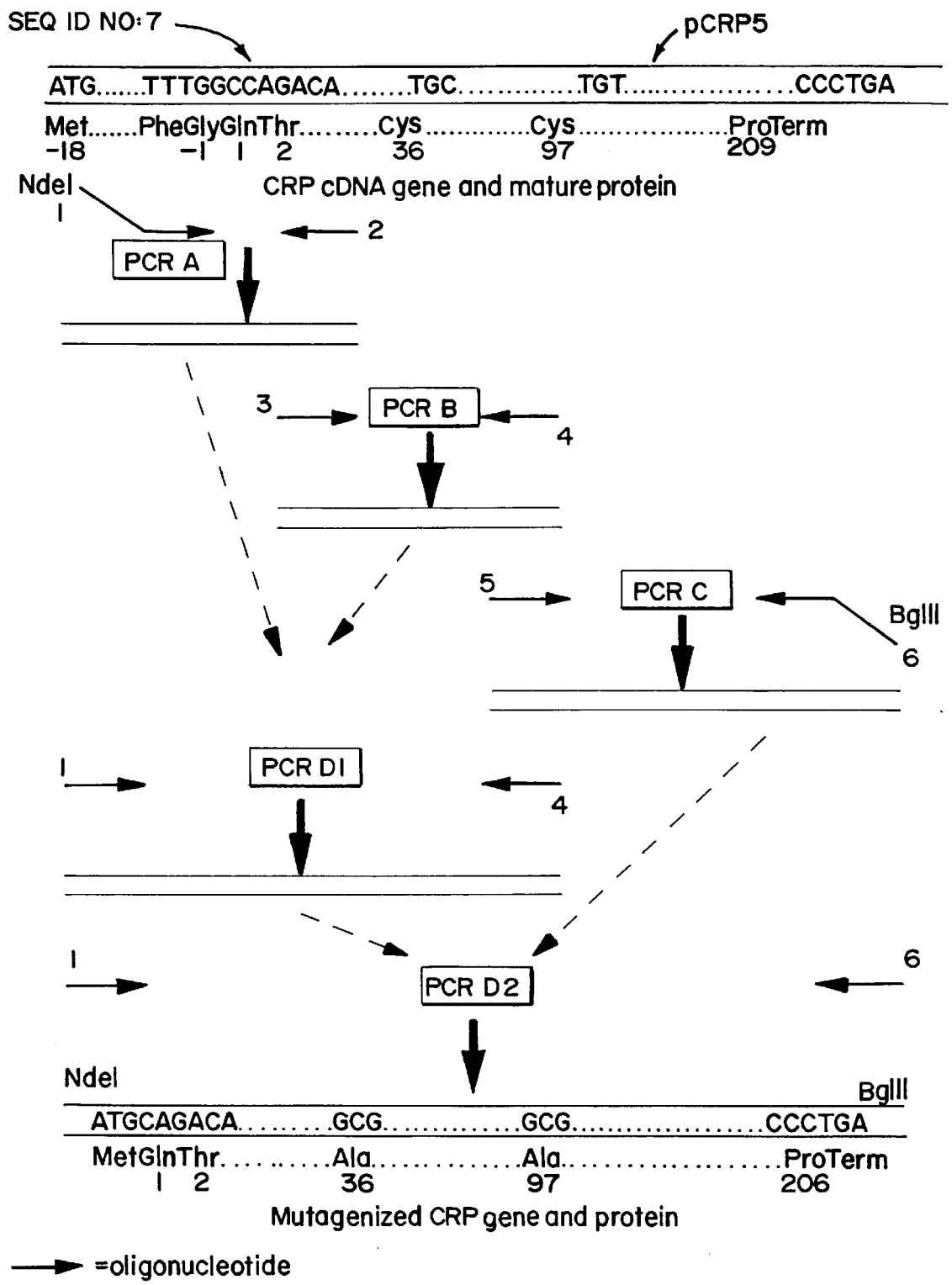
FIG. 1A is a diagram of a series of polymerase chain reactions used to produce a recombinant mutant protein expressing neo-CRP antigenicity.

The present invention provides methods for stimulating megakaryocytopoiesis and thrombocytopoiesis using modified C-reactive protein ("mCRP"). As discussed in the Background section, mCRP is a modified form of CRP which expresses neo-CRP antigenicity. Neo-CRP antigenicity is expressed on mCRP but not on native CRP.

The formation of mCRP involves the dissociation of native CRP into its subunits. The formation of mCRP also involves a change in the conformation of the subunits. Although the subunits tend to self-aggregate [Potempa et al., *Mol. Immunol.*, 24:531–41 (1987)], the subunits in the aggregate form also express neo-CRP antigenicity. Accordingly, mCRP employed in the invention may consist of free subunits and/or aggregates of subunits. Dissociated subunits do not reassemble into native CRP; the change from native CRP to mCRP is irreversible [Potempa et al., *Fed. Proc.*, 44:1190a (1985); Kresl et al., *FASEB J.*, 5:633a (1991)].

The mCRP useful in the practice of the present invention can be prepared in a number of ways. For instance, the mCRP can be prepared using native CRP as a starting material. Methods of isolating native CRP from natural sources are known in the art and are described, for example, by Volanakis et al., *J. Immunol.*, 113:9–17 (1978); de Beer et al., *J. Immunol. Meth.*, 50:17–31 (1982); Potempa et al., *Mol. Immunol.*, 24:531–541 (1987). CRP is preferably isolated from serum, plasma, or pleural or ascites fluid by calcium-dependent affinity chromatography using phosphorylcholine-substituted BioGel® A 0.5 m (an agarose-based resin obtained from BioRad Laboratories, Richmond, Calif.) [See, Potempa et al., *Mol. Immunol.*, 24:531–541 (1987)]. This CRP isolation method is further described in Example 1 below. Using this isolation method, CRP can be obtained which is about 99% pure. Partially purified CRP may also be obtained from commercial sources, such as Western States Plasma (Fallbrook, Calif.).

Methods of making mCRP from CRP are also known in the art [See, e.g., Potempa et al., *Mol. Immunol.*, 20:1165–1175 (1983); Potempa et al., *Mol. Immunol.*, 24:531–541 (1987)]. For instance, mCRP can be prepared by denaturing CRP. CRP can be denatured by treatment with an effective amount of urea (preferably 8M) in the presence of a conventional chelator (preferably ethylenediamine tetraacetic acid (EDTA) or citric acid). Further, CRP can be treated to produce mCRP by adjusting the pH of the protein to below about 3 or above about 11–12. Finally, mCRP can be produced by heating CRP above 50° C. for a time sufficient to cause denaturation (preferably at 63° C. for 2 minutes) in the absence of calcium or in the presence of a chelator Methods of producing the mCRP from CRP using such techniques are also described further below in Example 1.

The mCRP prepared according to these methods may be from any species. There is substantial homology between the amino acid sequences of CRP from different species. For instance, there is from about 50% to about 80% sequence homology between CRP from various mammalian species [Hu et al., *Biochem.*, 25:7834–39 (1986); Whitehead et al., *Biochem. J.*, 266:283–90 (1990); Kilpatrick et al., *Immunol. Res.*, 10:43–53 (1991)]. It is, therefore, expected that mCRP from any species will be effective in the presently claimed invention. Thus, a mammal may be treated with mCRP from a different species (e.g., mice can be treated with human mCRP). Alternatively, and preferably, the mammal is treated with homologous mCRP (e.g., humans are treated with human mCRP) to avoid immune reactions to the mCRP.

CRP and mCRP may also be prepared using genetic engineering techniques and procedures of molecular biology. The primary translation product of the CRP gene (called preCRP, the CRP subunit with a presequence at the amino terminus) expresses neo-CRP antigenicity [Mantzouranis et al., *Ped. Res.*, 18:260a (1984)]. Accordingly, mCRP can be prepared by selecting conditions so that the CRP subunits are not assembled into pentameric native CRP in the host cell. This can be accomplished by expressing the desired genomic or cDNA clone in a prokaryotic host [See Samols et al., *Prot. Biol. Fluids*, 34:263–66 (1986)]. The mCRP produced in this manner may consist of aggregates of CRP subunits and/or preCRP and perhaps other CRP peptides. See Id. This form of mCRP is insoluble, and further purification may be problematical. However, it should be possible to inject this insoluble material into mammals as a suspension without further processing, since an aggregated form of mCRP prepared from CRP purified from plasma has been shown to be effective, as described further in the Examples below.

As used in the present invention, the term "mCRP" is intended to refer to subunits of CRP, in free or aggregate form, which express neo-CRP antigenicity. It is believed that fragments of the CRP subunits may have the same activities described herein for mCRP, and the use of such fragments is considered to come within the scope of the present invention. It is also believed that proteins substantially homologous to CRP will have the activities described herein for mCRP, and such proteins are also considered to come within the scope of the present invention.

The mCRP discussed above may be characterized and distinguished from native CRP on the basis of physiochemical properties, binding characteristics or biological activities. As noted above, mCRP expresses neo-CRP antigenicity, whereas native CRP does not. Neo-CRP antigenicity can be detected using polyclonal antisera specific for neo-CRP [See, Potempa et al., *Mol. Immunol.*, 24:531–541 (1987)]. Preferably, however, mCRP is distinguished from native CRP using monoclonal antibodies like those described in U.S. Pat. No. 5,272,257, the disclosure of which is incorporated herein by reference. Hybridomas secreting the monoclonal antibodies disclosed in U.S. Pat. No. 5,272,257 are deposited with the American Type Culture Collection, Rockville, Md., and are registered as HB10175 (mAb 15.2C10), HB10176 (mAb 26.8C10), HB10177 (mAb 13.3H12), and HB10178 (mAb 15.1D6). These monoclonal antibodies are also described in Ying et al., *J. Immunol.*, 143:221–28 (1989). The antisera and antibodies can be used, for example, in ELISA assays to distinguish mCRP from native CRP.

In addition, mCRP may be distinguished from native CRP on the basis of charge, solubility, binding characteristics and biological activity as referenced in the Background section. The biological activities of mCRP include its ability to bind aggregated immunoglobulin and immune complexes which allows mCRP to be used to removed aggregated immunoglobulin and immune complexes from fluids (such as antibody reagents or body fluids), to quantitate immune complexes, and to reduce the levels of immune complexes in a mammal in need thereof. However, to show that a preparation contains mCRP, it is usually sufficient to establish that the preparation 1) reacts positively with an antibody specific for an epitope found only on mCRP or 2) binds aggregated immunoglobulin (e.g., aggregated IgG).

The methods of the invention may alternatively employ a mutant protein which expresses neo-CRP antigenicity. The mutant protein has at least one amino acid added, deleted or replaced as compared to an unmutated CRP subunit or unmutated preCRP. However, the mutant protein may have several amino acid changes as compared to the unmutated CRP subunit or unmutated preCRP. For instance, the mutant protein may have several added amino acids, several deleted amino acids, several replacement amino acids, or a combination of added, deleted or replacement amino acids, as compared to the unmutated CRP subunit or preCRP. Examples of the mutant protein of the invention are described in Example 2 below, and are referred to as "mutant rCRP's." Mutant proteins of the invention are also described in co-owned and co-pending U.S. patent application Ser. No. 08/296,545, filed Aug. 26, 1994, now abandoned.

The amino acid(s) added, deleted and/or replaced are chosen so that the mutant protein retains neo-CRP antigenicity. The amino acid(s) can be identified, for example, by using group-specific modification reactions like those discussed in *Chemical Modifications of Proteins*, G. E. Means and R. E. Feeney, Holden-Day, Inc. San Francisco, Calif. (1971) and *Chemistry of Protein Conjugation and Cross-linking*, S. S. Wong, CRC Press Boca Raton, Fla. (1991). For instance, amino acid residues in a protein having a free primary amine group such as is found in lysine residues can have the primary amine group altered using various anhydride agents such as acetic anhydride, succinic anhydride, or maleic anhydride. Accessible primary amine groups can also be modified using reductive alkylation reactions with various aldehyde and ketone groups. Amino acid(s) and/or peptide regions which comprise selective antigenic epitopes specific for neo-CRP antibodies may also be defined by peptide mapping techniques as described in Ying et al., *Mol. Immunol.*, 29:677–687 (1992).

It is preferable to choose such amino acid(s) addition, deletion, and/or replacement so that the mutant protein is less likely to form non-dissociable aggregates than the unmutated CRP subunit or unmutated preCRP. Suitable amino acid changes include the deletion or replacement of at least one, preferably all, of the cysteines in an unmutated CRP subunit or unmutated preCRP. All CRP subunits and preCRP's contain at least one cysteine. Mammalian CRP subunits contain two cysteines and mammalian preCRP's contain three cysteines. It is believed that some of these cysteines form intermolecular disulfide bonds, thereby contributing to the formation of non-dissociable cross-linked aggregates. Therefore, one, two, or preferably all three, of these cysteines are desirably deleted or replaced. When the cysteines are replaced with other amino acids, they are preferably replaced with glycine, alanine, valine, leucine, isoleucine, serine, threonine or methionine, but any amino acid can be used. Most preferred is substitution with alanine.

As a result of the amino acid changes in them, the mutant proteins of the invention are easier to purify with much higher yields than unmutated CRP subunits or unmutated preCRP's. (See, e.g., Example 2). Also, the final product is much purer with many fewer aggregates and fragments than that obtained with unmutated CRP subunits or unmutated preCRP's.

Not all of the amino acid additions, deletions and replacements need contribute to the reduced likelihood of forming non-dissociable aggregates as long as the combined effect of all the changes is a reduction in intermolecular non-dissociable cross-linking. For instance, the recombinant DNA manipulations used to produce the mutant proteins may result in amino acids being added at the amino or carboxy terminal ends of the CRP subunit. This is acceptable as long as these amino acids do not contribute to the production of non-dissociable aggregates (See, e.g., Example 2). In addition, some of the amino acid changes may be made for other purposes. For instance, it is desirable to make amino acid changes which increase the solubility of the resultant mutant protein in aqueous media, since a more soluble mutant protein is easier to purify and process. It has been found that the solubility of the mutant proteins of the invention is improved if lysine residues are chemically altered by treatment with sulfo-N-hydroxysuccinimide-acetate (sulfo-NHS-acetate; which changes the positive charge of the epsilon amine group of lysine to a neutral charge), sulfo-succinimidyl-3-(4-hydroxyphenyl) propionate (which changes the positive charge of the epsilon amine group of lysine to a neutral charge and adds an aromatic functional group), or succinic anhydride (which changes the positive charge of the epsilon amine group of lysine to a negative charge). Therefore, one or more of the lysine residues of an unmutated CRP subunit or preCRP is preferably deleted or replaced with another amino acid to improve the solubility of the resultant mutant protein. Other suitable amino acid changes to increase the solubility of the mutant proteins of the invention include deleting one or more hydrophobic amino acids, replacing one or more hydrophobic amino acids with charged amino acids, adding one or more charged amino acids, or combinations of these changes. However, for the reasons stated above, the addition of lysine residues should be avoided. Aqueous media include water, saline, buffers, culture media, and body fluids.

The mutant proteins of the invention can be prepared by expression of DNA coding for them in transformed host cells. DNA coding for a mutant protein according to the invention can be prepared by in vitro mutagenesis of a CRP genomic or cDNA clone or can be chemically synthesized.

As discussed above, genomic and cDNA clones coding for human, mouse, and rabbit CRP have been isolated, and there is substantial homology between the amino acid sequences of CRP's from different species. Given the substantial homology between CRP's from different species, probes can readily be prepared so that genomic and cDNA clones can be isolated which code for CRP's from other species. Methods of preparing such probes and isolating genomic and cDNA clones are well known [See, e.g., Lei et al., *J. Biol. Chem.*, 260, 13377–83 (1985); Woo et al., *J. Biol. Chem.*, 260:13384–88 (1985); Hu et al., *Biochem.*, 25:7834–39 (1986); Hu et al., *J. Biol. Chem.*, 263:1500–1504 (1988); Whitehead et al., *Biochem. J.*, 266:283–90 (1990)].

Using one of the known clones or a newly-isolated clone, DNA coding for a mutant protein according to the invention can be prepared using conventional and well known in vitro mutagenesis techniques. Particularly preferred is site-directed mutagenesis using polymerase chain reaction (PCR) amplification. See Example 2. The following references describe other site-directed mutagenesis techniques which can be used to produce DNA coding for a mutant protein of the invention: *Current Protocols In Molecular Biology*, Chapter 8, (Ansubel ed. 1987); Smith & Gilliam, *Genetic Engineering Principles And Methods*, 3:1–32 (1981); Zoller & Smith, *Nucleic Acids Res.*, 10:6487–6500 (1982); Zoller et al., *Methods Enzymol.*, 100:468–500 (1983); Zoller & Smith, *DNA*, 3:479–88 (1984); Brake et al., *Proc. Natl. Acad. Sci. USA*, 81:4642–46 (1984); *Bio/Technology*, pages 636–39 (July 1984); Botstein et al., *Science*, 229:1193 (1985); Kunkel et al., *Methods Enzymol.*, 154:367–82 (1987).

DNA coding for a mutant protein of the invention can also be prepared by chemical synthesis. Methods of chemically synthesizing DNA having a specific sequence are well-known in the art. Such procedures include the phosphoramidite method [See, e.g., Beaucage and Caruthers, *Tetrahedron Letters*, 22:1859 (1981); Matteucci and Caruthers, *Tetrahedron Letters*, 21:719 (1980); and Matteucci and Caruthers, *J. Amer. Chem. Soc.*, 103:3185 (1981)] and the phosphotriester approach [See, e.g., Ito et al., *Nucleic Acids Res.*, 10:1755–69 (1982)].

To show that the mutant protein expresses neo-CRP antigenicity, it is usually sufficient to establish that the protein 1) reacts positively with an antibody specific for an epitope found only on mCRP or 2) binds aggregated immunoglobulin (e.g., aggregated IgG).

The methods of the invention are described in further detail below, and refer to the use of mCRP. It is contemplated that the mutant protein(s) disclosed above may be similarly employed.

In accordance with the method of the invention of stimulating thrombocytopoiesis in a mammal, an effective amount of mCRP is administered to the mammal. The term "thrombocytopoiesis" refers generally to the process by which thrombocytes, or platelets, are made. The mCRP may be administered to the mammal when a decrease in thrombocyte number, volume and/or mass in the mammal is first detected. The mCRP may also be administered at the time of, or after, administering to the mammal therapy which may adversely affect thrombocyte number, volume and/or mass. For instance, the mCRP may be administered to the mammal within several hours of receiving relatively high doses of X-irradiation. Alternatively, the mCRP may be administered prophylactically, i.e., prior to therapy, to avoid decreased thrombocyte number, volume, and/or mass. As an example, the mCRP is administered to the mammal 1 to 5 days before the mammal is infused with a chemotherapy drug.

The mCRP may be administered to the mammal in a pharmaceutically-acceptable carrier. Pharmaceutically-acceptable carriers are well known to persons skilled in the art. For instance, suitable carriers for administering mCRP include fluids such as water, saline, and buffer. More preferably, a Tris or phosphate buffered saline is used as the carrier. It will be apparent to those persons skilled in the art that certain carriers may be more preferable depending upon, for instance, the route of administration and concentration of protein being administered.

The mCRP is preferably administered to the mammal by injection (e.g., intravenous, intraperitoneal, subcutaneous, intramuscular). Effective dosages and schedules for administering MCRP may be determined empirically, and making such determinations is within the skill of the art. A dose of about 0.1 to 10 mg of mCRP per kilogram of body weight of the mammal will be effective for stimulating thrombocytopoiesis. A dose of about 3 mg of mCRP per kilogram of body weight is preferred. It is understood by those skilled in the art that the dose of mCRP that must be administered will vary depending on, for example, the mammal which will receive the mCRP, the nature of the medical condition or therapy believed to be responsible for decreased thrombocyte numbers, volume and/or mass, the extent of damage to the blood cell producing tissues, the route of administration, and the identity of any other drugs being administered to the mammal. It is also understood that it may be necessary to give more than one dose of mCRP. Generally, multiple doses of mCRP must be given to the mammal. The interval between doses is preferably from about 1 day to about 7 days. Administration of mCRP should be continued until acceptable thrombocyte number, volume and/or mass has been restored to the mammal.

The invention also provides a method of treating thrombocytopenia in a mammal. The term "thrombocytopenia" in the present invention is used in a broad sense and refers to the physiological condition in mammals usually characterized by an abnormally low thrombocyte number in the peripheral blood.

In the method, the mammal is first diagnosed as suffering from thrombocytopenia. Making the diagnosis is within the skill in the art. Those skilled in the art will also appreciate that different thrombocyte levels may warrant a thrombocytopenia diagnosis for different mammalian species. The diagnosis is usually made in humans when thrombocyte levels in the peripheral blood fall below 100,000 cells per cubic millimeter. Thrombocytopenia can be the result of a disorder of production, distribution or destruction of thrombocytes or thrombocyte-producing cells. To treat the thrombocytopenia, the mCRP is administered to the mammal according to the modes and schedules of administration described above.

The thrombocytopoietic activity in the mammal can be measured or monitored in various ways. For instance, the activity can be measured using in vitro assays. One such assay is the colony forming assay. These assays are known in the art and generally involve harvesting bone marrow cells from the mammal and culturing the cells in a clot or soft agar [Mizoguchi et al., *Exp. Hematol.*, 7:346 (1979); Metcalf, D., *In Hematopoietic Colony Stimulating Factors*, Elsevier/North Holland, Amersterdam (1984)]. By using select reagents and stains in the colony forming assays, the following activities can be measured or monitored: (1) basic formation and growth of megakaryocyte colonies (Meg-CSF activity) and (2) potentiation/maturation of megakaryocytes during later phases leading up to and during platelet release (Meg-POT activity). In addition, there are in vitro liquid culture assays. For example, acetylcholinesterase (AChE) enzyme activity quantitatively correlates with megakaryocyte numbers in liquid culture [See, Burstein et al., *J. Cellular Phys.*, 122:159 (1985)]. Those skilled in the art will appreciate, however, that the AChE assay may not be suitable in some instances since AChE is not found in all mammalian megakaryocytes.

The thrombocytopoietic activity in the mammal can also be monitored by peripheral blood or bone marrow analysis. Thrombocyte levels in the circulating blood can be determined by cell count analysis. The cell count analysis may be performed by measuring a Coulter Panel using the Coulter Model S-plus instrument. Thrombocytopoietic activity may also be assessed by examining cells morphologically. For example, bone marrow samples can be obtained from the mammal and prepared for microscopy using standard histological techniques known in the art. By staining the bone marrow cells, one can observe the size and number of megakaryocytes in the marrow sample.

Although not fully understood, it is believed that the stimulating effect of mCRP on thrombocytopoiesis in vivo may be due, at least in part, to the localization of mCRP to the bone marrow. Data (not shown) has indicated that intravenously-injected mCRP rapidly localized to the bone marrow in mice within 4 hours after administration and remained there for at least 24 hours.

The mCRP can also be employed to stimulate megakaryocytopoiesis and thrombocytopoiesis in vitro. In a preferred embodiment, there is provided a method for promoting megakaryocyte growth and maturation in vitro. The method comprises the steps of providing hematopoietic cells in a cell culture medium and culturing the cells in a culture vessel in the presence of an effective amount of mCRP. The use of mCRP to promote megakaryocyte growth and maturation in vitro has a variety of applications. For instance, the mCRP can be used in bone marrow colony forming assays to screen and detect the extent of cell damage caused by radiation or drug therapy in vivo. It is also believed that hematopoietic cells grown in vitro in the presence of mCRP can be infused back into hematopoietically compromised patients.

In the method, hematopoietic cells are provided in a cell culture medium. The term "hematopoietic cells" is used to refer to cells or cell samples suspected of containing pluripotent or immature stem cells (which may be megakaryocyte precursor cells) or cells of the megakaryocytic lineage. Although the preferred method utilizes bone marrow cells, it is contemplated that other hematopoietic cell samples suspected of containing stem cells or cells of the megakaryocyte lineage may be employed. The hematopoietic cell samples may be obtained, for example, from peripheral blood or from umbilical cord blood.

The cells used in the method may be obtained directly from the mammal. For instance, bone marrow cells can be obtained by flushing the femur bones of the mammal. The cells can also be obtained through various techniques known in the art, including but not limited to, needle biopsy or needle aspiration. Preferably, the cells are obtained under relatively aseptic or sterile conditions.

The cells are then placed in an aqueous isotonic or buffered medium. Preferably, the cells are placed in a sterile tissue culture medium. Suitable tissue culture media are well known to persons skilled in the art and include, but are not limited to, Basal Medium Eagle ("BME"), Minimal Essential Medium ("MEM"), RPMI-1640, Dulbecco's Modified Eagle's Medium ("DMEM"), and McCoy's 5A Medium. These tissue culture media may be purchased commercially from various sources, including Sigma Chemical Company (St. Louis, Mo.) and GIBCO (Grand Island, N.Y.).

More preferably, the cells are placed in a sterile tissue culture medium containing a sufficient amount of antibiotic agent to prevent microbial contamination. Penicillin, streptomycin, and gentamicin, as well as other tissue culture grade antibiotics known in the art, are commercially available from Sigma and GIBCO, and may be added to the aqueous medium in concentrations recommended by the manufacturer. Microbial contamination may also be reduced by the use of routine sterile techniques in handling the cells and the use of a laminar flow hood.

The cells are then preferably counted to determine the approximate concentration and viability of the cells. Concentration and viability of the cells may be determined by standard techniques known in the art. For example, cell viability may be determined by trypan blue exclusion methods.

The cells are then cultured in a suitable cell culture medium under conditions sufficient for the cells to remain viable and grow. Preferably, the cell culture medium comprises a sterile tissue culture medium supplemented with a sufficient quantity of nutrient components. Suitable tissue culture media include, but are not limited to, BME, MEM, RPMI-1640, DMEM, and McCoy's 5A medium, all of which are commercially available from Sigma or Gibco. Nutrient components contemplated by the invention include, but are not limited to, amino acids, lipids and hormones. The cell culture medium also preferably includes at least one antibiotic agent to prevent microbial contamination.

The cells can be cultured in a variety of ways, including culturing in a clot, in agar, or in liquid culture [Mizoguchi et al., *Exp. Hematol.*, 7:346 (1979); Metcalf, D., *In Hematopoietic Colony Stimulating Factors*, Elsevier/North Holland, Amersterdam (1984); Burstein et al., *J. Cellular Phys.*, 122:159 (1985)]. The cells are preferably cultured in a vessel suitable for sterile tissue culture, including but not limited to, plates and dishes. The culture vessel may be formed from a variety of materials such as glass or plastic. Culture vessels are commercially available from COSTAR (Cambridge, Mass.) and Corning (Corning, N.Y.) The optimum number of cells cultured in the culture vessel may be determined empirically by those persons skilled in the art without undue experimentation. In a preferred embodiment, about $5 \times 10^5$ bone marrow cells/ml are cultured in a Petrie dish.

In one embodiment, bone marrow cells are cultured in agar. For culturing purposes, both the culture vessel and agar should be sterile. Agar solutions may be sterilized by heating to relatively high temperatures. Preferably, the agar solution is sterilized by autoclaving for 15 minutes (250° F. at 15 psi). Upon heating, the agar will go into suspension. Upon cooling, the solution will become a semi-solid gel. In another embodiment, bone marrow cells are cultured in a plasma clot attached to a culture vessel. An example of this culturing method is further described in Example 3 below. In a further embodiment, the bone marrow cells are cultured in a continuous liquid culture.

The cells are cultured in the culture vessel in the presence of an effective amount of mCRP. The concentration of mCRP in the reagent may vary and will be added to the culture at a dose determined empirically by those in the art. The concentration of mCRP in the culture will depend on various factors, such as the kind of cell culture medium employed, and the length of time of the cell culturing period. The desired concentrations may be determined empirically and it is within the skill in the art to make such determinations. As described in Example 3, Applicant found that about 2 to 20 microgram/ml mCRP was effective for promoting megakaryocyte colony formation and maturation in vitro. For comparative purposes, appropriate controls should also be cultured and tested to determine the efficacy of the mCRP and to quantitate results.

The culture vessels containing the cells and mCRP (or controls) are then incubated under conditions sufficient for the cells to remain viable and grow. Preferably, the culture vessels are incubated in a humidified chamber for about 4 to about 7 days. The specific temperature and time of incubation, as well as other culture conditions, can be varied depending on such factors as the concentration of the mCRP. Those skilled in the art will be able to determine operative and optimal culture conditions without undue experimentation. Growth and maturation of megakaryocytes in the cultures can then be determined by counting the number of colonies formed in each culture vessel and/or by examining the morphological characteristics of the cells under a microscope.

The invention further provides an article of manufacture and kit containing materials useful for stimulating thrombocytopoiesis and megakaryocytopoiesis. The article of manufacture comprises a container with a label. Suitable containers include, for example, bottles, vials, and test tubes. The containers may be formed from a variety of materials such as glass or plastic. The container holds a composition which is effective for stimulating thrombocytopoiesis and megakaryocytopoiesis. The active agent in the composition is mCRP or mutant protein having neo-CRP antigenicity. The label on the container indicates that the composition is used for stimulating thrombocytopoiesis and megakaryocytopoiesis, and may also indicate directions for either in vivo or in vitro use, such as those described above.

The kit of the invention comprises the container described above and may further include other materials desirable from a commercial and user standpoint, including but not limited to buffers, diluents, filters, needles, syringes, cell culture medium and culture vessels.

EXAMPLES

Example 1
Isolation and Purification of mCRP
A. CRP Preparation and Purification Native CRP was isolated from pleural or ascites fluid by calcium-dependent affinity chromatography using phosphorylcholine-substituted BioGel® A 0.5 m (an agarose-based resin obtained from BioRad Laboratories) as described by Volanakis et al. [*J. Immunol.*, 113:9–17 (1978)] and modified by Potempa et al., [*Mol. Immunol.*, 24:531–41 (1987)]. Briefly, the pleural or ascites fluid was passed over the phosphorylcholine-substituted column, and the CRP was allowed to bind. Then, the column was exhaustively washed with 75 mM Tris-HCl-buffered saline (pH 7.2) containing 2 mM $CaCl_2$ until the absorbance at 280 nm was less than 0.02. The CRP was eluted with 75 mM Tris, 7.5 mM citrate-buffered saline (pH 7.2). This high concentration of Tris significantly reduces non-specifically adsorbed proteins which often contaminate affinity-purified CRP preparations. CRP-containing fractions were pooled, diluted three-to-five fold with deionized water, adsorbed to Q-Sepharose Fast Flow® ion exchange resin, and then eluted with a linear salt gradient from 0–1M NaCl in 10 mM Tris-HCl, pH 7.4. CRP-containing fractions were pooled and re-calcified to 2–5 mM $CaCl_2$ (by adding a suitable amount of a 1M solution) and applied to unsubstituted Biogel® A 0.5 m column to remove residual serum amyloid P component ("SAP"). Then, the CRP was concentrated to 1 mg/ml using ultrafiltration (Amicon; PM30 membrane) under 10–20 psi nitrogen. A CRP extinction coefficient (mg/ml) of 1.95 was used to determine concentration. Next, the concentrated CRP was exhaustively dialyzed against 10 mM Tris-HCl-buffered saline, pH 7.2, containing 2 mM $CaCl_2$. This preparation produced a single Mr 23,000 band on SDS-PAGE electrophoresis and was more than 99% free of SAP, IgG and all other proteins tested for antigenically.

For the Q-Sepharose Fast Flow® column, 5 ml of the final concentrated CRP solution containing 5 mg of purified native CRP was diluted in about 30 ml of 10 mM Tris-HCl, pH 7.4, and the resulting solution was loaded on the Q-Sepharose Fast Flow column at 6 ml per minute. Bound material was eluted with a linear NaCl gradient using 10 mM Tris-HCl, pH 7.4, containing 1M NaCl. $A_{280}$ was measured using the BioPilot® automated chromatography system.

B. mCRP Preparation

To make mCRP, purified native CRP, prepared as described above, at 1 mg/ml was incubated in 8M ultra-pure urea in the presence of 10 mM EDTA for one hour at 37° C. The urea was removed by dialysis into 10 mM sodium phosphate buffer (pH 7.4) or Tris-HCl buffer (pH 7.2) containing 0.015M sodium chloride. The mCRP was sterile filtered through a 0.2 micron filter (Gelman). Some of the sterile filtered mCRP was adjusted to physiologic ionic strength by adding sodium chloride to give a final concentration of 0.15M NaCl, and then incubated in an ice bath for 15 minutes. Before adjusting the ionic strength, the mCRP is soluble. After adjusting the ionic strength, the majority of mCRP self-aggregates into a suspension.

Example 2
Preparation of a Mutant Subunit of mCRP

This example describes the preparation of a recombinant DNA molecule coding for a mutant human CRP subunit in which the two cysteine residues at positions 36 and 97 (using the numbering system of Woo, et al., *J. Biol. Chem.*, 260, 13384–13388 (1985)) have been replaced with alanine residues. This example also describes the preparation of vectors containing the recombinant DNA molecule operatively linked to expression control sequences and the expression of the mutant CRP subunits in *Escherichia coli*.

A. Replacement Of The Codons For Cysteine-36 And Cysteine-97 In The CRP Coding Sequence Using A Polymerase Chain Reaction Technique To replace codons for cysteine-36 and cysteine-97 in the coding sequence for mature human CRP subunits with codons for alanine, the method of Horton et al., *BioTechniques*, 8, 528–535 (1990) which is based on the polymerase chain reaction (PCR; Saiki et al., *Science*, 239, 487–491 (1988)) was used. Since two independent changes were desired, the process was modified to incorporate a total of five PCR reactions as illustrated in FIG. 1A. Table 1 shows the sequence of the oligonucleotides used as primers in the PCR reactions.

TABLE 1

| Number | Sequence | SEQ ID NO |
|---|---|---|
| 1 | 5'GGGCC*ATATG*CAGACAGACATGTCGAGG→3' | 1 |
|  | NdeI |  |
| 2 | 3'←TCGGAAGTGACACCGCGAAG5' | 2 |
| 3 | 5'CACTGTGGCGCTCCAC→3' | 3 |
|  | HhAI |  |
| 4 | 3'←GGTCATGTGTAGCGCTGTT5' | 4 |
| 5 | 5'CAC*ATCGCG*ACAAGCTG→3' | 5 |
|  | NruI |  |
| 6 | 3'←GGACTT*CCATGG*AGT*CTAGA*GCGG5' | 6 |
|  | KpnI    BglII |  |

*Italicized* bases indicate restriction enzyme recognition sites.
Bold bases indicate mutagenized codons and the initiation ATG codon.
Underlined bases are complementary to the CRP cDNA sequence.

As shown in FIG. 1A, the five reactions were: (1) Reaction of cDNA clone coding for preCRP with primers 1 and 2 to produce PCR product A; (2) Reaction of cDNA coding for preCRP with primers 3 and 4 to produce PCR product B; (3) Reaction of cDNA coding for preCRP with primers 5 and 6 to produce PCR product C; (4) Reaction of products A and B in the presence of primers 1 and 4 to produce PCR product D1; and (5) Reaction of products D1 and C in the presence of primers 1 and 6 to produce the final product D2. D2 was thought to code for the mature sequence of human CRP subunit (the presequence has been eliminated), except that there was an additional methionine at the N-terminus and cysteines 36 and 97 had been replaced by alanines. This was subsequently found not to be the case (see section F below).

The DNA coding for human preCRP used as the starting material for these PCR reactions was obtained by digestion of pCRP5 with EcoRI to yield linear (noncircular) DNA. A sample of plasmid pCRP5 was obtained from Drs. Bruce Dowton and Harvey Colten of Washington University School of Medicine, St. Louis, Mo. pCRP5 was isolated from a human liver cDNA library as described in Tucci et al., *J. Immunol.*, 131, 2416–19 (1983). The nucleotide sequence of the cDNA of pCRP5 and the amino acid sequence of the preCRP coded for by it are given in Woo, et al., *J. Biol. Chem.*, 260, 13384–13388 (1985). However, as described in detail in section F below, the cDNA of the pCRP5 sample obtained from Drs. Dowton and Colten was found to have a deletion in codon 47.

The PCR reactions were carried out using VENT polymerase (New England Biolabs) to minimize unwanted mutations due to misincorporation of bases, and the PCR reactions were done using 20 cycles, each cycle consisting of: 94° C. for 1 minute; 37° C., 42° C. or 60° C. for 1 minute (the annealing temperature depending on the sequence of the primers); and 74° C. for 3 minutes. Following the amplification steps, the reactants were further incubated at 74° C. for 5 minutes to complete the synthesis of double-stranded DNA. Each of the products was purified by agarose gel electrophoresis as described in Horton et al., supra. For the PCR reactions where the template consisted of two overlapping sequences (PCR D1 and PCR D2 in FIG. 1A), the reactants were incubated without primers for 4 cycles to allow the formation of full-length template before normal amplification was carried out.

PCR products were digested with restriction endonucleases HhaI and NruI (see Table 1) to confirm that the products incorporated the desired mutations.

B. Construction Of A Plasmid For The Overexpression Of The Mutant CRP Subunit

Figure 1B:
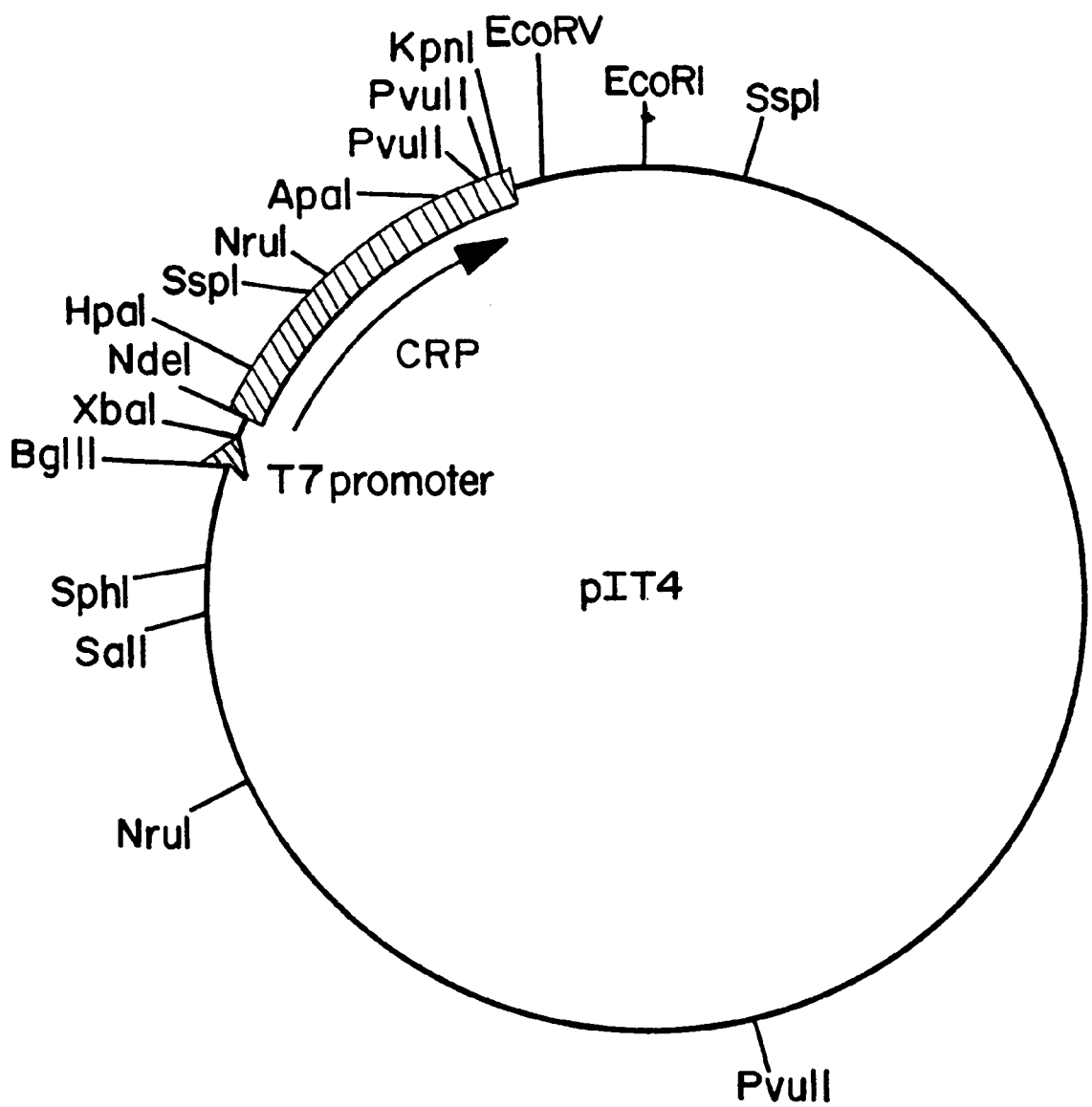
FIG. 1B is a restriction map of plasmid pIT4.

The final PCR product D2 was concentrated by filtration through a Centricon 30 apparatus (Amicon, Beverly, Mass.), and then treated with T4 polynucleotide kinase (Pharmacia, Piscataway, N.J.) and T4 DNA ligase (New England Biolabs, Inc.) as described in Denney et al., *Amplifications*, 4, 25–26 (1990). The resultant material was digested with NdeI and BglII to release the mutant CRP coding sequence, and the released coding sequence was ligated to the expression vector pETV which had been digested with NdeI and BamHI and treated with calf intestinal alkaline phosphatase (Promega, Madison, Wis.). The ligation mixture was used to transform *E. coli* DH5α (Gibco BRL Life Technologies, Inc.), and transformants were screened by minipreps performed as described in Birnboim et al., *Nucleic Acids Res.*, 7, 1513–1523 (1979) to identify the correct plasmid pIT4. A restriction map of pIT4 is provided in FIG. 1B. As shown in FIG. 1B, the mutant CRP coding sequence is under the control of the T7 promoter.

Figure 2A:
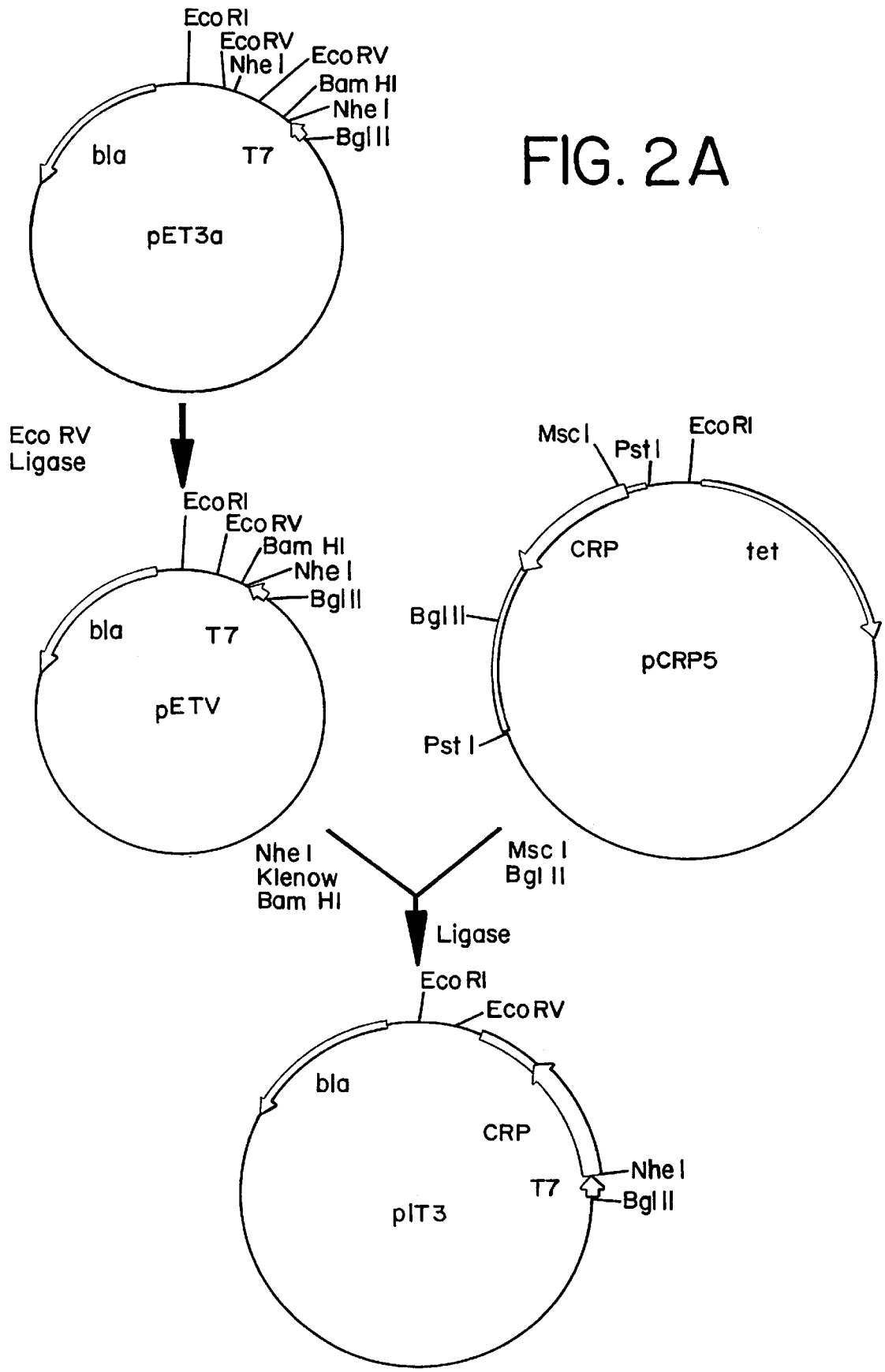

Plasmid pETV is a derivative of pET3a (see FIG. 2A). The preparation of pET3a is described in Rosenberg et al., *Gene*, 56, 125–135 (1987). Plasmid pET3a was obtained from Dr. W. Studier, Brookhaven National Laboratory, Upton N.Y. Plasmid pET3a has two NheI restriction enzyme sites (see FIG. 2B). One is located at the T7 gene 10 translation start site in which it was desired to insert the mutant CRP coding sequence. The second NheI site is located within a 190-bp fragment bounded by EcoRV sites. This second NheI site was eliminated by digestion with EcoRV and recircularizing the plasmid to yield pETV.

The predicted sequence of the junction between the expression system of pETV and the coding region for mutant CRP subunit in pIT4 was confirmed by DNA sequencing as follows. Plasmid pIT4 was digested with XbaI and KpnI, and the relevant fragment subcloned into M13mp18RF (Yanisch-Perron et al., *Gene*, 33, 103–119 (1985)). Single-stranded DNA was obtained from cultures carrying M13mp18RF and sequenced as described by Sanger et al., *J. Mol. Biol.*, 94, 441–558 (1975) using an Applied Biosystems Model 370A Automated DNA Sequencer.

C. Expression And Purification Of The Mutant CRP Subunit Produced By pIT4

Plasmid pIT4 was used to transform *E. coli* BL21(DE3) (preparation described in Studier et al., *J. Mol. Biol.*, 189, 113–130 (1986)) which carries the phage T7 RNA polymerase gene under expression control of the lacUV5 operator and promoter. Competent *E. coli* BL21(DE3) was obtained from Novogen, Madison, Wis. Transformants were selected on LB medium (Miller, *Experiments In Molecular Genetics* (1972)) containing 50 µg/ml ampicillin.

Transformed cells were grown in M9ZB medium (Studier et al., *J. Mol. Biol.*, 189, 113–130 (1986)) containing 100 µg/ml ampicillin at 37° C. for small-scale experiments. Ten-liter cultures were grown in a New Brunswick Microgen SF-116 fermentor in 2YT medium (Miller, *Experiments In Molecular Genetics* (1972)) plus 0.4% (w/v) glucose and 100 μg/ml ampicillin at 37° C. with aeration using compressed air at a rate of 10 liters per minute.

Synthesis of the T7 RNA polymerase, and consequently of the mutant CRP subunit, was induced with 1 mM (final concentration) isopropyl-beta-D-thio-galactoside (IPTG; Boehringer Mannheim) when the cell density reached $OD_{600}=4$. The cells were harvested 3 hours after induction by rapidly mixing the culture with an equal volume of ice, concentrating the cells by filtration using a Millipore Pellicon apparatus equipped with a Durapore 0.5 μM membrane, and centrifuging the cells in a Beckman JA10 rotor at 10,000 rpm for 20 min.

The harvested cells were suspended in 20 mM Tris-HCl, pH 7.5, containing 5 mM EDTA (40 g in 500 ml) and disrupted by three passages through a Manton-Gaulin homogenizer at 10,000 psi. The extract was centrifuged in a Beckman JA10 rotor at 8,000 rpm for 20 min. at 2° C. The pellet containing the insoluble mutant CRP subunits was washed twice with 20 ml of the same buffer containing 0.5% (v/v) Triton X-100 (Bio-Rad), followed by centrifugation in a JA18 rotor at 9,000 rpm for 20 min. to remove the soluble material.

About 50–100 mg of the final pellet was dissolved in 6M Guanidinium-HCl (J. T. Baker, Phillipsburg, N.J.) in 15 mM Tris-HCl, 10 mM EDTA buffer (pH 7.2). Insoluble materials were removed by centrifugation and discarded. Soluble materials were filtered through 0.8/0.2 micron filters (Gelman) and were made 28% ammonium sulfate by adding the appropriate percentage of saturated (100%) ammonium sulfate solution (Sigma Chemical Co., St. Louis, Mo.). Pellet was collected by centrifugation and washed in Tris-buffered saline (pH 7.4). Pellet was then dissolved at 1.4 mg/ml in 8M urea, 25 mM acetate buffer (pH 4.0) and was loaded onto a S-Sepharose-FF® cation exchange column (Pharmacia) equilibrated with 6M urea, 25 mM acetate buffer (pH 4.0). Loosely bound contaminating materials were removed by washing the column with 6M urea, 25 mM acetate buffer (pH 4.0) containing 0.5M sodium chloride. The column was reequilibrated with the above buffer lacking sodium chloride. Bound mutant recombinant-CRP ("mutant rCRP") was eluted using 6M Guanidinium-HCl in 25 mM acetate buffer (pH 4.0). Absorbance at 280 nm was measured using a BioPilot automated chromatography system (Pharmacia), and an elution profile obtained.

Eluted mutant rCRP was immediately applied to a SUPERDEX 200®, spherical composite of cross-linked agarose and dextran, Pharmacia Biotech Inc., Piscataway, N.J. molecular sieve column (Pharmacia) equilibrated in 4M urea, 3M Guanidinium-HCl, 25 mM acetate buffer (pH 4.0). Protein was passed through this column at a rate of 30.5 cm/hr. Chromatographed proteins were separated and collected based on absorbance at 280 nm using the automated BioPilot® Chromatography System (Pharmacia). Protein fractions containing mutant rCRP were sterile filtered through 0.8/0.2 micron filters (Gelman), pooled, and dialyzed into 25 mM Tris-HCl, 0.015M NaCl (pH 7.4).

D. Characterization Of The Fractions Eluted From The SUPERDEX 200®, Spherical Composite Of Cross-linked Agarose And Dextran, Pharmacia Biotech Inc., Piscataway, N.J.

The peaks from the SUPERDEX 200®, spherical composite of cross-linked agarose and dextran, Pharmacia Biotech Inc., Piscataway, N.J. column were analyzed by dot blot, Western blot, SDS-PAGE and ELISA. Mutant rCRP inclusion body preparations were sometimes also tested. Native CRP and mCRP were sometimes used as controls. The preparation of all of these materials is described in the previous section.

1. Dot Blot Assays

Following a modification of the procedure of Zhang, *J. Immunol.*, 138:575 (1987), nitrocellulose membranes (Schleicher & Schuell, Keene, N.H.) were pre-soaked in TBS (25 mM Tris-HCl, 0.15M NaCl, pH 7.4) for 30 min., and excess buffer was removed with filter paper. The membranes were then fitted into a Bio-Dot® microfiltration apparatus (Bio-Rad). Aliquots (50 μl) of the various test proteins at 5 μg/ml were dotted onto the membrane, incubated overnight at 4° C., and then vacuum-filtered to remove all of the liquid from the wells. Blocking solution (100 μl of 1% BSA in TBS) was added to the wells and incubated for 30 min. at room temperature (RT), and vacuum-filtered through the membrane. The wells were washed three times with TBS containing 1% BSA and 0.05% Tween 20 (TBS washing buffer). Mouse monoclonal antibody 3H12 or other class III or class IV monoclonal antibodies (U.S. Pat. No. 5,272,257) and goat polyclonal anti-neo-CRP antiserum were added and incubated for 30 min. at RT followed by washing. Monoclonal antibody specific for mCRP was used unlabeled, and the blots were developed by adding rabbit anti-mouse IgG F(ab')$_2$ labeled with horseradish peroxidase (Southern Biotechnology Associates, Birmingham, Ala.), incubating for 30 min. at RT, adding peroxidase substrate 4-chloro-2-naphthol (Bio-Rad) in 10 mM Tris-HCl, 0.15M NaCl, containing methanol and $H_2O_2$ prepared as directed (Bio-Rad), and incubating for 30 min. at RT to allow for color development. Polyclonal anti-neo-CRP was labeled with horseradish peroxidase, and the blots were developed by adding 4-chloro-2-naphthol followed by an incubation for 30 min. at RT for color development.

Monoclonal antibody 3H12 is an IgG antibody specific for an antigenic determinant found on mCRP but not on native CRP. Its preparation and properties are described in U.S. Pat. No. 5,272,257 and in Ying et al., *J. Immunol.*, 143:221–228 (1989). Anti-neo-CRP polyclonal antiserum is an antiserum prepared by immunizing a goat with mCRP in complete Freund's adjuvant and then affinity-purifying the harvested antiserum by passing it over a column substituted with strongly bound mCRP. The resulting affinity-purified anti-neo-CRP antiserum was predominantly reactive for the neo-CRP antigenicity expressed by mCRP but not by native CRP. Polyclonal anti-neo-CRP was labelled with horseradish peroxidase as described in Potempa et al., *Mol. Immunol.*, 24:531–541 (1987).

The dot blots showed that mCRP and mutant rCRP reacted with monoclonal antibody 3H12 and polyclonal anti-neo-CRP-HRP, indicating that all of these materials express antigenic determinants found on mCRP but not on native CRP. Native CRP did not react with antibodies 3H12 and anti-neo-CRP-HRP as expected.

2. Western Blot

The peaks were also analyzed by Western blot. To perform the Western blot, 5–10 μl of the peak concentrates were electrophoresed on 12% SDS-PAGE gels under reducing and non-reducing conditions. After electrophoresis, protein was transferred to a nitrocellulose membrane using the JKA Biotech (Denmark) Semidry Electroblotter. The remainder of the procedure was the same as described above for the dot blot, except that three mouse mAbs (3H12, 2C10 and 8C10) were used. The color was developed as described in the previous section for mAb 3H12.

Monoclonal antibody 3H12 is described above. Monoclonal antibody 8C10 reacts with a determinant found only on mCRP, whereas mAb 2C10 reacts with a determinant found on both native CRP and mCRP. The preparation and properties of mAbs 2C10 and 8C10 are described in U.S. Pat. No. 5,272,257; Ying et al., *J. Immunol.*, 143:221–228 (1989); Ying et al., *Mol. Immunol.*, 29:677 (1992).

The Western blot results showed that mCRP and mutant rCRP reacted with all three mabs, indicating that all of these materials express antigenic determinants found on mCRP. Native CRP reacted with mAb 2C10, but not with mAbs 3H12 and 8C10, confirming that this material is native CRP and that the antibodies were reacting as expected.

The Western blot results also showed that the predominant material present in mutant rCRP (the major peak obtained when the mutant CRP subunit was chromatographed on SUPERDEX 200®, spherical composite of cross-linked agarose and dextran, Pharmacia Biotech Inc., Piscataway, N.J. was free, monomeric subunits. Thus, mutant rCRP produced by replacing the cysteine residues in a CRP subunit, was processed to give a pure, well-defined product.

3. SDS-PAGE

Figure 3:
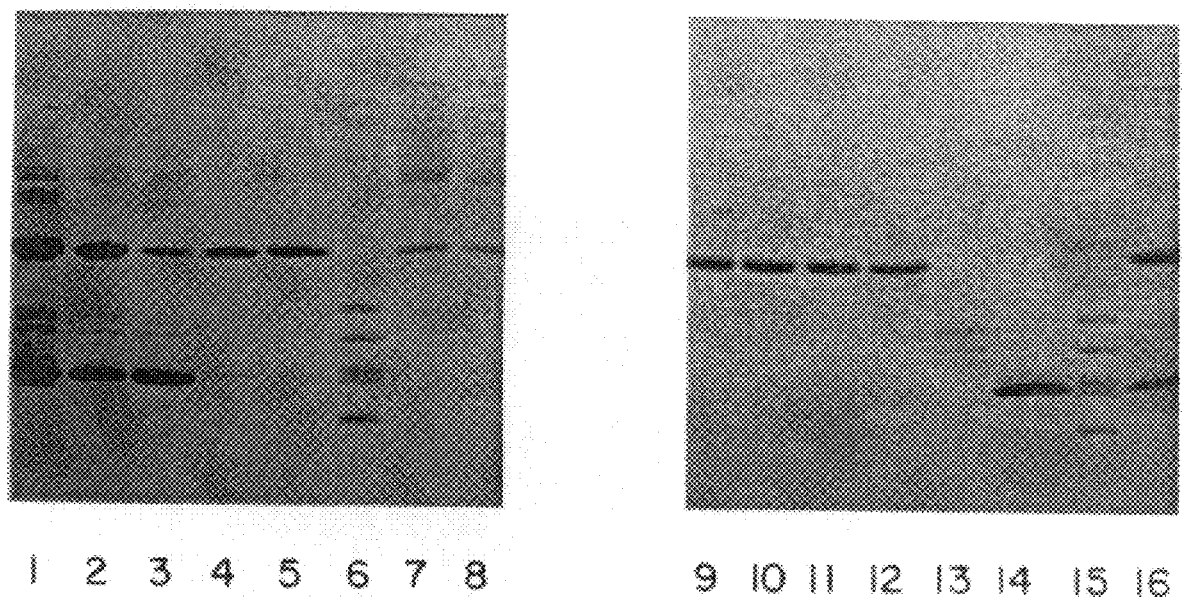
FIG. 3 is a photograph of an SDS-PAGE gel which includes samples of recombinant mutant protein.

The peak concentrates were run on PHASTGEL® polyacrylamide gels, Pharmacia Biotech Inc., Piscataway, N.J. SDS-PAGE gels (Pharmacia). A gradient of 8–25% gradient acrylamide was used. After the electrophoresis was complete, the gels were stained with Coomassie blue. The results are shown in FIG. 3.

Lane 1 contains the mutant rCRP inclusion body preparation. Note that there are two predominant bands, including one at approximately the same position as the single mCRP band (Mr of about 23,000). This band was verified by Western blot analysis to be antigenically reactive with antibodies specific for mCRP determinants. The second predominant band of Mr about 7000 was verified by Western blot to also be antigenically reactive with antibodies specific for mCRP determinants.

Lanes 2 and 16 contain washed inclusion bodies. Lane 3 contains the sodium chloride wash from the S-Sepharose FF® cation exchange column. Lanes 4 and 5 contain the Guanidinium-HCl eluate from the cation exchange column. Note that only one major band was obtained having a molecular weight of approximately 23,000, the molecular weight of the desired free mutant CRP subunits. As can be seen, there are many fewer bands as compared to the mutant rCRP inclusion body preparation (lanes 1 and 2), and the amounts of remaining contaminants, especially the one predominant contaminant having Mr of approximately 7000 have been substantially reduced. Thus, the purity of the mutant CRP subunit was greatly improved by the single-step S-Sepharose-FF® chromatography procedure.

Lanes 6 and 15 contain molecular weight standard protein bands.

Lanes 7 and 8 contain large molecular weight aggregate proteins separated from mutant rCRP-cation exchange protein by SUPERDEX 200®, spherical composite of cross-linked agarose and dextran, Pharmacia Biotech Inc., Piscataway, N.J. gel filtration chromatography. Note that some protein of Mr 23,000 is recovered in these fractions. These proteins are discarded.

Lanes 9, 10 and 11 contain highly-purified mutant rCRP. By Western blot analysis, this band reacted with antibodies specific for mCRP. No other bands of protein were visualized in these samples using the Western blot technique. Lane 12 contains a fraction of mutant rCRP contaminated with smaller Mr proteins. Such fractions, even though they contain substantial amounts of mutant rCRP, are discarded. Lane 13 contains small contaminating proteins which are discarded. Lane 14 contains small molecular weight fractions of mutant rCRP samples chromatographed on SUPERDEX 200®, spherical composite of cross-linked agarose and dextran, Pharmacia Biotech Inc., Piscataway, N.J. This sample reacted with antibodies specific for mCRP by Western blot. Thus, these proteins contain a fragment of mutant rCRP molecule.

4. ELISA

Finally, an ELISA was performed to detect binding of antibodies specific for native CRP and mCRP to the materials in the peaks eluted from the SUPERDEX 200®, spherical composite of cross-linked agarose and dextran, Pharmacia Biotech Inc., Piscataway, N.J. column. A direct binding ELISA was used for mCRP and mutant rCRP preparations. A ligand capture ELISA was used for native CRP preparations.

In the direct ELISA, 100 $\mu$l of each test protein (5 $\mu$g/ml) in 50 mM sodium bicarbonate buffer (pH 9.5) were placed in the wells of Nunc polystyrene plates (Scientific Supply, Shiller Park, Ill.) and incubated for 2 hours at 37° C. or 4° C. overnight. The wells were blocked with TBS (25 mM Tris-HCl, 0.15M NaCl, pH 7.4) containing 1% bovine serum albumin (BSA) (TBS-A) for 60–120 min. at 37° C. The wells were washed with TBS containing 0.05% Tween 20 (TBS-wash buffer). Antibodies were serially diluted with TBS-A, and 100 $\mu$l aliquots were added to the wells and incubated for 60 min. at 37° C., followed by washing. Peroxidase-conjugated rabbit anti-mouse IgG (Southern Biotech) in TBS-A was added to the wells for 60 min. at 37° C. After washing, 100 $\mu$l ABTS substrate (2-2'azino-bis 3-ethylbenzylthiazoline-6-sulfonic acid, Sigma Chemical Co.) were added per well and incubated for about 5–15 min. at RT. Plates were read at an absorbance of 414 nm on a Titertek® multiskan plate reader (Flow Laboratories, Helsinki, Finland).

For the ligand capture ELISA, plates were incubated with 100 $\mu$l/well of PC-KLH (5 $\mu$g/ml) in bicarbonate buffer for 2 hr. at 37° C. or overnight at 4° C. Wells were blocked with TBS-A containing 2 mM $CaCl_2$ as described above. After blocking, 100 $\mu$l/well of native CRP (5 $\mu$g/ml) in TBS-A containing 2 mM $CaCl_2$ were added and incubated for 60 min. at 37° C. After washing, the rest of the assay was performed as described above, except that 2 mM $CaCl_2$ was included in all buffers. PC-KLH is phosphorylcholine (PC) substituted Keyhole Limpet hemocyanin (KLH). It was prepared by incubating KLH (Sigma Chemical Co.) with paranitrophenyl phosphorylcholine (Sigma Chemical Co.) diazotized as described by Chesebro and Metzger, *Biochemistry*, 11:766 (1972). The final derivatization resulted in 28–52 moles PC per Mr of $1 \times 10^5$ KLH.

Figure 4A:
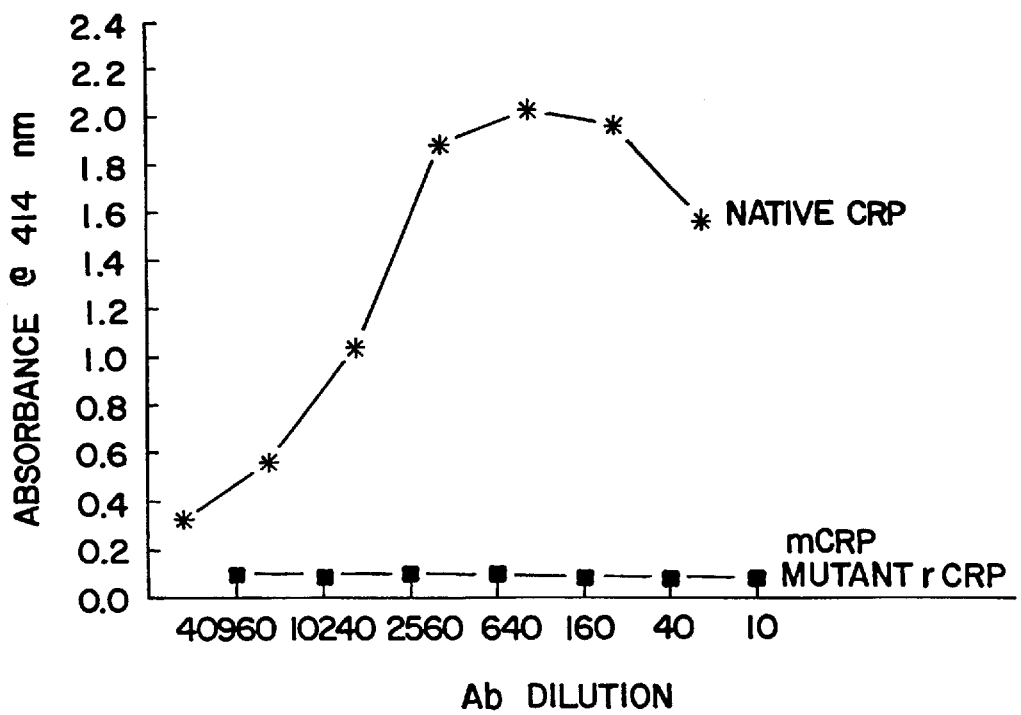
FIGS. 4A–4C are graphs of the results of ELISA assays to detect the presence of native CRP and mCRP antigenic determinants on recombinant mutant protein.
Figure 4B:
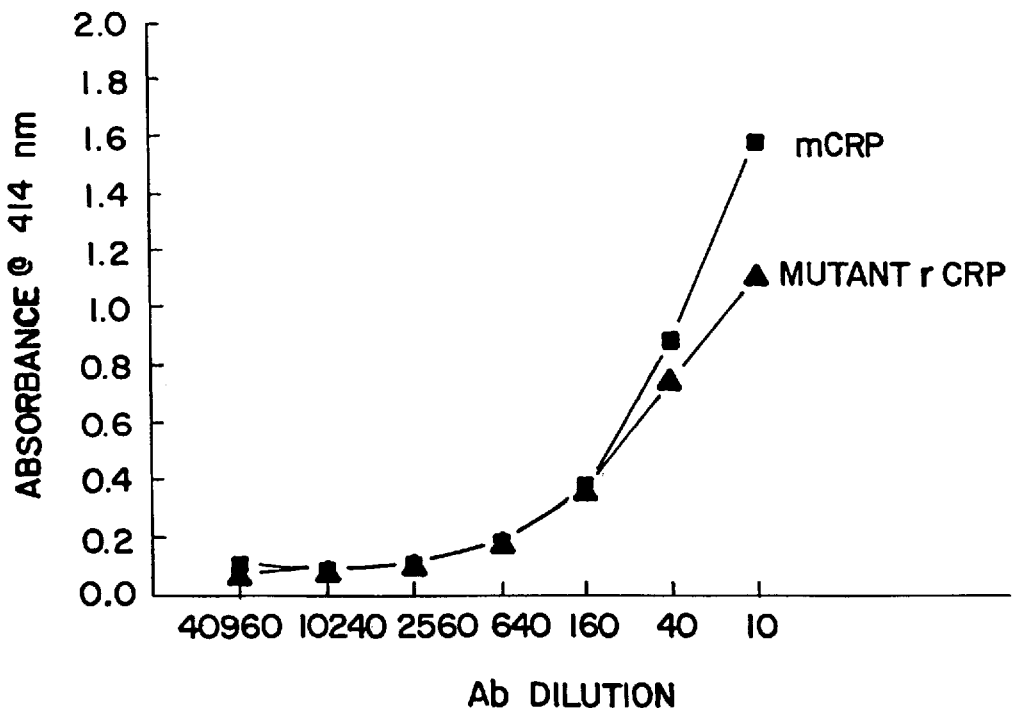
Figure 4C:
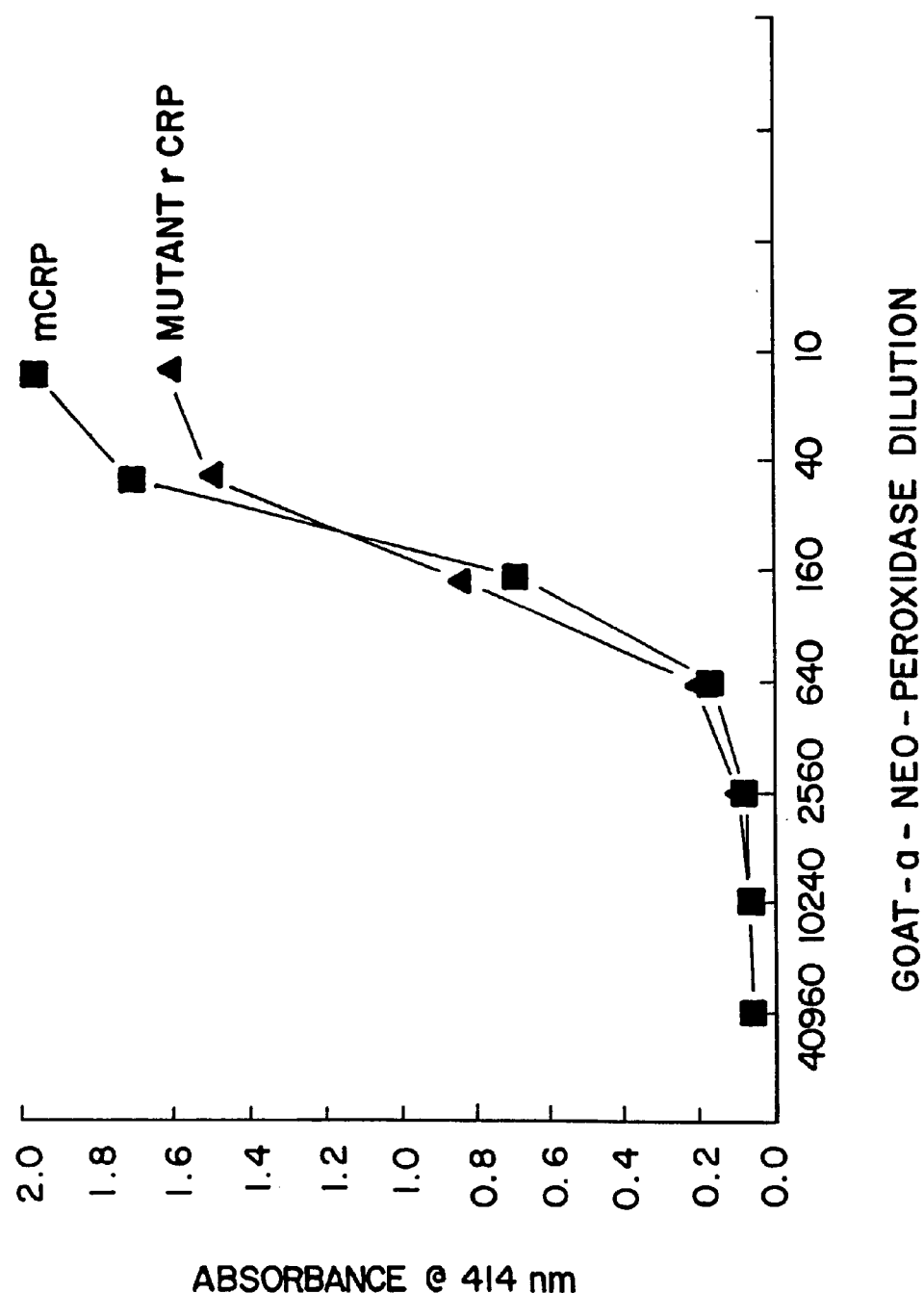

The results of these ELISAs are shown in FIGS. 4A–C. FIG. 4A shows the reactivity of mCRP, mutant rCRP and native CRP with mAb 1D6. As expected mAb 1D6 reacted with native CRP but not with mCRP. Also, mutant rCRP reacted like mCRP and unlike native CRP, indicating that the native CRP epitope recognized by mAb 1D6 is not expressed on mutant rCRP.

FIG. 4B shows the reactivity of mCRP and mutant rCRP with mAb 3H12. Monoclonal antibody 3H12 is specific for an antigenic determinant found on the C-terminal octapeptide of mCRP. As expected mAb 3H12 reacted with mCRP. As shown, mutant rCRP, like mCRP, reacted with mAb 3H12, indicating that the neo-CRP epitope recognized by mAb 3H12 is also expressed on mutant rCRP.

FIG. 4C shows the reactivity of mCRP and mutant rCRP with goat anti-neo-CRP-HRP polyclonal antiserum. As shown, mutant rCRP reacted with goat anti-neo-CRP-HRP in a manner similar to mCRP. This suggests that the recombinant mutant protein produced by pIT4 is antigenically very similar to mCRP.

F. Discovery Of A Deletion In Codon 47 And Preparation Of A Clone Having The Correct Sequence Although mutant rCRP expression was obtained using *E. coli* BL21(DE3), the level of mutant rCRP produced was considerably lower than has been reported in the literature for other proteins using the T7 RNA polymerase system employed in *E. coli* BL21(DE3). Possible reasons for this low level of expression were explored, and it was noted that a fragment of ~7000 Mr was consistently observed as a product (see FIG. 3). Western Blot analysis showed that this fragment was related to mCRP antigenically (see section D3 above).

N-terminal sequence analysis of the purified fragment confirmed that the fragment contained the expected CRP sequence from residues 1 to 6. The N-terminal sequence analysis was performed by Analytical Biotechnology Services (Boston, Mass.) using automated Edman degradation on an Applied Biosystems Model 477A protein sequencer. The Mr 7000 fragment used for the N-terminal sequencing was purified as follows. The concentration of protein in an inclusion body suspension was estimated using the Bicinchoninic Acid protein assay (Pierce Biochemicals). Inclusion body protein was then solubilized in 6M guanidine HCl (GuHCl; J. T. Baker Inc.), 15 mM Tris-Cl, pH 7.2, 10 mM EDTA at a concentration of 4 mg protein/ml. Ammonium sulfate was added to 28% saturation, and the precipitated protein collected by centrifugation (10 minutes at 12,000 rpm in a Sorvall GSA rotor). The resulting pellet was washed with TBS (10 mM Tris-Cl, pH 7.4, containing 0.15M NaCl) and subsequently dissolved in 8M urea, 25 mM sodium acetate, pH 4.0, at a concentration of approximately 1 mg protein/ml as judged by absorbance at 280 nm. This material was passed over an S-Sepharose Fast Flow column (Pharmacia) equilibrated with 6M urea, 25 mM sodium acetate, pH 4.0. The column was then developed with a four-column volume gradient of 0–0.25M NaCl in the equilibration buffer (6M urea, 25 mM sodium acetate, pH 4.0). The fragment eluted at approximately 0.24M NaCl. Fractions containing the fragment were pooled and concentrated by precipitation with 50% saturated ammonium sulfate. The precipitate was collected by centrifugation as described above and dissolved in equilibration buffer. The dissolved precipitate was again passed over an S-Sepharose Fast Flow column as described above, except that elution was performed with a 0–0.8M NaCl gradient.

The size of the fragment and the quantity produced were very consistent from batch to batch. Furthermore, there was little evidence of other fragments, suggesting that the 7000 Mr fragment resulted from incomplete mRNA or protein synthesis rather than from proteolytic degradation.

Accordingly, the DNA coding for the mutant rCRP was sequenced. To do so, the coding sequence was excised from pIT4 using XbaI and KpnI and ligated into pBluescript KS (Stratagene Inc.) previously digested with the same enzymes. The subcloned DNA was sequenced on an Applied Biosystems Sequenator by the dideoxy chain termination method using standard M13-based primers. The DNA sequences of two independent isolates revealed two differences with respect to the published Woo et al. sequence (Woo et al., *J. Biol. Chem.*, 260, 13384–13388 (1985)). First, there was a synonymous substitution (G to A) in the wobble position of codon 152 (as noted above, the numbering system of Woo et al., *J. Biol. Chem.*, 260, 13384–13388 (1985) is being used; this would actually be the 153rd codon of the CRP coding sequence of pIT4 since an ATG start codon was added at the 3' end of the coding sequence (see section A above). Second, there was a missing T at codon 47. The missing base in is in a GC-rich region, and it was initially thought that the absence of this T from the sequence was due to compression, a common sequencing artifact.

However, the results obtained from C-terminal sequence analysis of the 7000 Mr fragment were consistent with the DNA sequence data. C-terminal sequencing of the purified fragment (prepared as described above) was performed by Analytical Biotechnology Services. Briefly, the fragment was digested with carboxypeptidase Y at a ratio of 5 μg enzyme per 10 nmol protein (based on an estimated molecular weight of 7000). The mixture was incubated at 37° C., and 0.5 nmol aliquots were removed at 0, 30, 60 and 180 minutes and frozen at –20° C. Each aliquot was then subjected to amino acid analysis using the Waters PICO-TAG system. The following residues were released in roughly equal amounts after digestion of the fragment with carboxypeptidase Y: Ser, Tyr, Phe, Gly, Leu, Arg, and Ile. While these amino acids could possibly be assigned to the CRP sequence ending at Phe 52:

Leu Ser Ser Thr Arg Gly Tyr Ser Ile Phe
                          5                     10
                                                        SEQ ID NO:11, the fit is ambiguous because Thr was not detected after the carboxypeptidase Y digestion. In contrast, a missing base at codon 47 would introduce a frameshift resulting in a termination codon at position 71. The predicted sequence of the C terminus of this polypeptide would be Ser Tyr Phe Gly Leu Arg Ile SEQ ID NO:12,
                 5 which is a precise fit to the C-terminal sequence data for the fragment.

Deletion of T at codon 47 would also fortuitously introduce a novel restriction site into the DNA by changing the base sequence from CCCGTGG to CCCGGG, the latter being the recognition sequence for the enzyme SmaI. Analytical digests were therefore performed on pIT4 and pCRP5 by digesting 50–100 ng of each plasmid for 2–4 hours at 37° C. with EcoRI, SmaI, KpnI or SmaI and KpnI. The digestion products were separated on 1% agarose gels and visualized with ethidium bromide. Both plasmids were digested with SmaI yielding fragments of the sizes expected if the T in codon 47 were missing. These results further confirm the results of the DNA sequence analysis. These results also demonstrate that the deletion had occurred in the original plasmid pCRP5 and was not a result of the subcloning process described in section A above. No undigested DNA was detectable in any of the plasmid digests.

Finally, a sample of the purified 7000 Mr fragment (purified as described above) was submitted to Analytical Biotechnology Services for complete amino acid composition analysis. Briefly, the protein sample was hydrolyzed in 6N HCl and derivatized with phenylisothiocyanate. The phenylthiohydantoin-amino acids were detected by high performance liquid chromatography (HPLC). Once again, the results confirmed that there was a base deletion in codon 47 which introduced a frameshift leading to premature termination of protein synthesis at codon 71.

The analysis of both the plasmid DNA and the Mr 7000 fragment, thus, provided convincing evidence that a base deletion in codon 47 was causing premature termination of translation, and that the deletion had originated in plasmid pCRP5. However, full-length mutant rCRP subunits were being made (see FIG. 3).

A possible explanation for the synthesis of the full-length subunits was suggested by a report in the literature [Tenchini et al., *Inflammation*, 16, 93 (1992)]. Tenchini et al. describe a human CRP cDNA clone which had been isolated and sequenced. It had the base deletion in question in codon 47, but also contained a single base insertion at codon 64 (see Table 2 below). Since the insertion occurs before the termination codon introduced by the deletion, the proper reading frame is restored before protein synthesis is terminated. The net result is a sixteen-amino acid segment of out-of-frame sequence in the middle of the protein.

This segment differs greatly in amino acid composition from the known CRP sequence, so amino acid analysis was performed on the purified mutant rCRP produced by pIT4. The protein was purified as follows. Mutant rCRP was purified using a two-step column procedure. Inclusion body protein was solubilized, fractionated with ammonium sulfate and dissolved in urea as described above for the Mr 7000 fragment. This material was then applied to an S-Sepharose Fast Flow cation exchange column. The column was developed with a 0–0.25M NaCl gradient in 6M urea, 25 mM sodium acetate, pH 4.0, to removed impurities. After the NaCl concentration was decreased to 0, the mutant rCRP was eluted with 8M GuHCl, 25 mM sodium acetate, pH 4.0. The GuHCl eluate was then applied to a SUPERDEX 200®, spherical composite of cross-linked agarose and dextran, Pharmacia Biotech Inc., Piscataway, N.J. gel filtration column (Pharmacia) which had been equilibrated with 3M GuHCl, 4M urea in 25 mM sodium acetate, pH 4.0. The purified protein was submitted to Analytical Biotechnology Services for complete amino acid composition analysis. The results were inconclusive.

Several additional experiments designed to detect the presence of an inserted base in codon 64 were negative.

mutations occurring, for example, when an aminoacyl-tRNA is limiting. See, e.g., Weiss et al., *EMBO J.*, 7, 1503–1507 (1988); Tsuchihashi et al., *Proc. Natl. Acad. Sci.*, 87, 2516–20 (1990); Gallant et ale, *J. Mol. Biol.*, 223, 31–40 (1992); Sipley et al., *Proc. Natl. Acad. Sci.*, 90, 2315–19 (1993); and Lindsley et al., *Proc. Natl. Acad. Sci.*, 90, 5469–73 (1993). In the present case, the ribosomal frameshift must occur between the T deletion in codon 47 and the stop codon 71 to restore the reading frame and obtain a

TABLE 2

Amino acid sequence of CRP between residues 46–72 and corresponding DNA sequence:
```
                    10                                                                      SEQ ID
NO:13
Thr Arg Gly Tyr Ser Ile Phe Ser-
  Tyr Ala Thr Lys Arg Gln Asp Asn Glu Ile Leu Ile Phe Trp Ser Lys Asp Ile Gly
            5               10              15          20                    25

ACC CG
T GGG TAC AGT ATT TTC TCG TAT GCC ACC AAG AGA CAA GAC AAT GAG ATT CTC ATA TTT TGG TCT AAG GAT ATA GGA   81
                                                                            SEQ ID NO:14
```

Possible amino acid sequence of Mr 7000 fragment between residues 46–72 assuming deletion only and corresponding DNA sequence:
```
                                                                                           SEQ ID NO:15
Thr Arg Gly Thr Val Phe Ser Arg Met Pro Pro Arg Asp Lys Thr Met Arg Phe Ser Tyr Phe Gly Leu Arg Ile STOP
            5               10              15          20                    25

ACC CGG GGT ACA GTA TTT TCT CGT ATG C-
CA CCA AGA GAC AAG ACA ATG AGA TTC TCA TAT TTT GGT CTA AGG ATA TAG GA    80
                                                                    SEQ ID NO:16
```

Tenchini et al. amino acid sequence between residues 46–72 and corresponding DNA sequence:
```
                                                                                           SEQ ID NO:17
Thr Arg Gly Thr Val Phe Ser Arg Met-
  Pro Pro Arg Asp Lys Thr Met Arg Phe Phe Ile Phe Trp Ser Lys Asp Ile Gly
            5               10              15          20                    25

ACC CGG GGT ACA GTA TTT TCT CGT ATG CCA CCA AGA GAC AAG ACA ATG AGA TTC T
TC ATA TTT TGG TCT AAG GAT ATA GGA 81
                                                                    SEQ ID NO:18
```

The nucleotides deleted or inserted are underlined when present. Amino acids in boldface type are those differing from the sequence of CRP.

full-length product. The amino acid sequence of the full-length rCRP coded for by codons 47–71 has been deduced (see section J below).

Moreover, the initial DNA sequence analysis of plasmid pIT4 had not detected the insertion of a base in codon 64 (see above). The combined experimental results, therefore, supported the conclusion that there is a base deletion in codon 47 and no base insertion prior to stop codon 71.

It is highly unlikely that the full-length rCRP subunits result from occasional read-through of the stop codon 71, since the frameshift due to the deletion in codon 47 introduces a total of nine termination codons into the mRNA. Even if it were possible for the ribosomes to read through all nine stop codons, the frequency of the event should decrease as the number of missed codons increases. This would generate a predictable ladder of products, with the largest being present in the lowest abundance. In contrast, only two predominant species have been observed, the 7000 Mr fragment encoded by the plasmid and the full-length subunit (see FIG. 3).

Many explanations as to the source of the full-length rCRP have been eliminated, and it is now believed that it results from a ribosomal frameshift whereby the ribosome shifts one or two bases during translation of the mRNA so that the proper reading frame is restored. There are many documented examples of such events occurring in *E. coli*, both as natural mechanisms for protein synthesis and as Clearly, the base deletion in codon 47 of the CRP coding sequence of pIT4 was preventing efficient expression of rCRP, and mutagenesis was necessary to correct the sequence. In addition, some other features of the CRP coding sequence were identified which could hinder rCRP expression. One of these is a potential stem-loop structure surrounding the site of the deletion. A second is poor codon usage. The mutagenesis, therefore, had three goals: 1) to reintroduce the missing base into codon 47; 2) to reduce the possibility of mRNA secondary structure; and 3) to replace codons infrequently used in *E. coli*.

The mutagenic primer was designed with those goals in mind. The target sequence for mutagenesis and the changes to be introduced are shown below. The bold letter indicates the base that was inserted into the site of the deletion (codon 47). The underlined codons (48 and 50) are others that were changed for purposes of increasing expression.

TARGET SEQUENCE: (SEQ ID NO:19)

CC TCG ACC CGG GGT ACA GTA TTT TCT CG  28

DESIRED CHANGES:

CC TCG ACC CGT <u>GGT</u> TAC <u>AGC</u> ATT TTC TCG  29    (SEQ ID NO:20)

Figure 12:
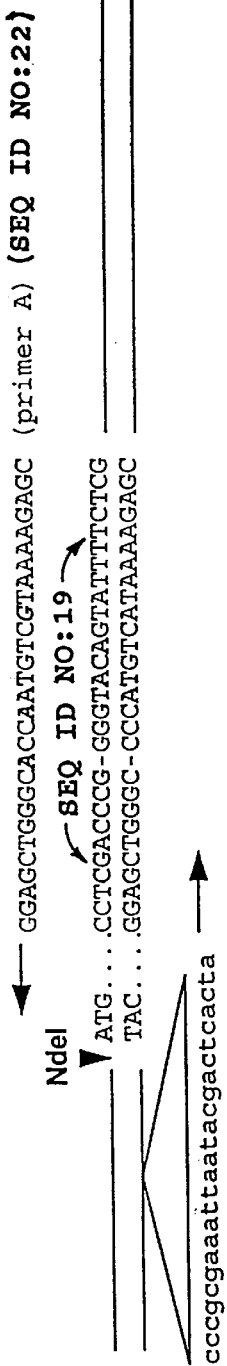
FIG. 12 is a diagram of a series of polymerase chain reactions.
Figure 12:
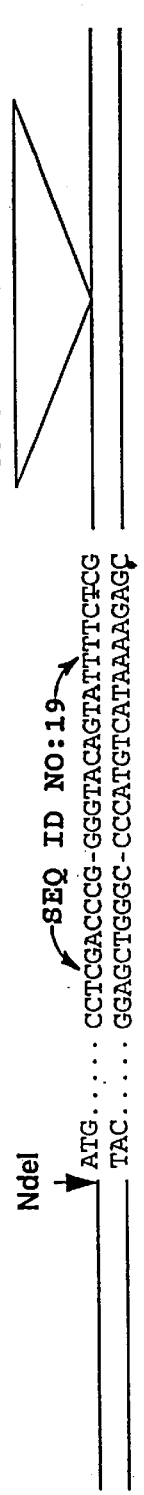
Figure 12:
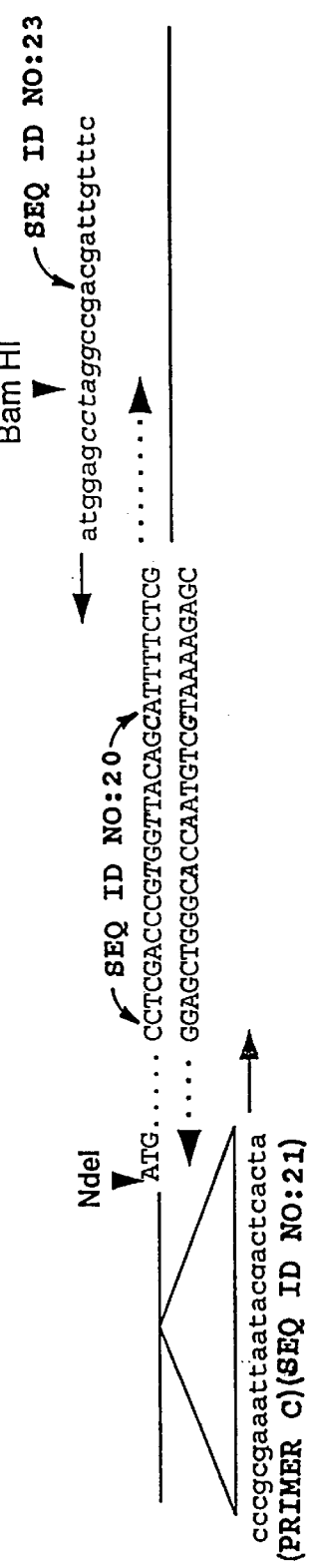

Gly 48:            Ser 50:
    change codon     change codon
    usage, weaken    usage
    2° structure Complementary oligonucleotide primers spanning the target sequence were synthesized by the phosphoramidite method on an Eppendorf Synostat-D synthesizer using Eppendorf reagents. The sequences of these primers are shown as A and B in Table 3 below. Two additional oligonucleotides (C and D) were synthesized for use as flanking primers. Their sequences and locations relative to the CRP sequence and a schematic diagram of each of the reactions performed are shown in FIG. 12.

The vector pETV and the final PCR product were digested with NdeI and BamHI. The fragments were gel-purified using GeneClean. The vector was then treated with calf intestinal alkaline phosphatase. Vector and insert were ligated, and the ligation mixture was used to transform *E. coli* BL21(DE3). Transformants were screened by minipreps performed as described in Sambrook et al., *Molecular Cloning: A Laboratory Manual* (2nd ed., 1989, Cold Spring Harbor Laboratory Press). Analytical digests were per-

TABLE 3

| Primer | Name | Length | Sequence | Note |
|---|---|---|---|---|
| C | Upstrm 1 | 25 | CCCGCGAAATTAATACGACTCACTA SEQ ID NO:21 | 5' flanking primer |
| B | SmaI upper | 29 | CCTCGACCCGTGGTTACAGCATTTTCTCG SEQ ID NO:20 | Muta-genic primer, puts T in and removes putative stem loop |
| A | SmaI lower | 29 | CGAGAAAATGCTGTAACCACGGGTCGAGG SEQ ID NO:22 | As above, but opposite strand |
| D | BamHI lower | 26 | CTTTGTTAGCAGCCGGATCCGAGGTA SEQ ID NO:23 | 3' flanking primer, intro-duces Bam HI site |

Reactions 1 and 2 illustrated in FIG. 12 employed 10 nmol of HindIII-linearized pIT4 as template, 10 pmol of each primer, 0.2 mM deoxynucleotide triphosphates (Pharmacia), 10 µl of 10× GeneAmp® reaction buffer (Perkin Elmer Cetus), and 2.5 units AmpliTaq® Taq DNA Polymerase (Perkin Elmer Cetus) in a total volume of 100 µl. Reaction buffer contains 50 mM KCl, 10 mM Tris-HCl (pH 8.3), 1.5 mM MgCl$_2$ and 0.001% (w/v) gelatin (final concentrations). Reactions were carried out in a DNA Thermal Cycler Model 480 from Perkin Elmer Cetus. Following a three-minute incubation at 94° C., the unit was programmed to run 20 cycles of 94° C., 1 min.; 50° C., 1 min.; 74° C., 1 min., ending with a 7 min. incubation at 72° C.

PCR products were purified on a vertical 1.6% agarose gel (1.5 mm thick) run in TAE (Tris Acetate/EDTA). Prior to casting the gel, plates, combs and spacers were soaked in 1N HCl for 30 minutes to guard against contamination. The appropriate bands were excised and the PCR products purified using a GeneClean II® kit (Bio101 Inc.) according to the manufacturer's instructions. The DNAs were eluted in a volume of 100 µl TE (10 mM Tris-Cl, pH 8.0, 1 mM EDTA). The yields of DNA were estimated from the prep gel.

A second set of PCR reactions was performed to splice together the first-round products, thus restoring the full-length coding sequence. Fifty ng of the 3' product and 20 ng of the 5' product were used as template, and 10 pmol each of primers A and B were used for amplification. Other conditions for the reactions were as in the first round. Four thermal cycles were performed prior to the addition of the primers to give a chance for the extension reaction to begin. After primers were added, the reactions were continued for another 20 cycles.

formed on the miniprep DNA using SmaI, NdeI and KpnI, NdeI and BamHI, and XbaI and HindIII. The products were separated on a 1% agarose gel and visualized with ethidium bromide. The DNA was demonstrated to be recombinant without the SmaI site. Subsequent sequence analysis confirmed that the CRP coding sequence had the expected sequence with all of the intended changes incorporated (see section G below); no errors in the sequence were detected. This plasmid was designated pIT10.

G. Preparation Of pIT13

Novagen, Inc. has developed several variants of the BL21(DE3) expression strain and of the pET3a vector used in the work described above. *E. coli* strain BLR(DE3) is identical to BL21(DE3), except that it is rec A⁻ and is therefore recombination deficient. Plasmid pET-24a(+) is a derivative of plasmid pET-3a in which the β-lactamase gene has been replaced with the gene conferring resistance to kanamycin. pET-24a(+) possesses the T7 promoter and has the lac operator sequence inserted between this promoter and the multiple cloning site. This vector is designed to provide a binding site for the lac repressor which will, in the absence of inducer, prevent transcription of the target gene.

Figure 13:
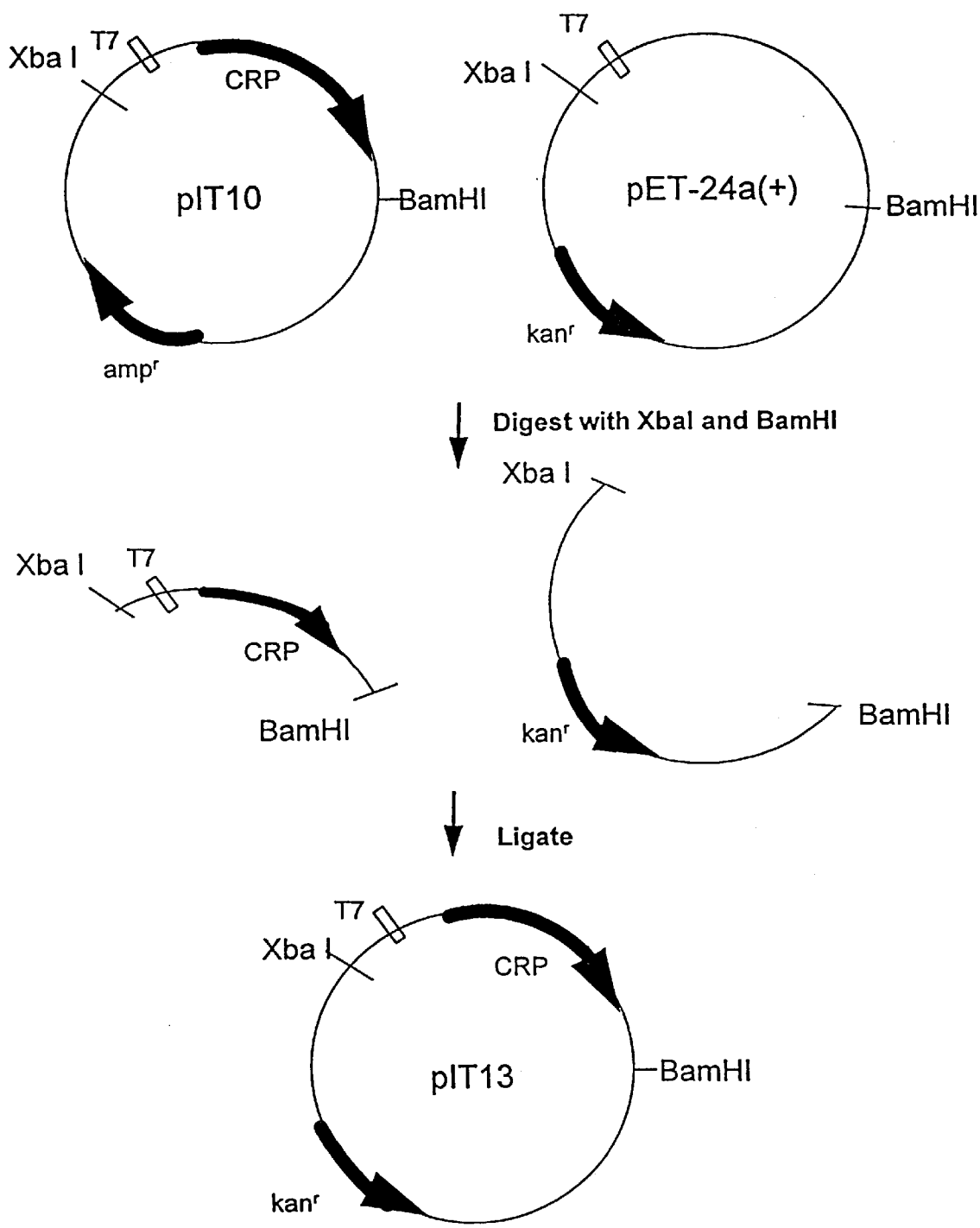
FIG. 13 illustrates the preparation of plasmid pIT13.

Since pET-24a(+) is a derivative of pET-3a, it has the XbaI and BamHI sites in the same positions as in the pETV vector used in the previous expression system. The mutant CRP coding sequence was therefore excised from pIT10 and cloned into pET-24a(+) digested with the same enzymes. The ligation mixture was transformed into *E. coli* DH5α cells, and transformants were selected by kanamycin resistance. Colonies were screened by restriction analysis of miniprep DNA (procedure described above in section F). Plasmid DNAs from confirmed recombinants were purified on cesium chloride gradients. One such recombinant was designated pIT13. The preparation of pIT13 is illustrated in FIG. 13.

Expression plasmid pIT13 was transformed into *E. coli* BLR(DE3). Transformants were selected by resistance to kanamycin. The combination of the kanamycin resistance marker and the T7-lac operator promoter help to ensure that the plasmid will remain under selection and that very little, if any, expression will occur prior to induction. The rec A⁻ genotype of the strain limits the possibility of recombination. Finally, the characteristics of the strain permit ease of handling on a production scale.

Culturing the pIT13/BLR(DE3) strain under the same conditions as the pIT10/BL21(DE3) strain (except for the type of antibiotic) resulted in the production of 12.5 g of inclusion body protein for the pIT13/BLR(DE3) strain as compared to 8.0 g for the pIT10/BL21(DE3) strain. Expression and purification of mutant rCRP from pIT13 in *E. coli* BLR(DE3) are further described in the next section.

Plasmid pIT13 was isolated from the *E. coli* BLR(DE3) expression strain and purified on a cesium chloride gradient. The CRP coding region was sequenced in the expression vector by the dideoxy chain terminator method of Sanger et al., *Proc. Nat'l. Acad. Sci. USA.* 74, 5463–5467 (1977) using Sequence version 2.0 (U.S. Biochemical Corp.) and $^{33}$P-dATP as the radiolabel.

Reaction products were separated on a 5% Hydrolink Long Ranger gel (AT Biochem Corp.). A sample of each reaction mixture was loaded and electrophoresed until the bromphenol blue dye marker reached the bottom of the gel (1st load). Identical samples were then applied to the remaining wells (2nd load) and electrophoresis continued until the bromphenol blue dye marker contained in the second set of samples reached the bottom of the gel. The gel was then dried and contacted with X-ray film for 2, 6.5, or 17 hours, and the sequence was read from the developed film.

The sequence determined by this procedure corresponded exactly to the coding sequence reported by Woo et al., *J. Biol. Chem.*, 260, 13384–88 (1985) with the following differences: the synonymous substitution in the wobble position of codon 152 (see section F above); the deletion of the leader sequence and introduction of an ATG codon for translation initiation; the substitution of a T for the G in the wobble position of codon 48; the substitution of a C for the T in the wobble position of codon 50; the substitution of a CGC codon (alanine) for the TGC codon for cysteine 36; and the substitution of a CGC codon (alanine) for the TGT codon for cysteine 97. It was, therefore, concluded that the predicted amino acid sequence of the mutant rCRP is identical to the sequence reported for unmutated CRP, except for the three changes purposefully factored into the molecule: 1) the N-terminal PCA amino acid of unmutated CRP is preceded by a formylated-methionine and is itself changed to glutamine; 2) cysteine residue number 36 is substituted with an alanine residue; and 3) cysteine residue number 97 is substituted with an alanine residue.

The DNA sequence results demonstrate that the genetic manipulations performed on the CRP coding sequence of pIT4 to correct the sequence and to obtain better expression of the mutant rCRP were performed correctly. No base additions, deletions, or substitutions were unintentionally introduced into the sequence.

H. Expression And Purification Of Mutant rCRP

The bacterial fermentations and the preparation of inclusion bodies were performed by Bio-Technical Resources (Manitowoc, Wis.) under aseptic conditions following the Good Laboratory Practices (GLP) guidelines of the Food and Drug Administration. Briefly, *E. coli* BLR(DE3) bearing the pIT13 plasmid was cultured in a 250 liter pilot fermentor (New Brunswick Scientific) as follows. *E. coli* BLR(DE3) cells were grown at 37° C. in a fourteen-liter New Brunswick Model FS614 fermentor in a medium containing NZ amine A® (enzymatic hydrolysate of casein; Quest International; 20 g/l), $(NH_4)_2SO_4$ (2 g/l), $KH_2PO_4$ (1.6 g/l), $Na_2HPO_4 \cdot 7H_2O$ (9.9 g/l), sodium citrate (0.65 g/l), $MgSO_4$ (0.24 g/l), glucose (22 g/l) and 50 µg/ml kanamycin. The culture was aerated using compressed air at 50 liters per minute. Synthesis of the mutant rCRP was induced with 1 mM IPTG (Gold Biotechnology Inc.) when the cell density reached $OD_{600}$=5. After a three-hour induction period, the cells were harvested by continuous flow centrifugation at 15,000 rpm in a Sharples model AS16VB tubular bowl centrifuge. The harvested cell paste was transferred into sterile plastic bags and frozen at –80° C.

The cell paste was thawed by placing the sealed plastic bags in a 45° C. water bath. The thawed cell paste was then suspended in cold breakage buffer (20 mM Tris-HCl, pH 7.6, 5 mM EDTA, 1 mM phenylmethyl sulfonyl fluoride (PMSF; Sigma Chemical Co.) at a ratio of 200 ml buffer per gram cell paste and processed in a sterile blender at low speed for 30–45 seconds. The homogeneous suspension was passed twice through a Nyro Soave homogenizer (equipped with a cell disruption valve) at a pressure of 500 bar. As it exited the homogenizer, the suspension was passed through a sterile cooling coil packed in an ice bath for cooling. It was then collected in a sterile covered container on ice.

This lysate was centrifuged at 12,000×g in a Beckman model J2-21 centrifuge for 10 minutes at 4° C. The pellet was resuspended in breakage buffer at 100 ml buffer per gram of initial cell paste. The suspension was then passed twice through the homogenizer, this time at 700 bar. The extract was centrifuged at 12,000×g for 25 minutes at 4° C. in a Beckman model J2-21 centrifuge to collect the inclusion body pellet.

The inclusion bodies were washed once with breakage buffer at a ratio of 150–200 ml buffer per 100 grams of initial cell paste by suspending the pellet in the buffer with a sterile glass rod and then centrifuging as described above. They were then washed three times with wash buffer (breakage buffer containing 0.5% Triton X-100 (Sigma Chemical Co.) at a ratio of 100–150 ml per 100 grams initial cell paste. The pellets were finally suspended in approximately 75 ml of breakage buffer per 100 grams of initial cell paste, aliquoted into sterile tubes, and frozen at –80° C. until further processing.

The concentration of protein in the inclusion body suspension was estimated using the Bicinchoninic acid protein assay (Pierce Chemical Co.) or by solubilizing the protein in 6M GuHCl and measuring the $A_{280}$ (using the extinction coefficient for pure mCRP; 1.95 $[mg/ml]^{-1}$). The inclusion bodies were then pelleted by centrifuging for 10 minutes at 12,000 rpm in a Sorvall GSA rotor. The supernatant was discarded, and the pellet was dissolved in a solution of 6M GuHCl in 25 mM Tris, pH 8 (6M GuHCl/Tris), to a concentration of between 5–10 mg protein/ml. The concentration of solubilized protein was determined by measuring the $A_{280}$ of a diluted sample. The inclusion body preparation was then diluted to a final concentration of 5 mg protein per ml with the 6M GuHCl/Tris buffer.

Once the protein had been solubilized and diluted as just described, an initial ammonium sulfate fractionation step was performed. Using a peristaltic pump, a saturated solution of ammonium sulfate was added dropwise with stirring to a final concentration of 25% saturation at 0° C. The resulting suspension was stirred on ice for another 30 min following the completion of the ammonium sulfate addition, after which it was centrifuged 10 min at 12,000 rpm in a Sorvall GSA rotor. The supernatant, which contains primarily impurities, was discarded. The pellets were washed with sterile saline in a volume equivalent to that of the original solubilized protein solution to remove residual ammonium sulfate. Pellets were stored at 4° C. until further processing.

A Q-Sepharose Fast Flow® anion exchange column (Pharmacia) was equilibrated with 25 mM Tris-Cl, pH 8. The washed ammonium sulfate precipitate containing the mutant rCRP was solubilized at a concentration of 0.5 mg/ml by adding 10 mM Tris base and stirring until a suspension was formed. NaOH was then added until the solution became clear (pH 12.2–12.5). The pH was then titrated to 9.0 with HCl. The solubilized protein was loaded onto the Q-Sepharose Fast Flow® column at a linear flow rate of 30 cm/hour, with the total protein load not exceeding 5 mg/ml of resin. The column was washed with 1 volume of the equilibration buffer (25 mM Tris-Cl, pH 8), and then developed with a two-column volume linear gradient of 0–1M NaCl in 25 mM Tris-Cl, pH 8. After the NaCl concentration was rapidly returned to 0, the column was washed with an additional column volume of the equilibration buffer. The mutant rCRP was finally eluted from the column with 8M GuHCl in 25 mM Tris, pH 8. $A_{280}$ was measured using the BioPilot® system.

The mutant rCRP adsorbs very strongly to the Q-Sepharose Fast Flow® column in the absence of a denaturant and will not elute with the NaCl gradient or with a pH gradient up to at least pH 12, allowing for an excellent separation of the mutant rCRP from endotoxin. The mutant rCRP readily elutes from the column in the presence of a denaturant, such as GuHCl. However, urea should not be used for this elution step.

The eluate from the Q-Sepharose Fast Flow® column was concentrated by precipitation with 25% saturated ammonium sulfate as described above. After the pellet was washed with saline, it was dissolved in 3% (w/v) sodium dodecyl sulfate (SDS), 25 mM Tris-Cl, pH 9.0 at a concentration of 5–10 mg protein/ml (estimated using absorbance at 280 nm and extinction coefficient for pure mCRP). It was then applied to a 5 cm×92 cm SUPERDEX 200®, spherical composite of cross-linked agarose and dextran, Pharmacia Biotech Inc., Piscataway, N.J. gel filtration column previously equilibrated in 1% SDS, 25 mM Tris-Cl, pH 8.0. The sample size was 1–1.5% of the column volume, and the linear flow rate was 30 cm/hr. The mutant rCRP typically eluted at a volume of 1120 ml (60% of the total bed volume), and collection began when the peak reached 25–30% of its expected height and was terminated when it returned to the same level. $A_{280}$ was measured on the Biopilot® system.

The mutant rCRP collected from the SUPERDEX 200®, spherical composite of cross-linked agarose and dextran, Pharmacia Biotech Inc., Piscataway, N.J. column were first chilled to 0–4° C. Any precipitated SDS was then removed by a 5–10 min centrifugation at 12,000 rpm in a Sorvall GSA rotor. Then 5 µl of a 25% (w/v) solution of KCl per ml of supernatant was added, and the insoluble potassium dodecyl sulfate was removed by centrifugation at 12,000 rpm in a Sorvall GSA rotor. The KCl addition and centrifugation were repeated twice more. Finally, the supernatant was brought to 30% saturated ammonium sulfate and the resulting precipitate was collected by centrifugation at 12,000 rpm in a Sorvall GSA rotor. The pellet was dissolved at 3–4 mg protein/ml (estimated as described above) in 10 mM Tris-Cl, pH 9.2.

The solubilized mutant rCRP was next applied to a Sephadex G-25 (fine) column (Pharmacia) equilibrated in 10 mM Tris-Cl, pH 7.4, at a linear flow rate of 70 cm/hr with the sample volume not to exceed 20% of the column volume. $A_{280}$ and conductivity were measured on the Biopilot® system, and the mutant rCRP was usually present at a concentration of 1.5–2 mg/ml.

Figure 14:
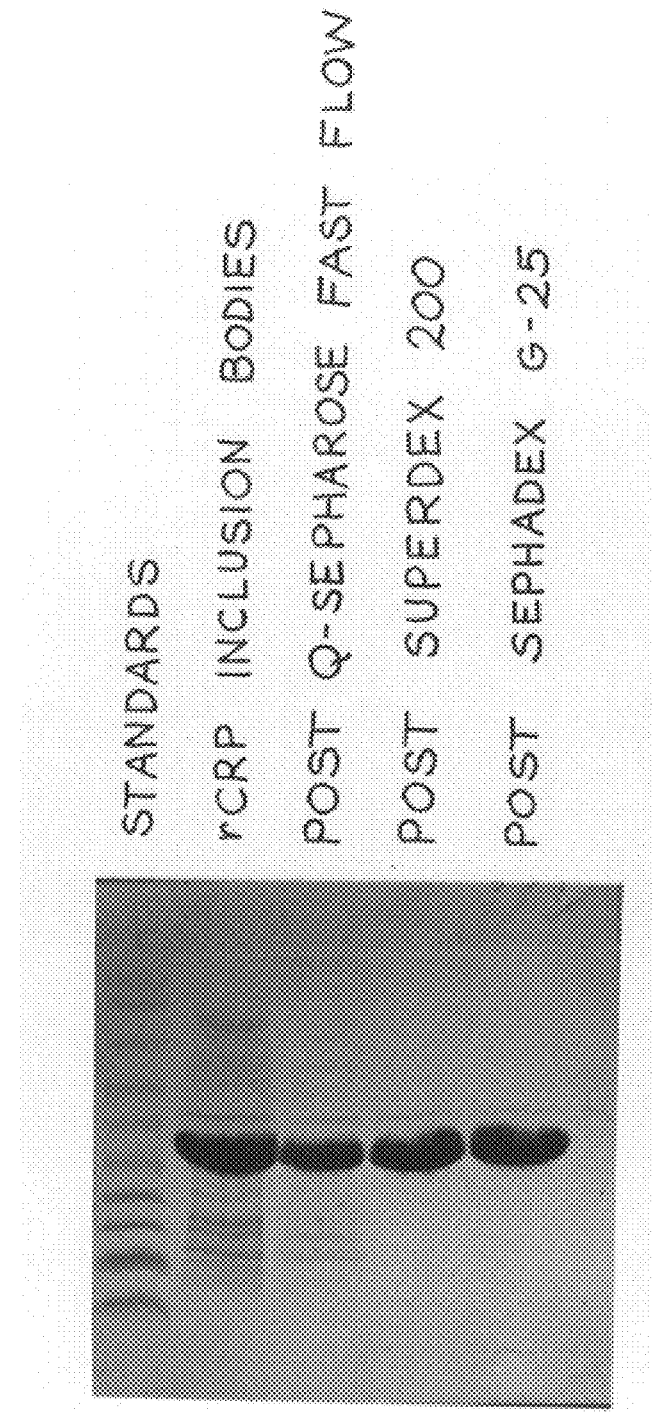
FIG. 14 presents representative SDS-PAGE results for the complete purification scheme for isolating a mutant protein according to the invention from *E. coli* BLR(DE3) bearing plasmid pIT13.

FIG. 14 presents the SDS-PAGE results for the complete purification scheme and illustrates the increase in purity attained in each step. The final mutant rCRP preparation is nearly homogenous. To perform the SDS-PAGE, samples were boiled in 2.5% SDS and 5% (v/v) β-mercaptoethanol, and 8 µg of each sample was loaded onto a 20% homogeneous PHASTGEL polyacrylamide gels, Pharmacia Biotech Inc., Piscataway, N.J. Proteins were visualized by staining with Coomassie Brilliant Blue.

The concentration of residual SDS in the mutant rCRP preparation was measured using the acridine orange binding assay described in Anal. Biochem., 118, 138–141 (1981). Following the purification protocol described above, the concentration of residual SDS in the mutant rCRP preparation is routinely below the limit of detection (~0.001% w/v) of the assay.

Finally, the purified mutant rCRP was sterile filtered through 0.2µ filters. The filtered, sterile mutant rCRP was then bottled in pyrogen-free sterile vials for injection.

I. Characterization Of The Mutant rCRP

1. SDS-PAGE and Western blot

Purified mutant rCRP produced by the method described in section H was compared with mCRP in SDS-PAGE and Western blot analyses. SDS-PAGE was performed using 20% PHASTGEL polyacrylamide gels, Pharmacia Biotech Inc., Piscataway, N.J. (Pharmacia). Gels were stained for protein using Coomassie Brilliant Blue. Gels were subjected to Western blot analysis by transferring the electrophoretically-separated protein onto nitrocellulose paper and adding monospecific goat anti-neo-CRP antiserum (prepared as described in section D above).

Figure 15A:
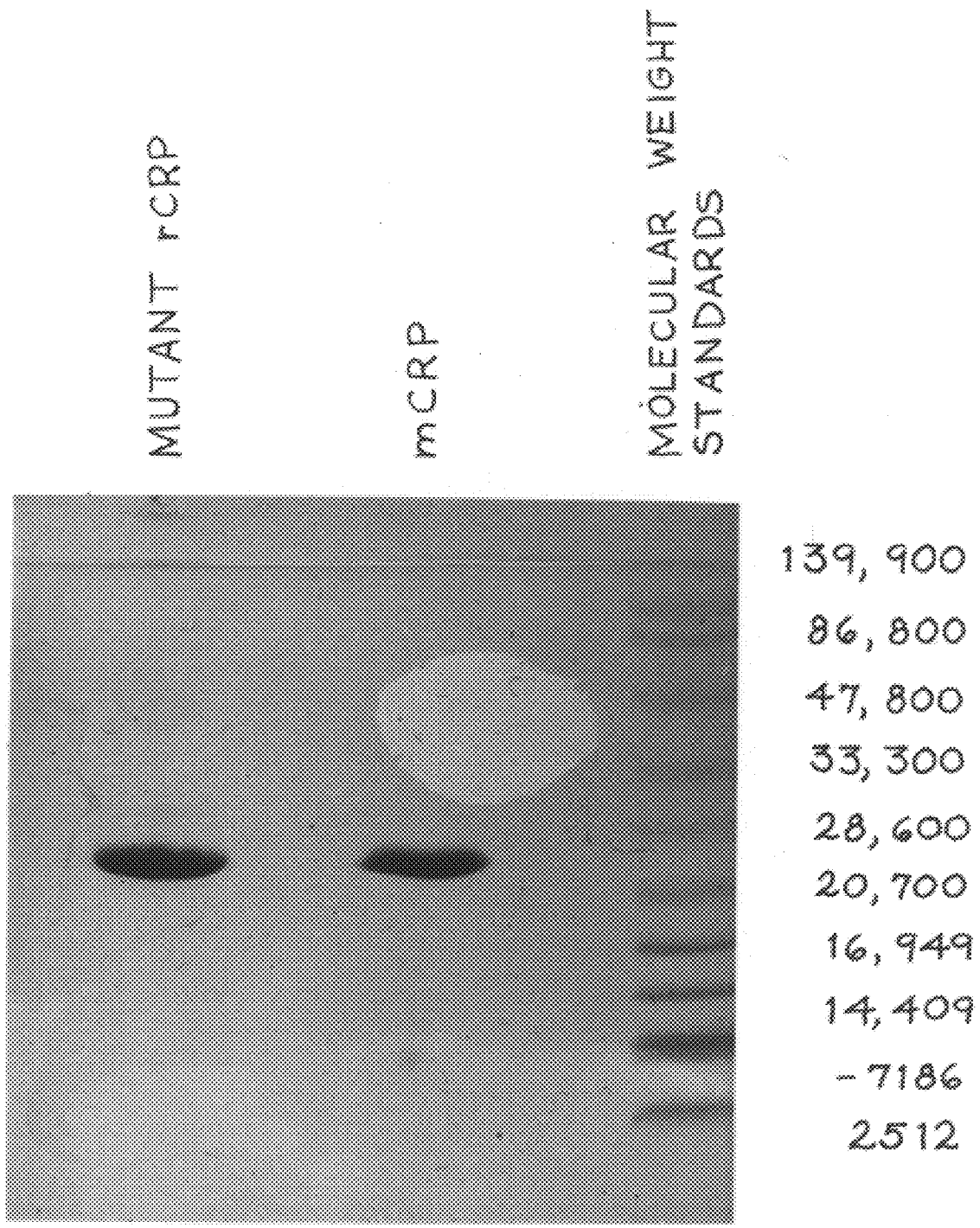
FIG. 15A is an SDS-PAGE gel obtained by electrophoresing mCRP and a mutant protein according to the invention purified from *E. coli* BLR(DE3) bearing plasmid pIT13.
Figure 15B:
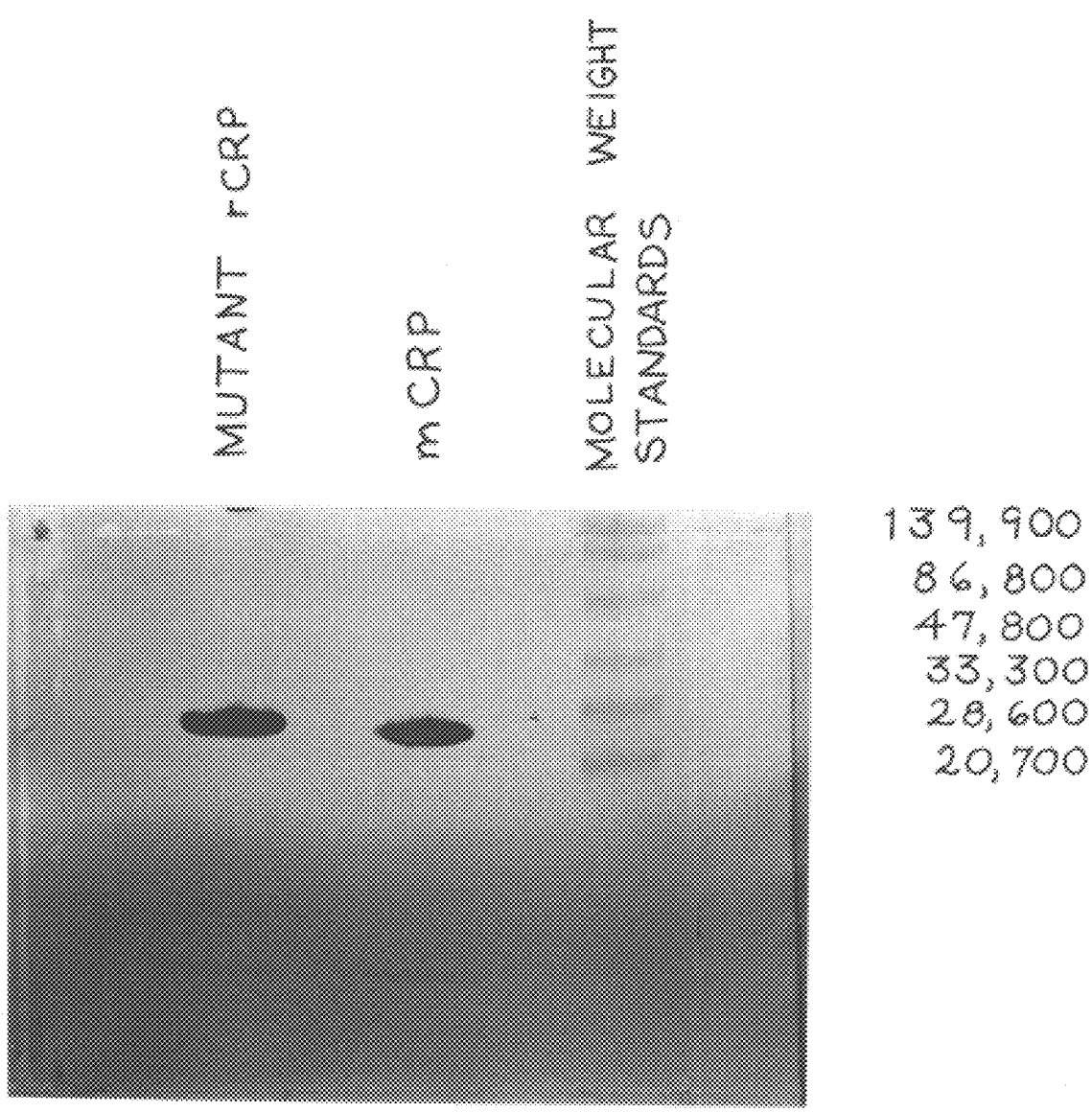
FIG. 15B is the Western blot obtained by using anti-neo-CRP monoclonal antibody 3H12 to stain the SDS-PAGE electrophoretic patterns of mCRP and a mutant protein according to the invention purified from *E. coli* BLR(DE3) bearing plasmid pIT13.

The results are shown in FIGS. 15A and 15B. In particular, the mutant rCRP and mCRP migrated as single bands on SDS-PAGE; no extraneous Coomassie-staining bands were noted in either sample suggesting that both the mCRP and the mutant rCRP are pure to the level of sensitivity of this analytical procedure. Each protein migrated with identical apparent molecular weights of Mr 23,000. This agrees with the literature values for the molecular weight of the unmutated CRP subunit in SDS-PAGE and with the molecular weights calculated from the known primary sequences of the unmutated CRP subunit (Mr 22,976) and mutant rCRP (Mr 23,114). These data show that the mutant rCRP has a molecular weight and purity essentially identical to mCRP.

Western blot analysis using mCRP-specific monoclonal antibody 3H12 demonstrates that the protein bands of both the mutant rCRP and of mCRP strongly reacted with this antibody (see FIG. 15B). No additional bands appeared in the transblotted lanes of either isolated protein, indicating an even greater level of purity than indicated by the SDS-PAGE results, since the Western blot results are more sensitive than the Coomassie staining technique. Monoclonal antibody 3H12 is known to react with the carboxy-terminal octapeptide of mCRP. These data show that the mutant rCRP expresses a very similar (probably identical) epitope as that of mCRP.

2. ELISA Analyses

An ELISA assay was performed to determine if monoclonal antibodies specific for different epitopes on mCRP would react with the mutant rCRP produced by pIT13 and purified as described in section H. The ELISA assay was performed as described in section D above using the following three monoclonal antibodies: 3H12, 8C10 and 7A8. The preparation and properties of mAb 3H12 and 8C10 are described above in section D. The preparation and properties of mAb 7A8 are described in U.S. Pat. No. 5,272,257, PCT application WO 91/00872, Ying et al., J. Immunol., 143, 221–228 (1989) and Ying et al., Mol. Immunol., 29, 677–87 (1992). Monoclonal antibody 3H12 reacts with the terminal octa-peptide of mCRP, as noted above. Monoclonal antibody 8C10 reacts with an epitope near the amino end of the mCRP sequence; this epitope is presumed to involve residues 22–45, which includes cysteine 36 which is mutated in the mutant rCRP. See Ying et al., Mol. Immunol., 29, 677–687 (1992). Monoclonal antibody 7A8 reacts with a third region of mCRP presumed to involve residues 130–138. See Ying et al., *Mol. Immunol.*, 29, 677–687 (1992).

Figure 16A:
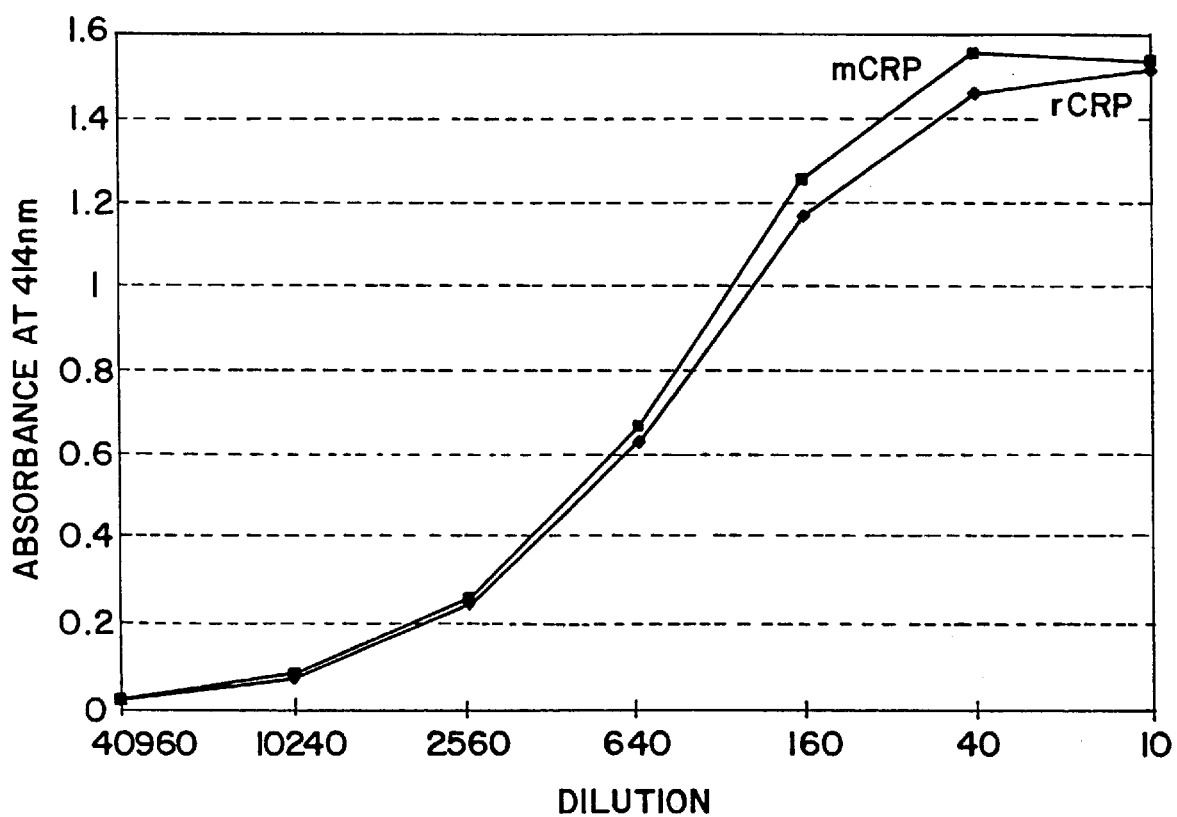
FIGS. 16A–C are graphs of the results of ELISA assays performed to detect the presence of neoCRP antigenic determinants on mCRP and a mutant protein according to the invention purified from *E. coli* BLR(DE3) bearing plasmid pIT13. Three different anti-neo-CRP monoclonal antibodies were used: 3H12 (FIG. 16A); 8C10 (FIG. 16B); and 7A8 (FIG. 16C).
Figure 16B:
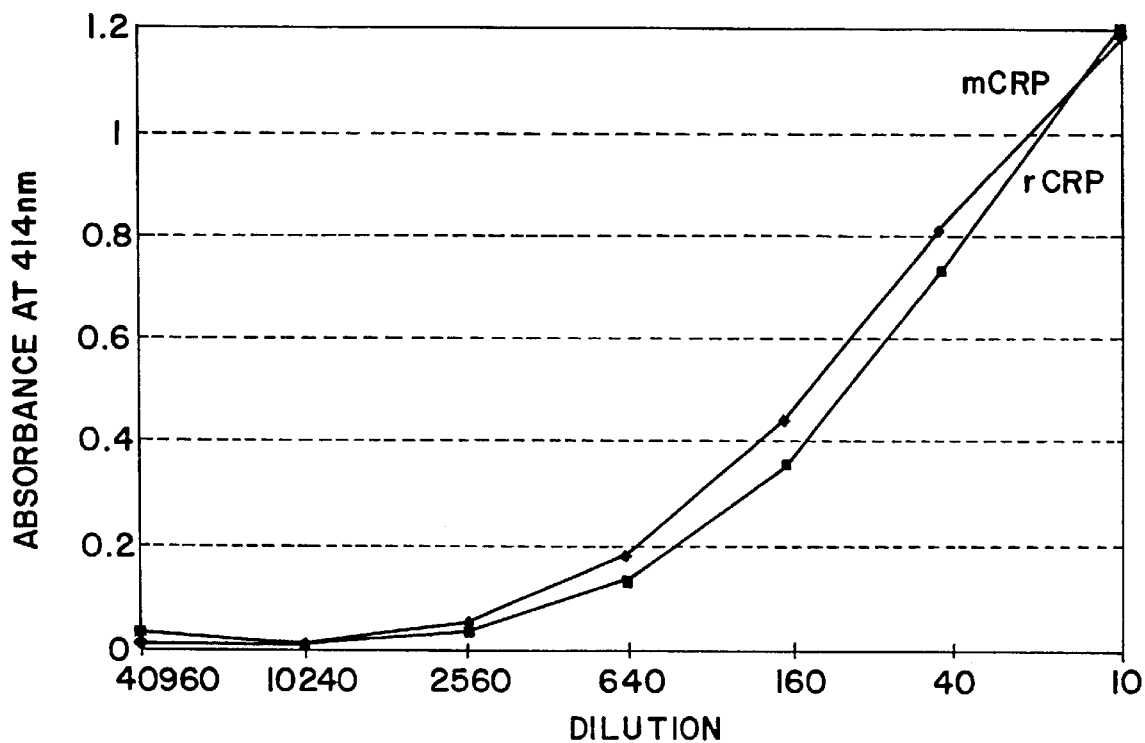
Figure 16C:
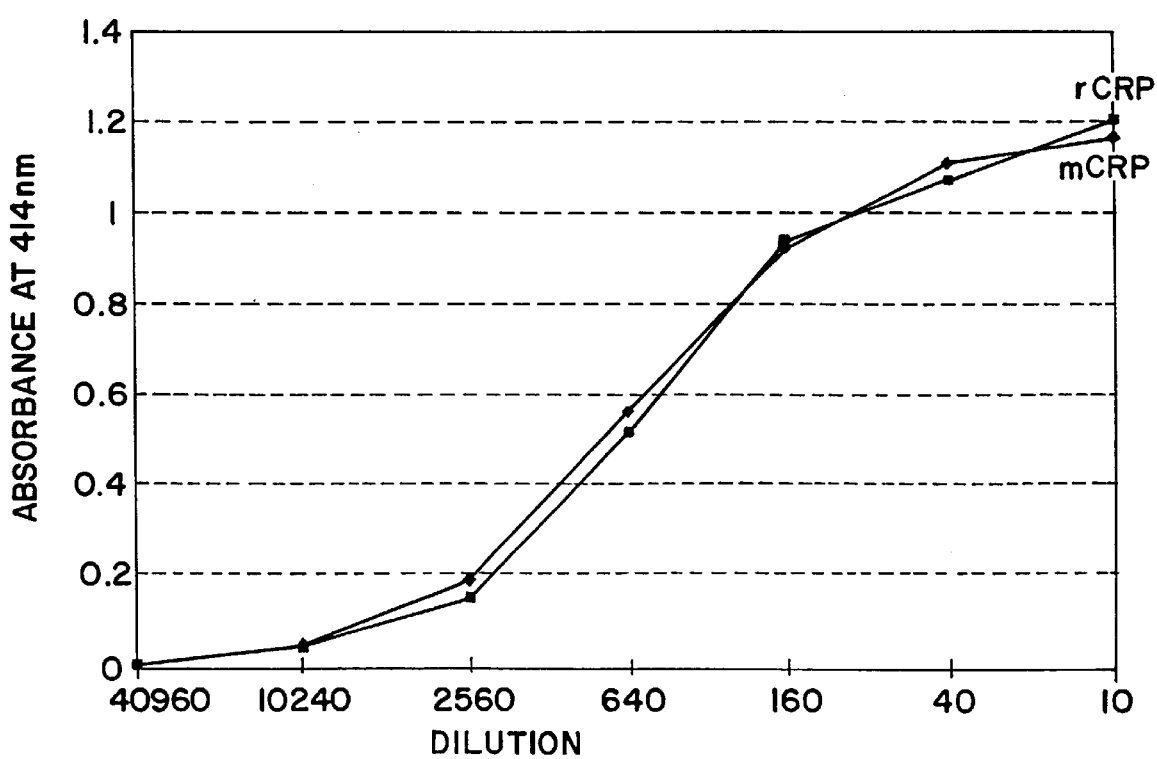

The ELISA results are shown in FIGS. 16A–C. All three monoclonal antibodies reacted equivalently with mCRP and the mutant rCRP produced by pIT13, including mAb 8C10 which reacts with an epitope believed to include cysteine 36. Each binding curve had a similar shape and relative intensity, suggesting that the mutant rCRP and mCRP both are comprised of, and express, these three distinct epitopes.

J. Amino Acid Sequence Of Mutant rCRP Produced By pIT4

Experiments were conducted to determine the amino acid sequence of the full-length mutant rCRP subunit produced by pIT4. Since this full-length product is believed to be produced by a ribosomal frameshift during translation of the MRNA, its amino acid sequence cannot be determined from the DNA sequence of pIT4 (see section F above).

First, mCRP and the full-length mutant rCRP subunits produced by pIT4 and pIT13 were digested with 2-(2'-nitrophenylsulfenyl)-3-methyl-3'-bromoindolenine (BNPS-Skatole; Pierce Biochemicals) which cleaves on the C-terminal side of tryptophan residues. The full-length products of pIT4 and pIT13 were produced by culturing *E. coli* BL21(DE3) and BLR(DE3), respectively, and purifying the full-length products from the cultures, all as described above. The mCRP and the final purified pIT4 and pIT13 products were solubilized at a concentration of 50 mg/ml in 25 mM Tris-Cl, pH 8, containing 6M GuHCl. The reactions were initiated by the addition of four volumes of glacial acetic acid containing 25 mg/ml BNPS-Skatole. Thus, the final reaction conditions were 10 mg/ml protein, 1.2M GuHCl, 80% acetic acid and 20 mg/ml BNPS-Skatole. After a 24-hour digest at room temperature in the dark, 42.5 $\mu$l of each sample were transferred to an Eppendorf tube, and an equal volume of saturated ammonium sulfate was added to each tube. After a two-minute centrifugation in an eppendorf micro centrifuge, the supernatants were discarded, and the pellets were washed with 200 $\mu$l of 0.1M Tris-Cl, pH 7.4. The pellets were finally suspended in 42.5 $\mu$l of 8M urea in 25 mM Tris-Cl, pH 8.5. The samples were then analyzed by SDS-PAGE performed as described in section I above.

There is a Trp in the CRP sequence at position 67 which is also found in the Tenchini et al. sequence (see Table 2). Cleavage at this site would produce a fragment of ~8000 Mr. Digestion of the mCRP and of the pIT13 product produced a prominent fragment of this size, whereas digestion of the pIT4 product produced a fragment of ~11,000 Mr, the expected size if Trp68 were absent. Since the pIT4 and pIT13 products were digested under identical conditions, these results strongly suggest that Trp68 is missing in the pIT4 product and that the out-of-frame sequence of pIT4 extends at least to codon 67.

In a second experiment, the two mutant rCRP's were digested with endoproteinase LysC (Boehringer Mannheim Biochemicals), which cleaves specifically at the C-terminal side of lysine residues. The purified mutant rCRP's (prepared as described above, this section) were solubilized in 8M urea, 25 mM Tris-Cl, pH 8.0, at a concentration of 5 mg/ml. Then, 0.1M Tris-Cl, pH 7.4, enzyme and water were added in sufficient quantities to give final conditions of 25 mM Tris-Cl, pH 7.4, 4M urea, 0.05 U enzyme, and 2.5 mg/ml protein. The digests were incubated for 24 hours at room temperature, and the digestion products were analyzed by SDS-PAGE as described in section I above, except that high density gels designed for peptide separations were used.

In the region of the protein sequence in question, digestion of the pIT13 product with LysC would be expected to yield fragments of Mr 2961 (residues 32–57), 1548 (residues 58–69) and 4827 (residues 70–114). In the pIT4 product, the lysine at position 57 is predicted to be absent, and a novel lysine present at position 59 (see Table 2). If the lysine at position 69 is present in this protein, digestion with LysC should produce fragments of Mr ~3200 (residues 32–59), ~1100 (residues 60–69) and 4827 (residues 70–114). In contrast, if it is absent, the 4827 and ~1100 Mr fragments would be replaced by a fragment of ~6000 Mr. A fragment produced by digesting both the pIT4 and pIT13 proteins which migrates at ~4800 Mr was observed, and there is no trace of a ~6000 Mr fragment in the pIT4 protein digest. These results indicate that there is a lysine at position 69 in the mutant rCRP's produced by both pIT4 and pIT13.

Taken together with the original amino acid composition and DNA sequence data (see section F above), the results of these two experiments strongly suggest that the sequence of the full-length mutant rCRP produced by pIT4 has the following amino acid sequence from position 47 to position 69:

```
Arg Gly Thr Val Phe Ser Arg Met      SEQ ID NO:24
              5
Pro Pro Arg Asp Lys Thr Met Arg
    10                  15
Phe Ser Tyr Phe GlyLeu Lys
              20
```

Residues shown in bold are those that likely differ from the bona fide CRP sequence and from the Tenchini et al. sequence (see Table 2 above). Those residues which are underlined are still questionable in terms of their identity.

Example 3
Effect of mCRP on Megakaryocytopoiesis in Vitro

Six to seven week old specific pathogen free ICR mice were obtained from CLEA Japan, Ltd., Tokyo, Japan, and climatized for three weeks. Bone marrow cells were then harvested from mice femurs.

Meg-CFC cultures were performed according to the procedure described in Mizoguchi et al., *Exp. Hematol.*, 7:346 (1979). The bone marrow cells ($5\times10^5$/dish) were immobilized in a plasma clot attached to the bottom of a Petrie dish. Plasma clots were formed by mixing bone marrow cell suspensions in Eagle's minimal essential medium/Hanks' balanced salt solution (HMEM from GIBCO) containing 20% fetal calf serum, 20% NCTC109 solution (DIFCO), 10% bovine embryo extract (diluted 1:5), 1% bovine serum albumin, 0.02 mg/ml asparagine, 7% Pokeweed-mitogen stimulated spleen lymphocyte-conditioned medium and 10% bovine citrated plasma (Sigma) to make a final volume of 0.4 ml–0.6 ml per dish. After clotting, 0.4–0.6 ml HMEM plus 10% fetal calf serum was added to each Petrie dish.

The bone marrow cultures were incubated in the presence of either control solutions or solutions containing various doses of either mCRP or native CRP. Both soluble and suspended forms of mCRP were prepared using partially purified native CRP (Western States Plasma, Fallbrook, Calif.) as the starting material. The native CRP was sterile filtered and further purified by ion exchange chromatography as described in Example 1, Section A. The solution and suspended forms of mCRP were produced by processing the native CRP in accordance with the methods described in Example 1, Section B.

The control solutions generally were identical buffers except lacking mCRP or native CRP. In some experiments, control solutions consisted of buffers containing other hematopoietically-active cytokines such as G-CSF or IL-6. The test cultures were incubated with either native CRP, solution-mCRP or suspension-mCRP. Native CRP and mCRP were tested at concentrations ranging from 0.1 $\mu$g to 100 $\mu$g/ml.

The bone marrow cultures were incubated for 5 days at 37° C. in a fully humidified incubator containing 5% $CO_2$.

The plasma clots were then dehydrated, fixed with 5% glutaraldehyde, stained for acetylcholinesterase activity and counter-stained with Harris hematoxylin. Next, the cultures were analyzed using an inverted microscope. Colonies consisting of four or more positively-stained cells were scored as one colony.

Figure 5A:
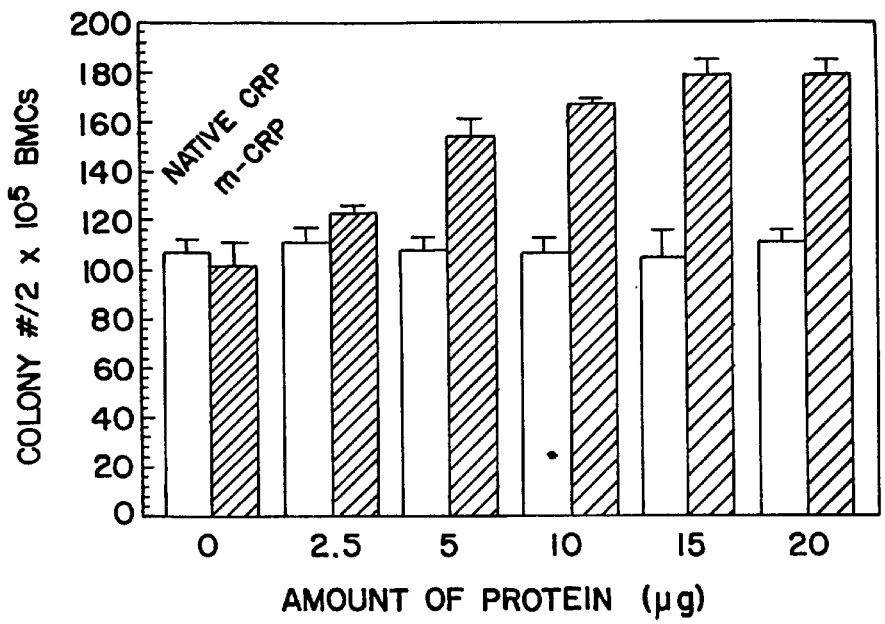
FIG. 5A is a bar graph showing the effect of mCRP on megakaryocyte colony formation in vitro.

At doses of 2.5 μg to 20 μg, mCRP increased the number of megakaryocyte colonies formed, increasing from approximately 100 colonies/$2\times10^5$ bone marrow cells to approximately 180 colonies/$2\times10^5$ bone marrow cells. (See FIG. 5A). The mCRP-treated cultures showed megakaryocyte colony formation from 40-to-100% above that observed in control cultures and cultures incubated with native CRP. Native CRP-treated cultures showed the same number of colonies/dish as the control, buffer-treated samples.

Figure 5B:
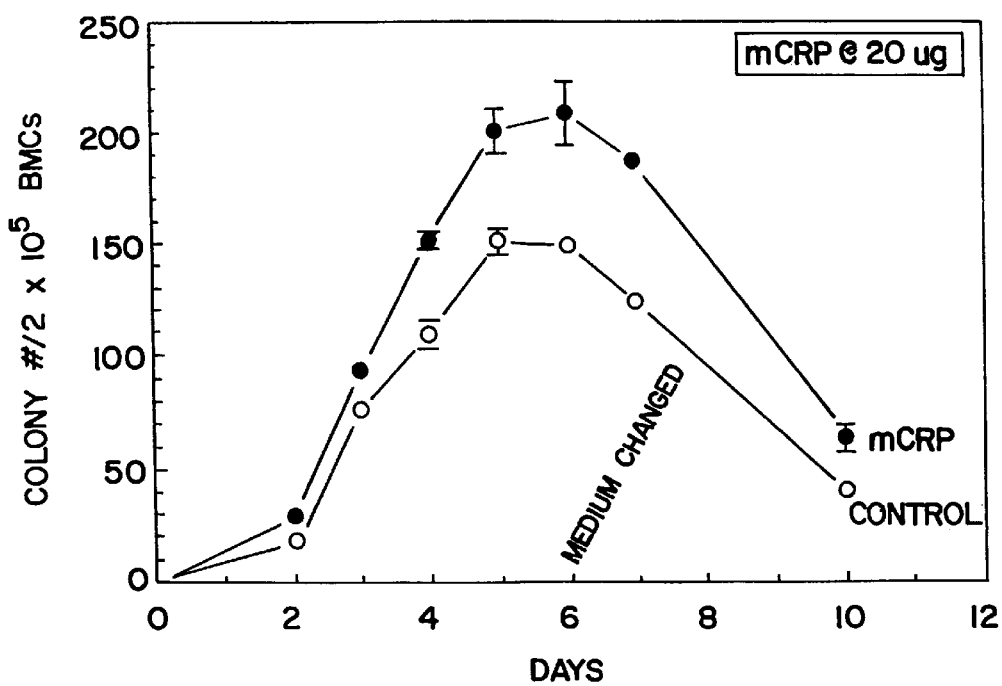
FIG. 5B is a graph of the effect of mCRP on the kinetics of megakaryocyte colony formation in vitro.

FIG. 5B illustrates the kinetics of that megakaryocyte colony formation. Control megakaryocyte cultures appeared on day 2 as immature cells, and on day 3 as more mature cells. Maximum numbers of colonies were noted on days 5–6. After this time, the cytoplasm of the megakaryocyte colonies decreased indicating degradation of colonies. Modified-CRP-treated megakaryocyte colonies were more mature on day 4 compared to control colonies. The number of colonies quantified in mCRP-treated cultures increased approximately 40% ($p<0.01$) on days 5–6 compared to control cultures. In this assay system, IL-6 showed no effect on megakaryocytopoiesis at doses from 10 μg to 100 μg/dish.

Figure 6A:
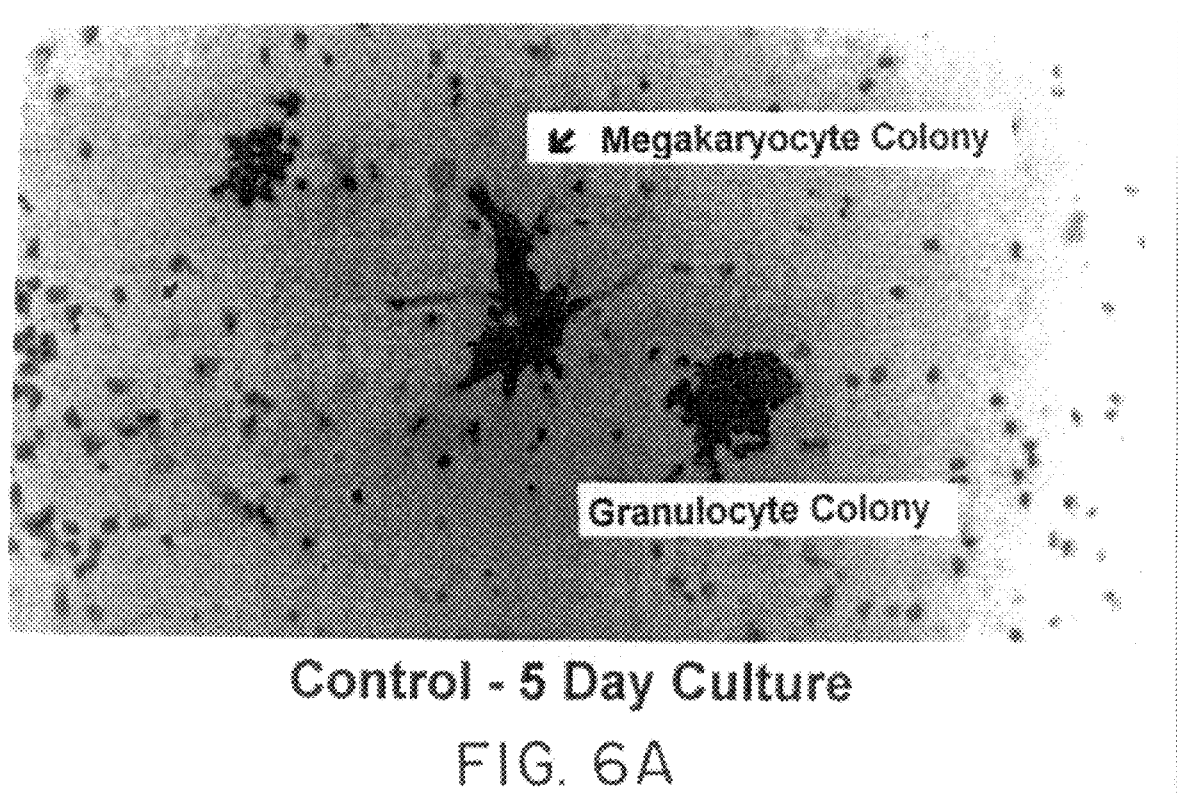
FIGS. 6A and 6B are photographs of control and mCRP-treated murine megakaryocyte colonies.
Figure 6B:
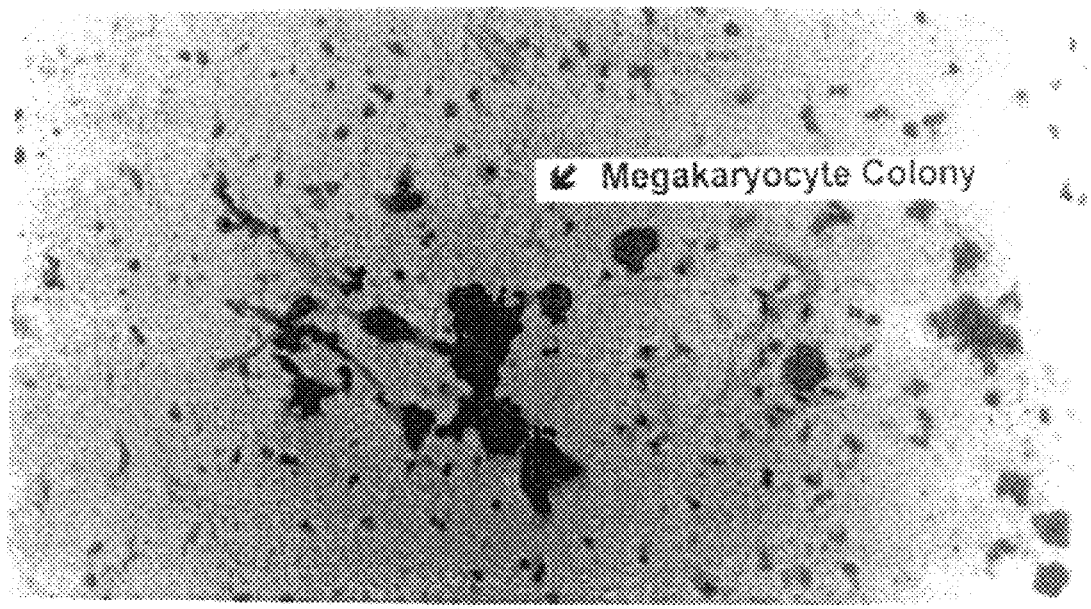

Under the microscope, the bone marrow cells treated with mCRP showed unusual proliferation with unusual shape. (See FIGS. 6A and 6B). Modified-CRP-treated megakaryocytes appeared larger than those observed in control cultures, with more pronounced pseudopods and heavily stained cytoplasm. The intensity of cytoplasmic staining is usually interpreted as an indication of megakaryocyte maturity. The data thus suggests that mCRP promoted megakaryocyte maturation and demonstrates Megakaryocyte-Potentiator activity.

Example 4
In Vivo Effect of mCRP on Thrombocytopoiesis in Normal Mice

Six to seven week old specific pathogen free ICR male mice were obtained from CLEA Japan, Ltd., Tokyo, Japan and climatized for a minimum of one week. Four groups of mice consisting of 4 mice/group or 5 mice/group were utilized in the study. Each group received either control buffer, native CRP, mCRP (in solution), or mCRP (in suspension). The mCRP was prepared using partially purified native CRP (Western States Plasma, Fallbrook, Calif.) as the starting material. The native CRP was sterile filtered and further purified by ion exchange chromatography as described in Example 1, Section A. The solution and suspended forms of mCRP were produced by processing the native CRP in accordance with the methods described in Example 1, Section B.

Figure 7A:
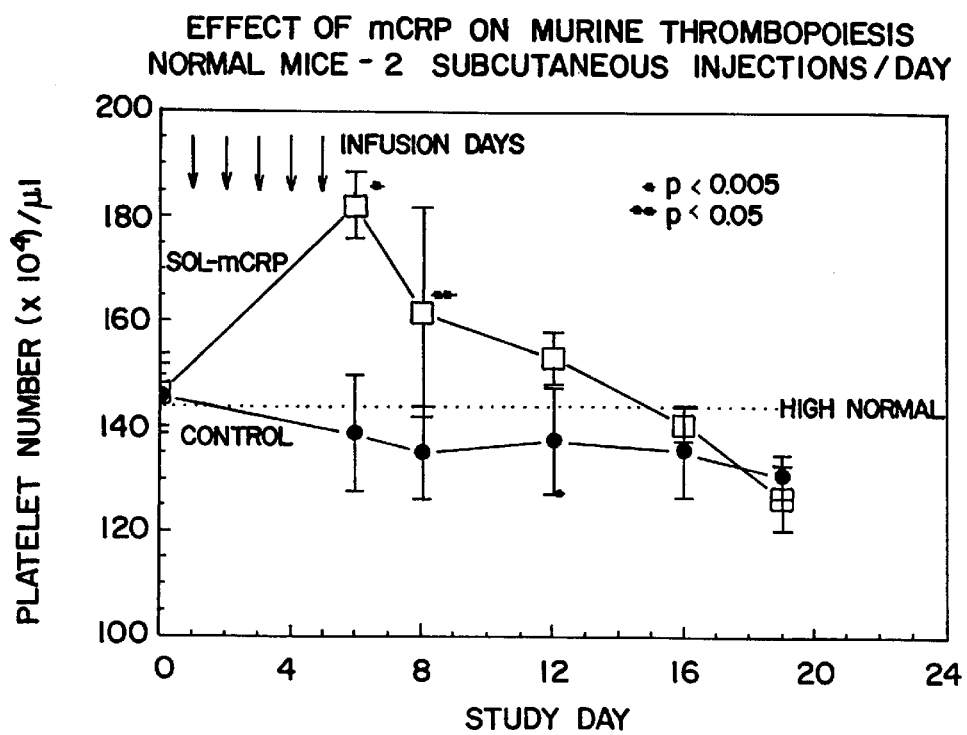
FIGS. 7A and 7B are graphs showing the effect of mCRP (subcutaneously injected) on thrombocytopoietic activity in normal mice.
Figure 7B:
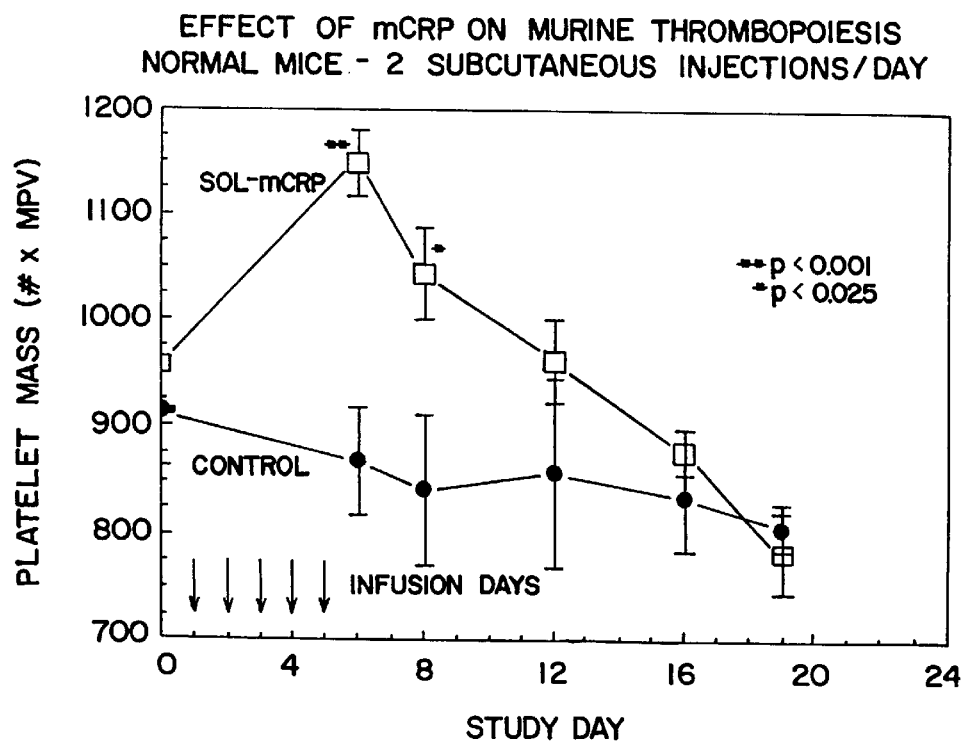
Figure 7C:
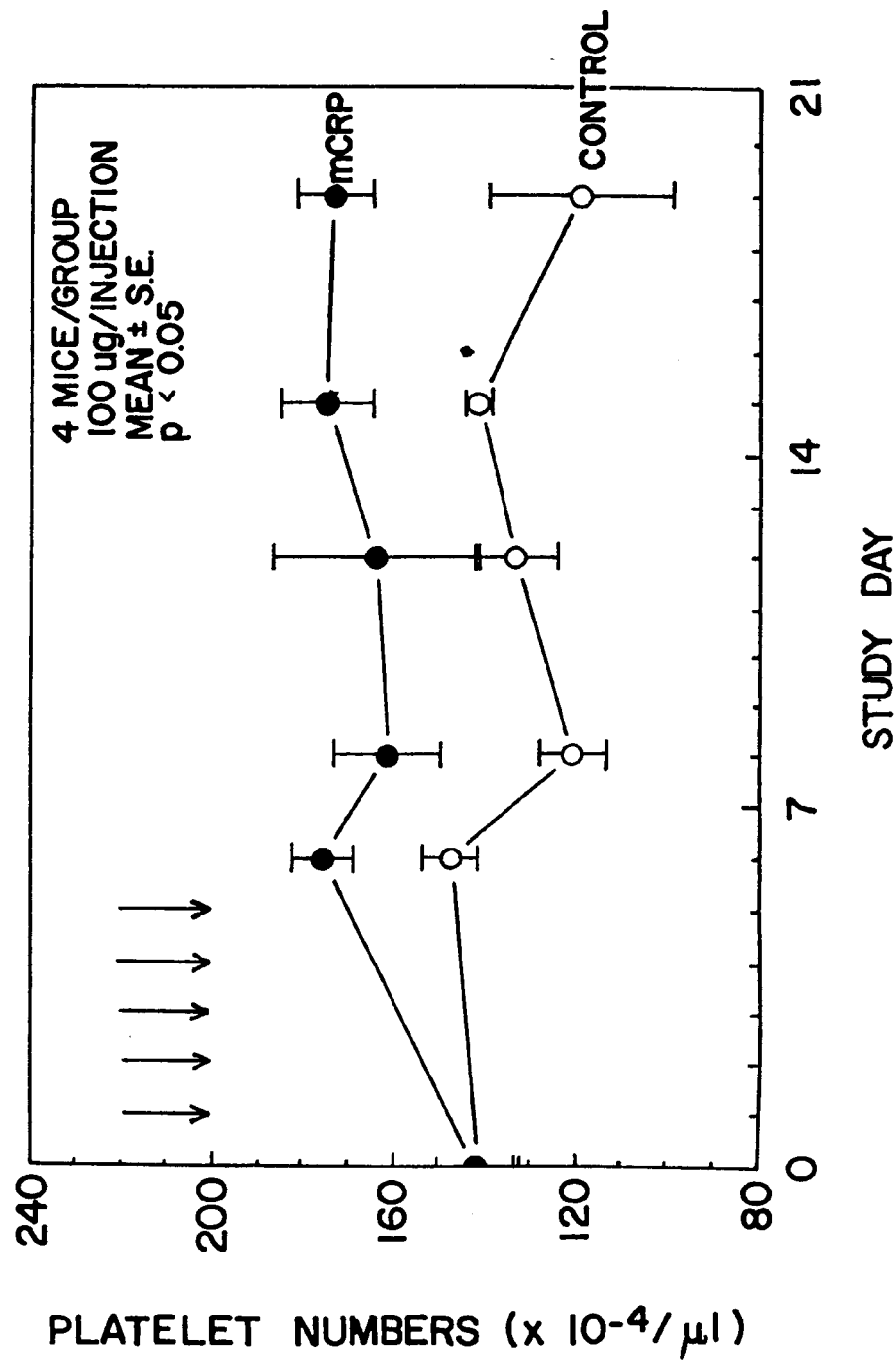
FIG. 7C is a graph showing the effect of mCRP (intraperitoneally injected) on thrombocytopoietic activity in normal mice.
Figure 8A:
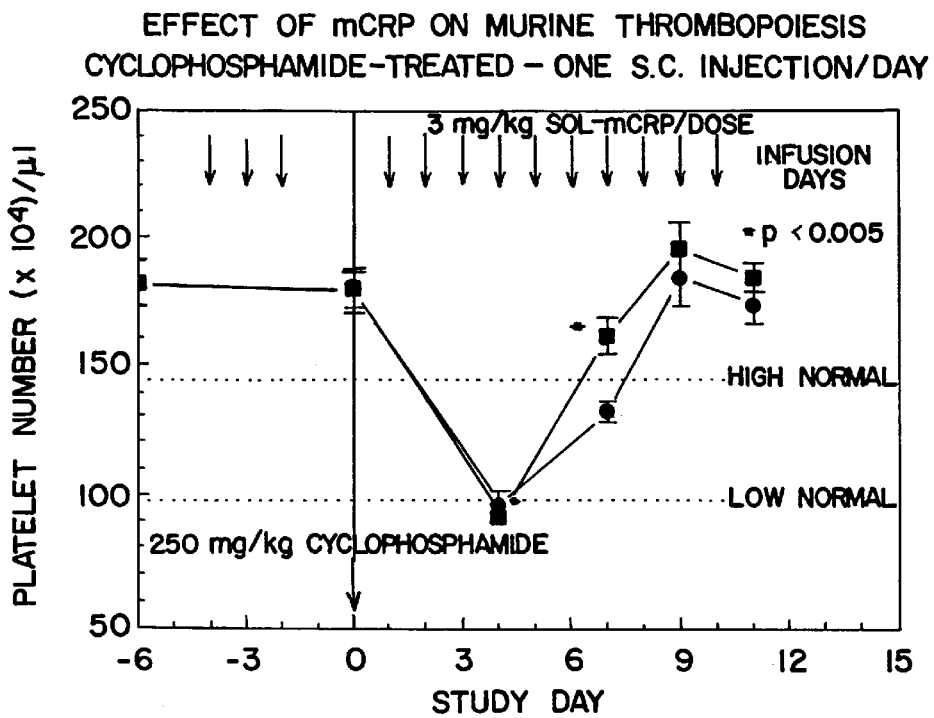
FIGS. 8A and 8B are graphs showing the effect of mCRP on platelet counts in Cyclophosphamide-treated mice.
Figure 8B:
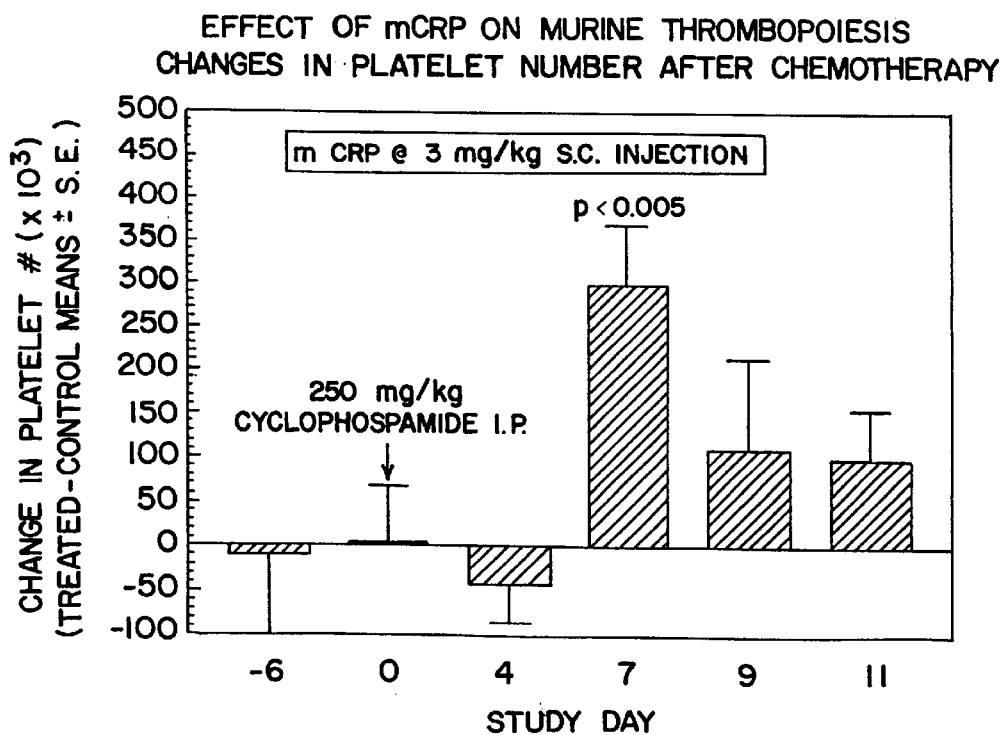
Figure 8C:
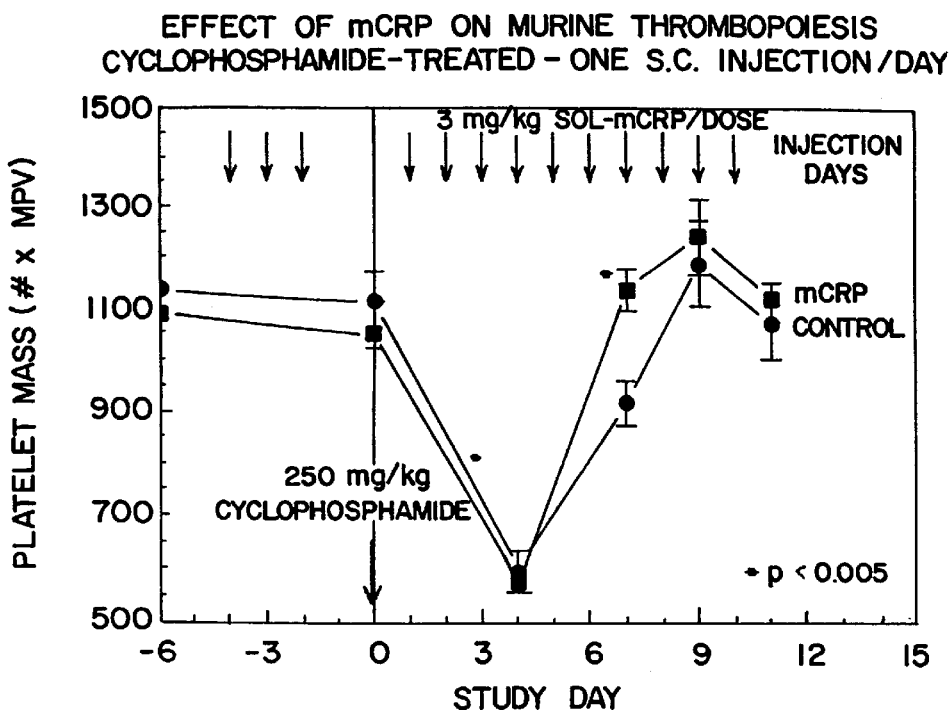
FIGS. 8C and 8D are graphs showing the effect of mCRP on platelet mass in Cyclophosphamide-treated mice.
Figure 8D:
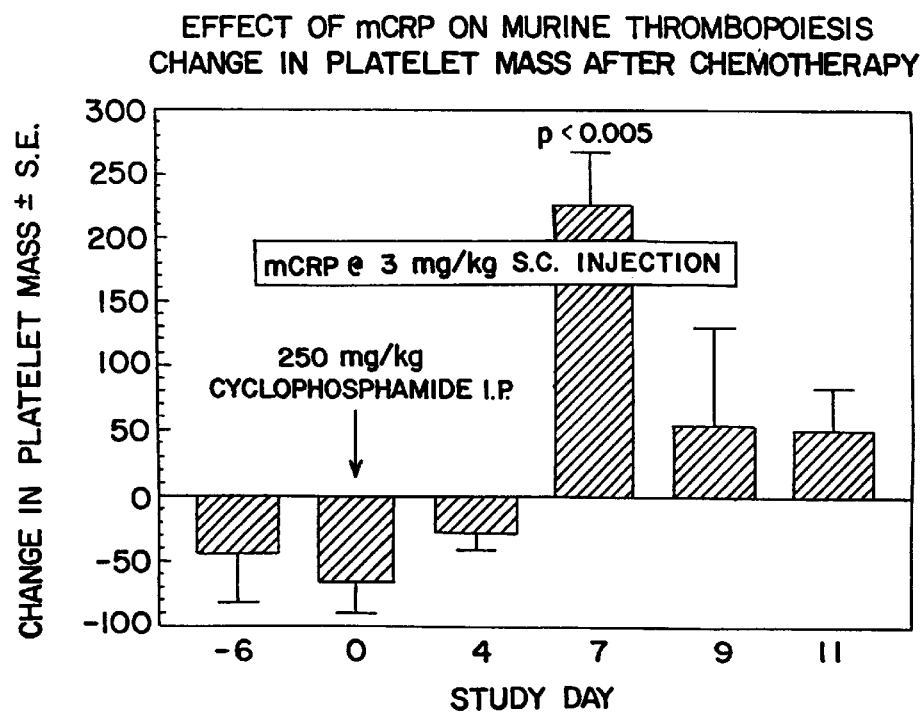
Figure 9A:
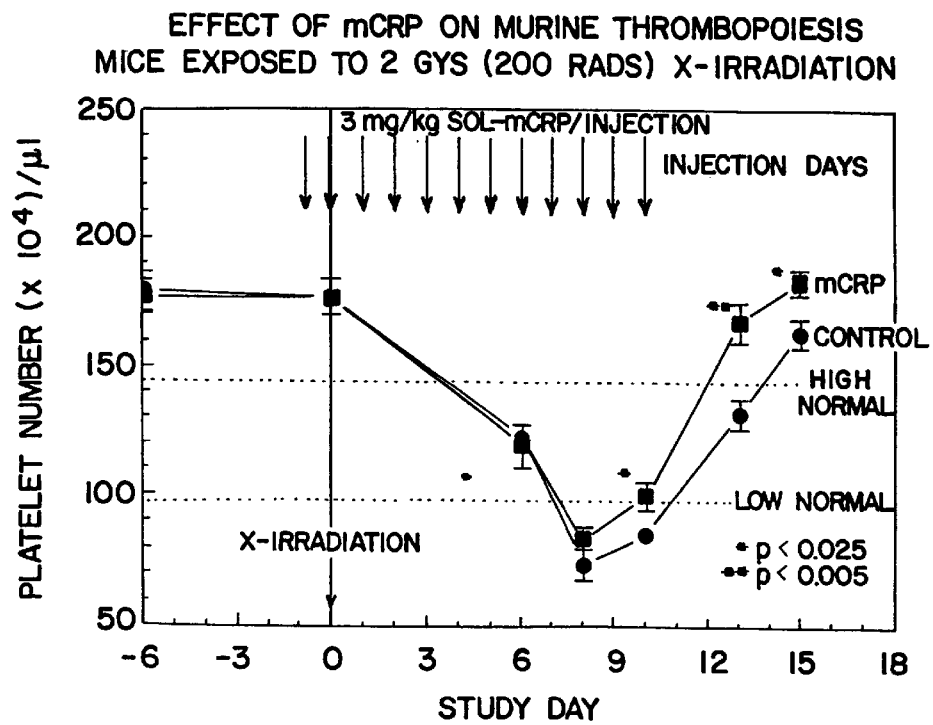
FIGS. 9A and 9B are graphs showing the effect of mCRP on platelet counts in X-irradiated mice.
Figure 9B:
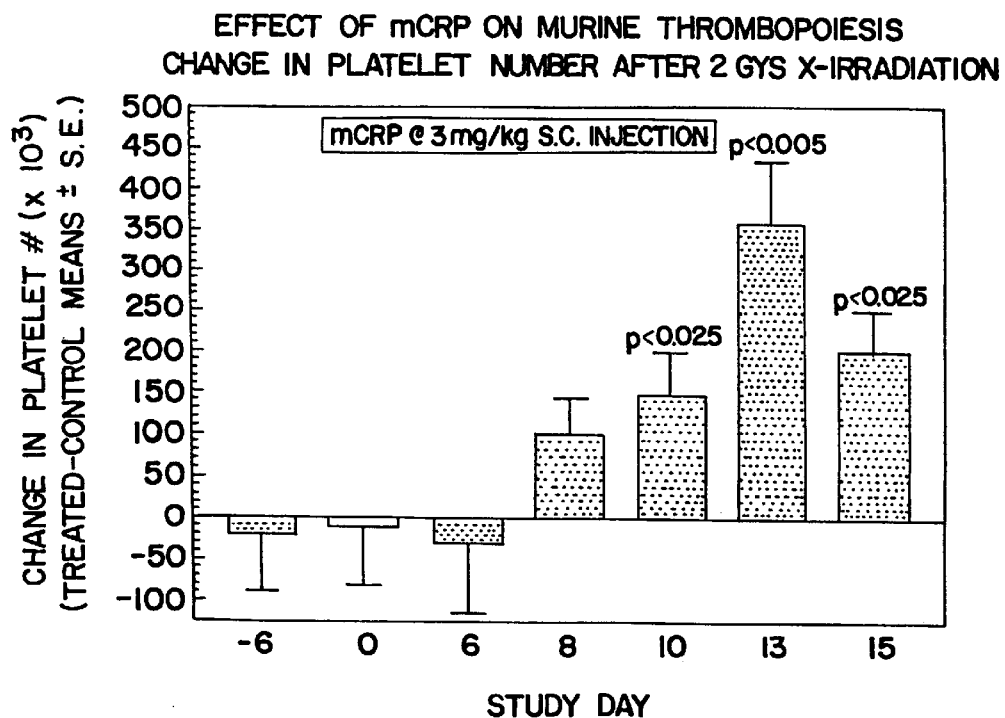
Figure 9C:
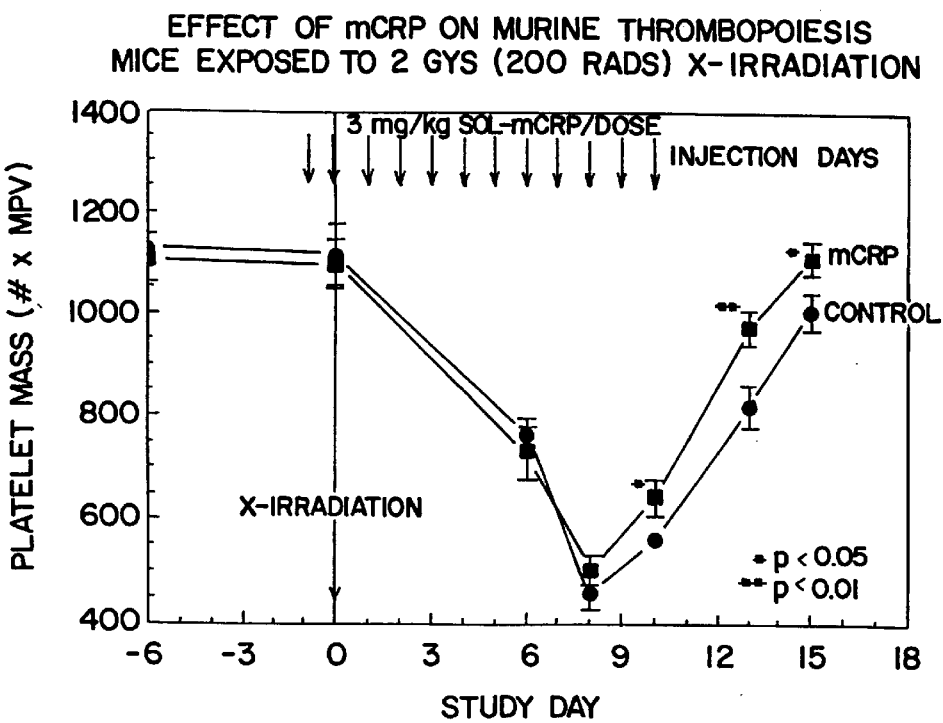
FIGS. 9C and 9D are graphs showing the effect of mCRP on platelet mass in X-irradiated mice.
Figure 9D:
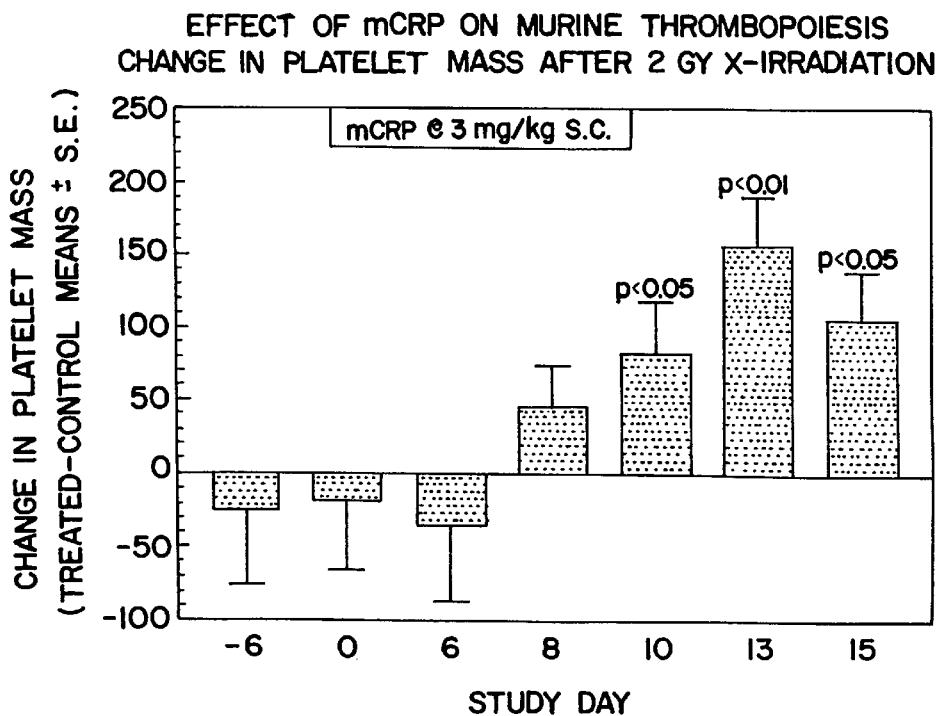

A total of 100 μg of protein (approximately 2–4 mg/kg body weight) was injected daily for 5 consecutive days (Day 1 through Day 5). The injections were made subcutaneously (2 injections/day; FIGS. 7A and 7B) or intraperitoneally (1 injection/day; FIG. 7C). Control mice received either control buffer lacking protein or sterile saline.

Blood analyses for the mice were performed by collecting 10 or 20 μl of blood from each mouse by slightly cutting the tail vein with a sharp razor. For each analysis, the first 10 μl of blood was wiped away to avoid tissue fluid. The blood sample was collected in a Drummond Microdispenser and diluted into a buffered solution containing a chelating agent (commercially available from Sysmex F800 vendor). Leukocyte (WBC) numbers, erythrocyte (RBC) numbers, mean erythrocyte volume (MCV), platelet (PLT) numbers, mean platelet volume (MPV), concentration of hemoglobin, and hematocrit were measured at various time intervals. A semi-automatic blood cell counter F800 (Sysmex) was used to make these measurements.

By day 6, mice injected subcutaneously with solution mCRP showed approximately a 25–30% increase in blood platelet levels compared to controls (FIG. 7A; $p<0.005$) and a significant increase in platelet mass (FIG. 7B; $p<0.001$). As discussed in the Background section, it has been reported that platelet count and mean platelet volume (MPV) are inversely related, i.e., as platelet numbers increase, MPV decreases [Thompson et al., Blood, 72:1–8 (1988)]. By taking the product of the platelet number and the MPV, a parameter termed "platelet mass" is defined. It is presently believed that platelet mass may correlate more closely with platelet function than does the platelet count alone. Therefore, calculation of platelet mass may be a superior measurement indicating the "maturity" and "function" of circulating platelets.

Blood platelet levels fell to control levels 1–2 weeks after therapy was stopped. Similar results were achieved when suspended mCRP was administered subcutaneously (data not shown).

When solution mCRP was administered intraperitoneally, the thrombopoietic activity again increased to significant levels by day 6 ($p<0.05$) compared to control groups (FIG. 7C). The increase in blood platelets in mCRP-treated mice persisted over the next two weeks (to day 19). Administering suspension mCRP intraperitoneally showed a similar significant increase in blood platelet number ($p<0.05$ on day 19) and platelet mass ($p<0.05$ on day 19). Native CRP-treated animals showed variable results (data not shown).

Example 5
In Vivo Effect of mCRP on Thrombocytopoiesis in Cyclophosphamide-treated Mice Modified-CRP was prepared using partially purified native CRP (Western States Plasma, Fallbrook, Calif.) as the starting material. The native CRP was sterile filtered and further purified by ion exchange chromatography as described in Example 1, Section A. Solution mCRP was then produced by processing the native CRP in accordance with the methods described in Example 1, Section B. Mice were injected subcutaneously with the solution mCRP at a dose of approximately 3 mg/kg body weight once/day on Days −4, −3, and −2. On Day zero, the mice were injected intraperitoneally with the chemotherapeutic drug, cyclophosphamide, at a dose of 250 mg/kg of body weight. Blood platelet levels were depressed by this amount of drug so that on Day 4, platelet counts fell to about half of the pre-treated levels. After chemotherapy was administered, the solution mCRP was injected subcutaneously in the mice at a dose of approximately 3 mg/kg body weight once/day for 10 days. Control animals were injected similarly with bovine serum albumin ("BSA") solution.

The results are illustrated in FIGS. 8A–8D. Treatment with solution mCRP resulted in accelerated recovery of platelet counts so that on day 7, the counts were near 90% of the starting level (See FIG. 8A). Control animals, receiving BSA solution instead of solution mCRP, took at least another two days to reach that level. On day 7, the control animals had only recovered to approximately 65% of pre-treatment platelet levels. Using the two-tailed students t-test, the platelet level of test animals on day 7 was found to be significantly increased over control mice to a p value <0.005.

Example 6
In Vivo Effect of mCRP on Thrombocytopoiesis in X-irradiated Mice

ICR normal mice (three treatment groups, consisting of 4–5 mice/group) were X-irradiated with a dose of 2.0 Gy (200 kV, 20 mM, 0.5 mm Cu/0.5 mm Al filters, dose rate 72 cGy/min) (Gy=Gray, 1 gray is equivalent to 100 Rads). At twenty hours and at two hours before completion of the irradiation, and once/day for 10 days after irradiation treatment was stopped, the animals were injected subcutaneously with approximately 3 mg/kg body weight solution mCRP. The solution mCRP was prepared using partially purified native CRP (Western States Plasma, Fallbrook, Calif.) as the starting material. The native CRP was sterile filtered and further purified by ion exchange chromatography as described in Example 1, Section A. The solution mCRP was then produced by processing the native CRP in accordance with the methods described in Example 1, Section B. Control animals were similarly injected with bovine serum albumin (BSA) solution.

The results are illustrated in FIGS. 9A–9D. Treatment with solution mCRP resulted in accelerated recovery of platelet counts so that by day 13 after X-irradiation, the counts were near 100% of the starting level (See FIG. 9A). Control animals, receiving BSA solution instead of solution mCRP, took at least another two days to reach that level. On day 13, control animals had only recovered to about 70% of pre-irradiation levels. Using the two tailed student's t-test, the platelet level of test animals was found to be significantly increased over the control animals on day 13 to a p value of <0.005 and on day 15 to a p value of <0.025.

Example 7
In Vivo Effect of mCRP on Thrombocytopoiesis in SIV-infected Rhesus Monkeys Two male rhesus monkeys infected with the Simeon Immunodeficiency Virus (SIV) were treated with approximately 2.8 mg/kg body weight/day of suspension mCRP by bolus intravenous injection on days 1, 2, 3, 4, and 5 of a three week period. The suspension mCRP was prepared as described in Example 1. Blood samples were drawn just prior to administration of mCRP on days 1, 3, and 5. Additional data points were also collected on days 12 and 19.

On days 12 and 19, both monkeys showed between 33 and 96% increase in blood platelet counts over pre-infusion values.

Example 8
In Vivo Effect of mCRP on Thrombocytopoiesis in HIV-positive Humans

Three HIV-positive male patients each received 7 infusions of suspension mCRP at a dose of 3 mg/kg body weight over a period of 15–29 days. The suspension mCRP was prepared using partially purified native CRP (Western States Plasma, Fallbrook, Calif.) as the starting material. The native CRP was sterile filtered and further purified by ion exchange chromatography as described in Example 1, Section A. The suspended mCRP was then prepared by heating the native CRP to 60° C. for 1 hour in the presence of 1 mM EDTA. The patients received intensive mCRP therapy during the first week (from 3-to-5 injections each), followed by once-a-week infusions for the next two-to-four weeks. Data was gathered over a period of two-to-three months before, during, and after the infusion of mCRP.

Overall, multiple infusions of mCRP were tolerated well with no significant adverse effects. A fever response was noted after all infusions; this was controlled by giving each patient aspirin and Tylenol®. No sign of organ damage (kidney, liver, lung pancreas, muscle) was noted, and no adverse effect on reticulocytes or leukocytes was noted. There was a drop in the hematocrit of each patient. However, this was not deemed related to mCRP therapy. Total lymphocyte counts, CD4+ lymphocyte counts and CD8+ lymphocyte counts, increased in all patients correlating with mCRP therapy. Serum electrolytes, enzymes, proteins and other factors (e.g, glucose, triglycerides, cholesterol, uric acid, BUN, creatinine) all remained within normal limits throughout the study. Both intrinsic and extrinsic coagulation pathways were unaffected by intravenous infusion of mCRP.

Figure 10A:
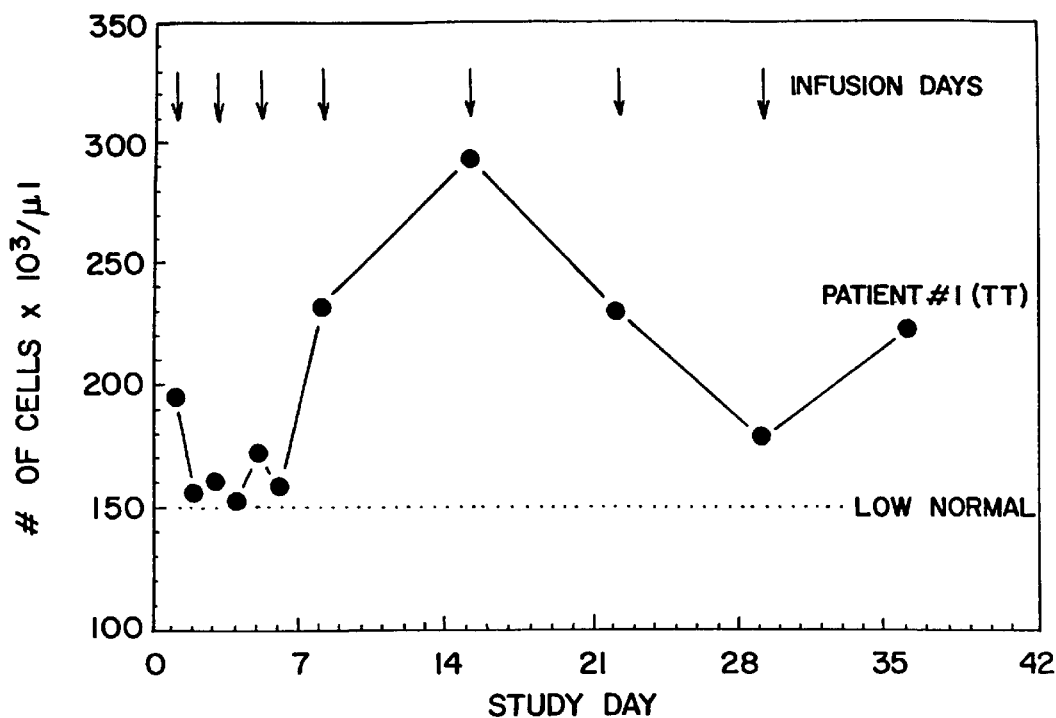
FIGS. 10A–10E are graphs showing the effect of mCRP on platelet counts in HIV-positive humans.
Figure 10B:
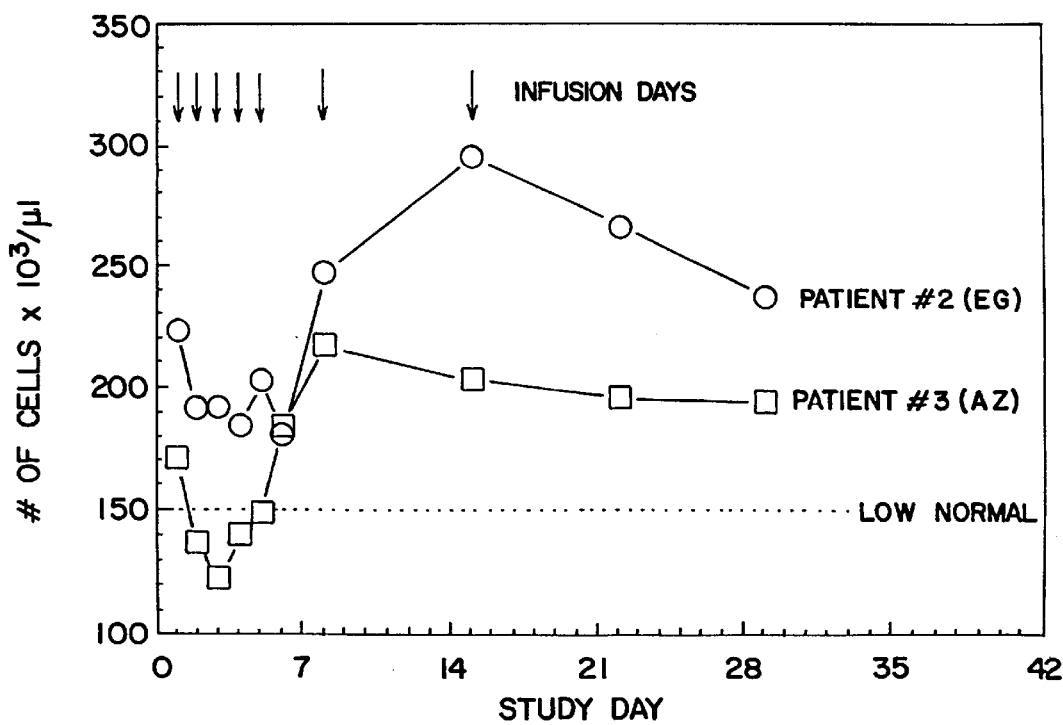
Figure 10C:
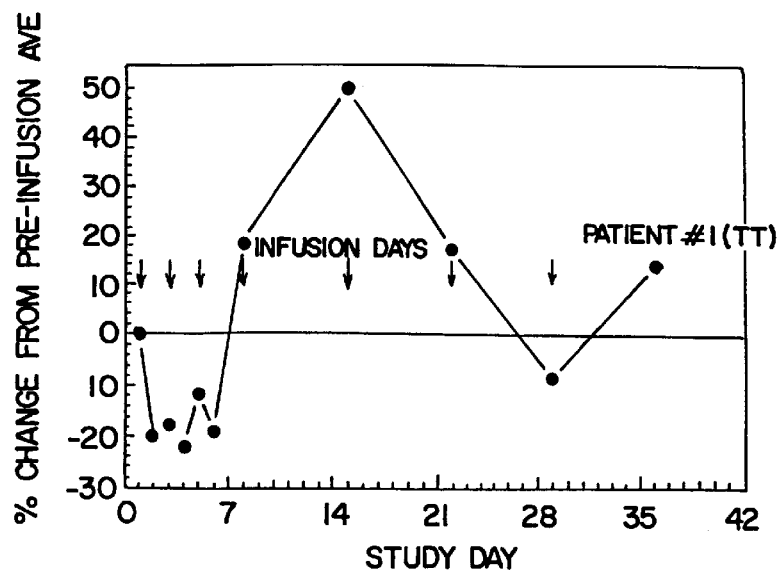
Figure 10D:
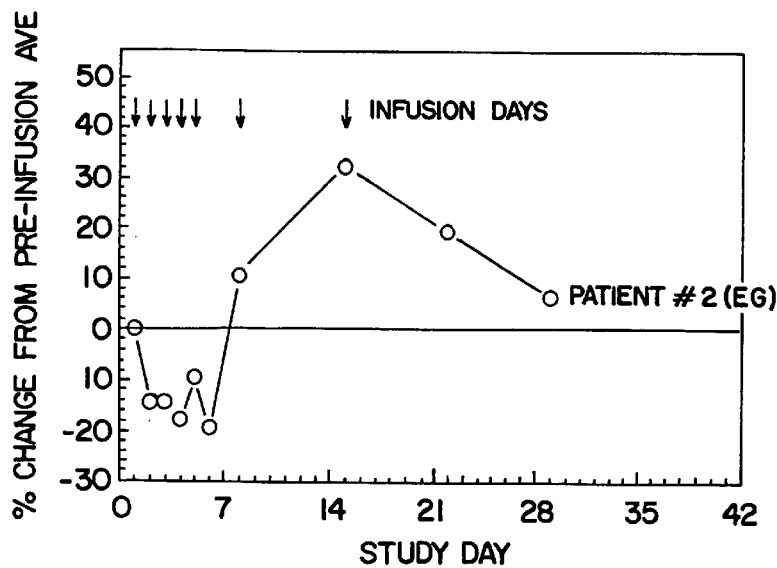
Figure 10E:
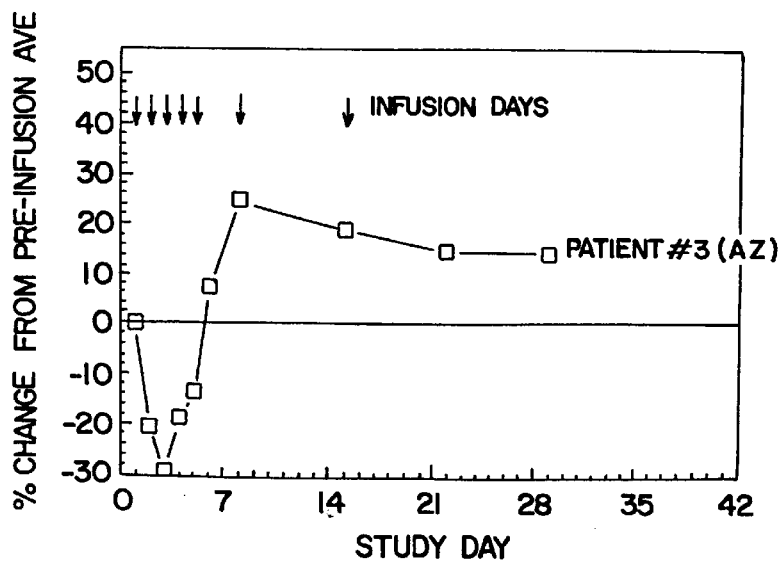

All three patients showed an increase in blood platelet levels after the period of intensive mCRP therapy. This increase persisted throughout the experimental period. All three patients showed an initial dip in blood platelet levels (approximately 20–30% drop) during the period of intensive mCRP therapy (days 2–6). (See FIGS. 10A and 10B). This drop was short lived, however, as a rapid increase was observed in all patients on day 8. All three patients showed from 25-to-50% increases in blood platelet counts compared to pre-infusion averages. (See FIGS. 10C–10E).

Figure 11A:
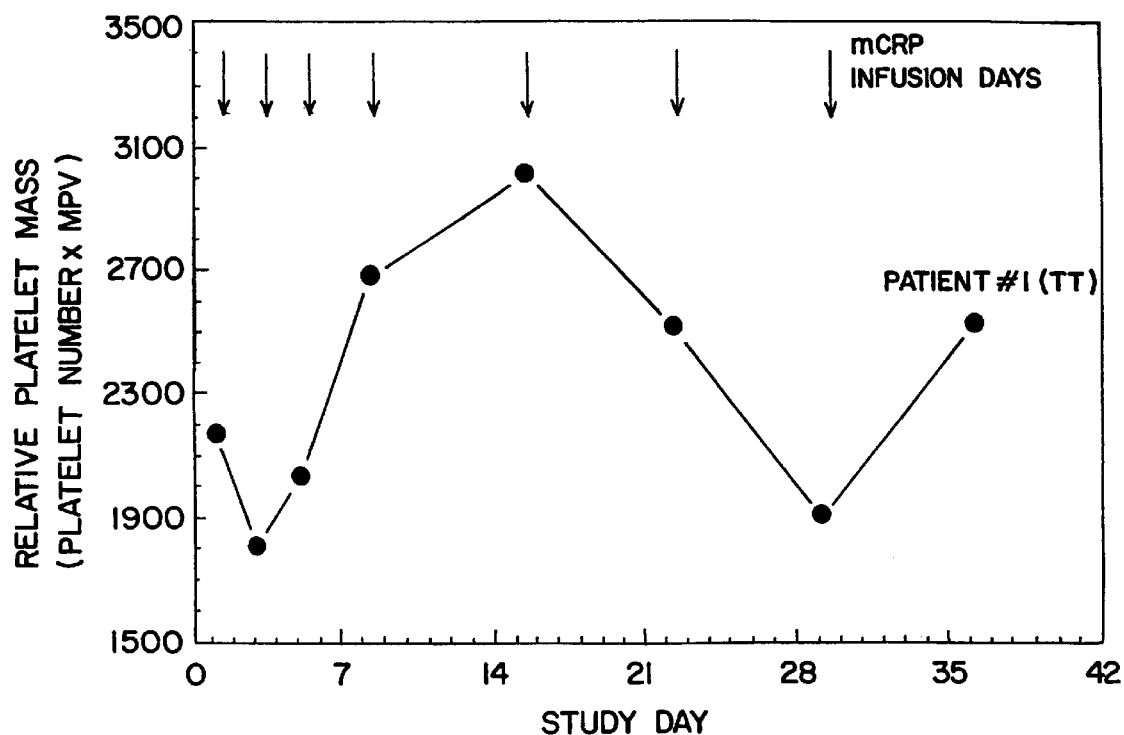
FIGS. 11A and 11B are graphs showing the effect of mCRP on platelet mass in HIV-positive humans.
Figure 11B:
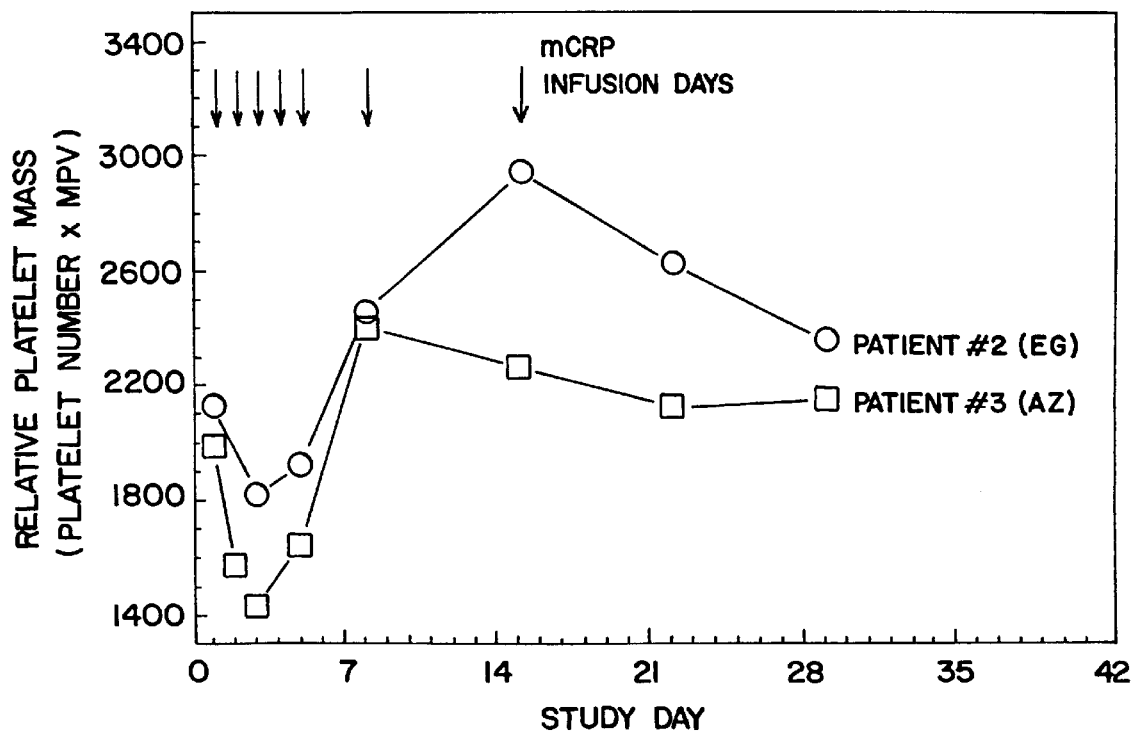

FIGS. 11A and 11B illustrate that the mCRP therapy increased platelet mass in all three HIV positive patients involved in the study. In the first 3-to-5 days of mCRP therapy, there was a slight decrease in blood platelet counts but no change, or increase in MPV (data not shown). Typically, it takes approximately 3 days for the process of megakaryocytopoiesis to occur. After 3–5 days of mCRP therapy, platelet mass increased 20–40% in these three patients.

The data suggests that early on (in the first 3–5 days of mCRP therapy), there is a slight decrease in blood platelet counts, and no change or increase in the mean platelet volume. After 3–5 days, the time it takes to stimulate megakaryocytes to produce more platelets, there is an increase in platelet number in the blood. These new platelets are of normal size, and are not smaller as would be expected. This suggests that mCRP may function like a Megakaryocyte-Potentiator factor, contributing not only to increase in platelet numbers, but to platelet mass as well.

Example 9
The Effect Of mCRP and Mutant rCRP On Human Bone Marrow Megakaryocytopoiesis Low-density non-adherent mononuclear cells were prepared from bone marrow from patients undergoing total hip arthroplasty. Briefly, a sample containing bits of bone and surgical debris was added to MEM-alpha Eagle Medium (Gibco) supplemented with heparin, EDTA and 5 $\mu$g/ml sterile DNase I (Boehringer Mannheim). The sample was gently shaken and incubated for 5 minutes at 0° C. The supernatant containing the bone marrow cells was collected, and the residual dense bone material was reextracted multiple times until the bone appeared white. All supernatants were pooled. Cell aggregates were broken up by passing the recovered cell suspension gently through an 18 guage needle.

The cell suspension was layered on top of an equal volume of 1.077 g/L Ficoll-Paque (Pharmacia) and the mixture was centrifuged using a swinging bucket rotor at 400×g for 30 minutes at ambient temperature. The white layer of cells which collected at the interface between the Ficoll-Paque and the medium is referred to as low-density mononuclear cells.

Cells were collected, suspended in IMBM medium (Difco) and were washed multiple times before being resuspended in a minimal volume of IMBM medium. Cells were then counted and were diluted to 1×10$^6$ cells/ml in IMBM medium supplemented with 10% Gold-Fetal Bovine Serum (ICN). The cells were then added to a plastic dish and were incubated for from 2 hours to overnight at 37° C. in a 5% $CO_2$ environment to remove adherent cells. The supernatant, which contains low density mononuclear cells (MNC's) was collected and washed in IMBM medium.

MNCs (4.5×10$^6$) were cultured in IMBM medium for 12 days at 37° C. in a 5% $CO_2$ environment supplemented with the various additives as indicated in Table 4 below. At 12 days, the cultures were characterized by enumeration and immunophenotypic analysis by flow cytometry performed at Northwestern Univeristy using a Coulter Flow cytometer. Megakaryocytes were identified using fluorescently-tagged anti-CD41a (a monoclonal antibody which recognizes gpIIb/IIIa; obtained from Becton Dickinson).

Solution mCRP (prepared as described in Example 1) was added to some of the cultures along with 1% or 10% fetal bovine serum (ICN). These experiments were designed to see if mCRP had Megakaryocyte-Stimulating Factor activity (Meg-CSF).

To assess the Megakaryocyte-Potentiation activity (Meg-POT) of mCRP and the mutant rCRP produced by pIT13 (preparation described in Example 2), aplastic serum or IL-3 (R & D Systems) was added to the cultures as the primary stimulus. Aplastic serum is the serum of patients with aplastic anemia. The rationale for adding this serum is that such patients have low levels of blood cells as part of their disease and they must, therefore, be making a lot of "hematopoietic growth factors" to try and compensate for the low level of cells. Thus, aplastic serum would be a source of naturally-occurring megakaryocyte stimulating factors. When used, aplastic serum (AS) was added at 1%, 2.5% or 10%.

The results of the experiments are summarized in Table 4. The results are expressed as:

1. total cell number at day 12 of culture (of $4.5 \times 10^6$ seeded);
2. relative frequency of small, intermediate and large CD41+ cells;
3. the absolute number of megakaryocytes quantified;
4. the number of megakaryocytes/number seeded cells; and
5. the % of cells remaining alive on day 12, and the % of cells alive on day 12 which are megakaryocytes.

When bone marrow cells were grown for 12 days in the presence of 20 μg/ml mCRP, only 7–27% of the starting cell number could be quantified as alive on day 12. The percentage of the total cell population which was quantified as megakaryocytes on day 12 varied from 0.11% to 0.35% (normal % megakaryocytes is approximately 0.5%). Hence, the addition of mCRP did not apparently keep the cells alive, nor did it selectively stimulate the growth of megakaryocytes.

By adding AS at 1%, approximately 50% of the starting cell number was quantified on day 12. There was a slight increase in the absolute number of CD41+ cells with AS alone. However, when the MNC's were cultured in the presence of AS and 20 μg/ml mCRP, the absolute number of CD41+ cells, the number of CD41+ cells/million seeded MNC cells, and the % of CD41+ cells/cells alive on day 12 all increased approximately two-fold. This suggests that mCRP augments the action of AS in terms of the development of human bone marrow cells into the megakaryocyte lineage.

When 2.5% AS was added, again, approximately 50% of the starting cell number was quantified as alive on day 12. The absolute number of CD41+ cells quantified in AS alone more than doubled (from 6,900 to 16,000), indicating that there was a factor in AS which promoted megakaryocyte growth. In just AS, the % of cells quantified on day 12 which were CD41+ increased from the control level of 0.3% to 0.77%.

When 20 μg/ml or 32 μg/ml mCRP was co-cultured with 2.5% AS, there was no apparent effect on the survival of the seeded MNCs, but there was an increase in quantified CD41+ cells above the 16,000 cells quantified in 2.5% AS alone. When cultured in the presence of mCRP, 23,000 to 27,000 CD41+ cells were quantified (5,100 to 6,000 cells/million seeded MNCs). This represents a 44–69% increase over AS alone. The % of cells alive on day 12 also increased such that 1% to 1.5% of the total cells quantified were now CD41+ cells.

When mutant rCRP was used in place of mCRP, fewer cells were found alive on day 12 (declining from 40–50% of seeded MNCs found alive on day 12 to 29–33% of seeded MNCs). However, of these cells, from 23,000 to 28,000 CD41+ cells were quantified (5,100 to 6,200 cells/million seeded MNCs), representing from 1.77 to 1.9% of the cells alive on day 12. This data suggests mCRP and the mutant rCRP enhance the survival and growth of human bone marrow non-adherent mononuclear cells in culture. They also suggest that mCRP and mutant rCRP function best as potentiators, rather than as primary stimuli, of megakaryocyte growth.

When the MNCs were grown in 10% AS, 78% of the starting cells number was quantified on day 12. The number of CD41+ cells increased to 116,000 (25,700/million MNCs seeded on day 1). This represents 3.3% of those cells still alive on day 12.

When mutant rCRP was co-cultured with MNCs in the presence of 10% AS, the number of cells quantified as alive on day 12 increased to 5.1 million, increasing 13% above the starting number of cells seeded. This suggests that mutant rCRP promoted cell growth during the 12 days in culture. The number of CD41+ cells quantified increased to 143,000 (31,700/million cells seeded; an increase of 23% over 10% AS alone). CD41+ cells accounted for 2.8% of total cells alive.

When IL-3 was used as the primary stimulus instead of AS, the number of cells alive on day 12 increased from 2.8 million (IL-3 alone; 62.2% of the starting cell number) to 3.9 million (IL-3 plus mCRP; 84.8% of the starting cell number). The absolute numbers of CD41+ cells increased 19.4%–21.2% in the presence of mCRP compared to IL-3 alone (from 98,000 to 117,000 in experiment #1 and from 23,100 to 28,000 in experiment #2). The mutant rCRP also caused an increase in the number of CD41+ cells quantified in this co-culture (from 23,100 to 28,000).

Modified-CRP and mutant rCRP appear to have megakaryocyte stimulating activity in human bone marrow cultures. The effect of mCRP and mutant rCRP appears to be most apparent when used in combination with a primary stimulus of megakaryocyte growth (aplastic serum or IL-3). In some experiments mCRP and mutant rCRP appeared to enhance a general growth of the mononuclear cell population, with a particular effect on megakaryocytes (i.e. CD41+ cells).

TABLE 4

Effect of mCRP on Human Bone Marrow Megakaryocyte Cell Growth

| Treatment | # of cells alive of day 12 | % surviving cells | Absolute # CD41 + cells | # CD41 + cells/$10^6$ seeded MNC | % CD41 + cells/# cells alive on day 12 |
|---|---|---|---|---|---|
| None | $0.7 \times 10^6$ | 15.6 | 2,450 | 544 | 0.35 |
| + 20 μg/ml sol-mCRP | $0.3 \times 10^6$ | 6.7 | 1,500 | 333 | 0.11 |
| 1% Fetal Bovine Serum | $0.9 \times 10^6$ | 20 | 4,500 | 1,000 | 0.11 |
| + 20 μg/ml sol-mCRP | $0.8 \times 10^6$ | 17.8 | 4,800 | 1,067 | 0.11 |
| 10% Fetal Bovine Serum | $1.0 \times 10^6$ | 22.2 | 5,500 | 1,222 | 0.12 |
| + 20 μg/ml sol-mCRP | $1.2 \times 10^6$ | 26.7 | 6,600 | 1,467 | 0.12 |
| 1% Aplastic Serum | $2.3 \times 10^6$ | 51.1 | 6,900 | 1,533 | 0.3 |
| + 20 μg/ml sol-mCRP | $2.0 \times 10^6$ | 44.4 | 12,000 | 2,667 | 0.6 |
| 2.5% Aplastic Serum | $2.09 \times 10^6$ | 46.4 | 16,000 | 3,560 | 0.77 |
| + 20 μg/ml sol-mCRP | $1.8 \times 10^6$ | 40 | 27,000 | 6,000 | 1.5 |
| + 32 μg/ml sol-mCRP | $2.3 \times 10^6$ | 51.1 | 23,000 | 5,100 | 1 |
| + 20 μg/ml rCRP | $1.5 \times 10^6$ | 33.3 | 28,000 | 6,200 | 1.9 |
| + 32 μg/ml rCRP | $1.3 \times 10^6$ | 28.9 | 23,000 | 5,100 | 1.77 |
| 10% Aplastic Serum | $3.5 \times 10^6$ | 77.8 | 116,000 | 25,700 | 3.3 |
| + 32 μg/ml rCRP | $5.1 \times 10^6$ | 113 | 143,000 | 31,700 | 2.8 |
| IL-3 (50 U/ml) (exp #1) | $2.8 \times 10^6$ | 62.2 | 98,000 | 21,778 | 0.48 |
| + 20 μg/ml sol-mCRP | $3.9 \times 10^6$ | 86.7 | 117,000 | 26,000 | 0.67 |
| IL-3 (50 U/ml) (exp #2) | $2.1 \times 10^6$ | 46.7 | 23,100 | 5,133 | 0.24 |
| + 20 μg/ml sol-mCRP | $1.9 \times 10^6$ | 42.2 | 9,500 | 2,111 | 0.11 |
| + 32 μg/ml sol-mCRP | $2.0 \times 10^6$ | 44.4 | 28,000 | 6,222 | 0.31 |
| + 32 μg/ml rCRP | $2.0 \times 10^6$ | 44.4 | 28,000 | 6,222 | 0.31 |

$4.5 \times 10^6$ human bone marrow non-adherent mononuclear cells seeded on day 1

Example 10
Testing of Mutant rCRP In Mice

Three experiments were performed. In all three experiments, groups of five female BALB/c mice (Harlan-Sprague-Dawley) were used.

A. Experiment 1

In the first, the mice were injected intravenously with the mutant rCRP produced by pIT13 (preparation described in Example 2), Monday through Friday for two consecutive weeks. The mutant rCRP was injected at 1 mg/kg/dose, 3 mg/kg/dose or 10 mg/kg/dose. Blood samples were drawn on days 1 (just before the first injection), 4, 8, 11, 15, 18 and 23. Platelet counts were quantified using a Sysmex F-800 cell counter (Toa Medical Electronics, Japan).

Figure 17A:
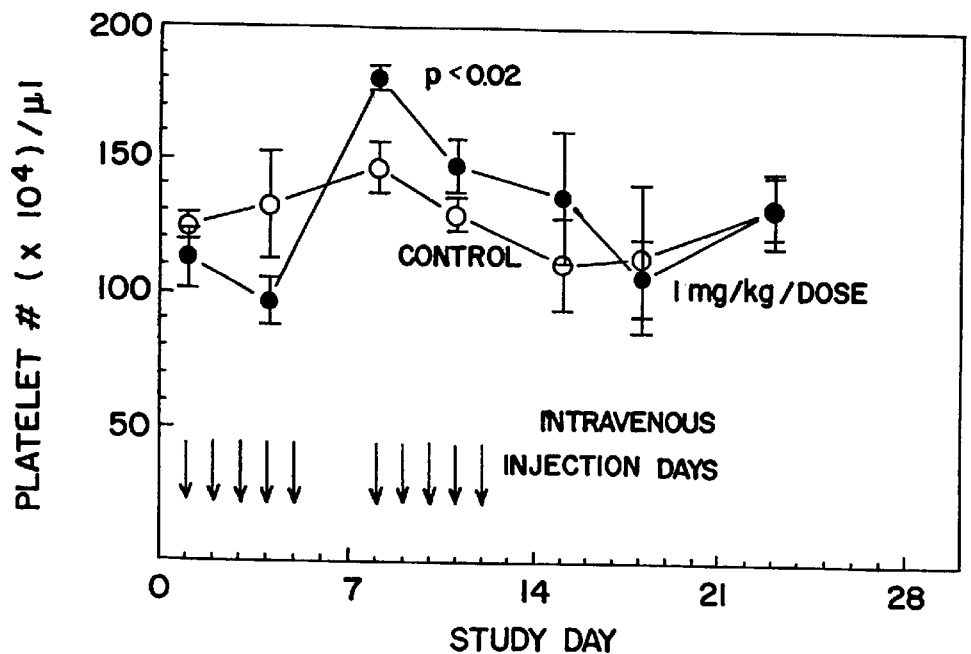
FIGS. 17A–C are graphs showing the effects of mutant rCRP produced by pIT13 on murine thrombopoiesis.
Figure 17B:
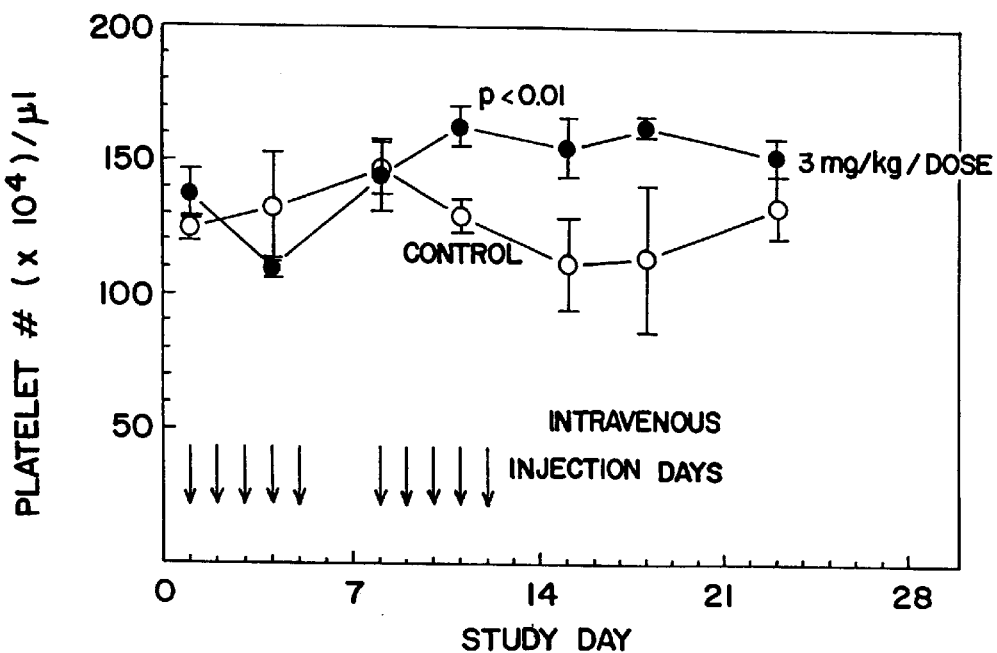
Figure 17C:
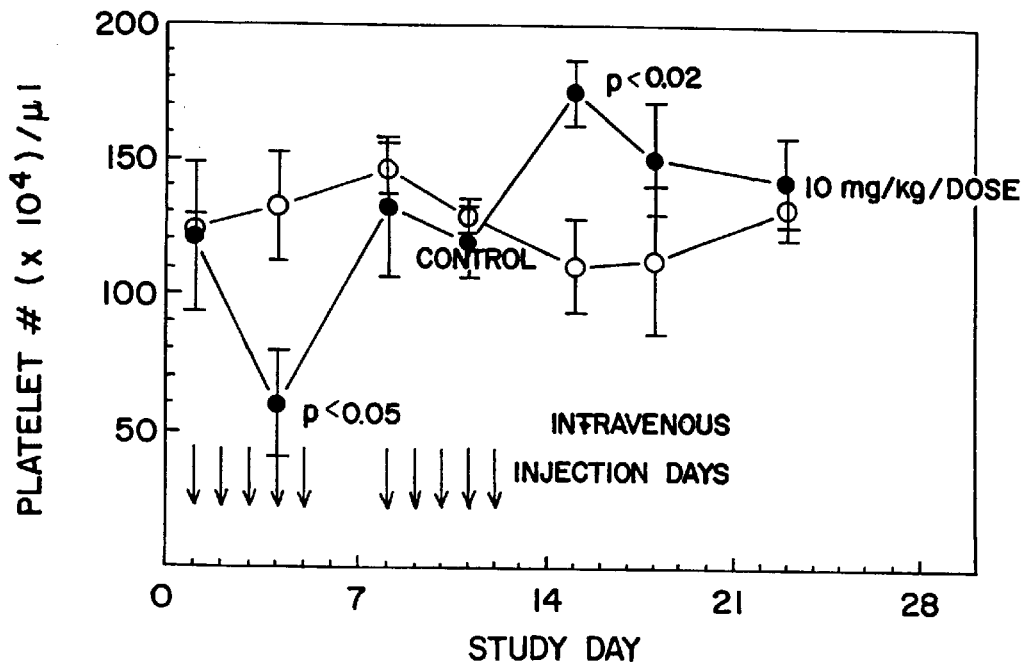

FIGS. 17A–C illustrate the results of this experiment. All three doses of intravenously injected mutant rCRP caused a transient thrombocytopoenia which was noted on day 4. The platelet drop on this day was found to be significantly different in mice treated with the highest dose (10 mg/kg/dose) of mutant rCRP compared to the mean platelet level noted in animals receiving buffer control (FIG. 1C; p<0.05). The mean platelet levels on all subsequent sample days in all mutant rCRP dose groups then increased to or above the mean platelet level of the control group of animals on each study day. Statistically significant increases were noted in all three dose groups. Of note, the 1 mg/kg/dose group of animals showed statistical significance over control on study day 8 (FIG. 17A), the 3 mg/kg/dose group of animals showed statistical significance over control on study day 12 (FIG. 17B), and the 10 mg/kg/dose group of animals showed statistical significance over control on study day 15 (FIG. 17C). Data are plotted as mean±standard error. Only p values of ≦0.05 are considered statistically significant.

B. Experiment 2

In the second experiment, mutant rCRP produced by pIT13 was injected subcutaneously instead of intravenously in the same amounts and over the same time frame as in experiment 1. Blood samples were drawn on days 1, 4, 8, 16, 20 and 24. Platelet counts were quantified using a Sysmex F-800 cell counter.

Figure 18A:
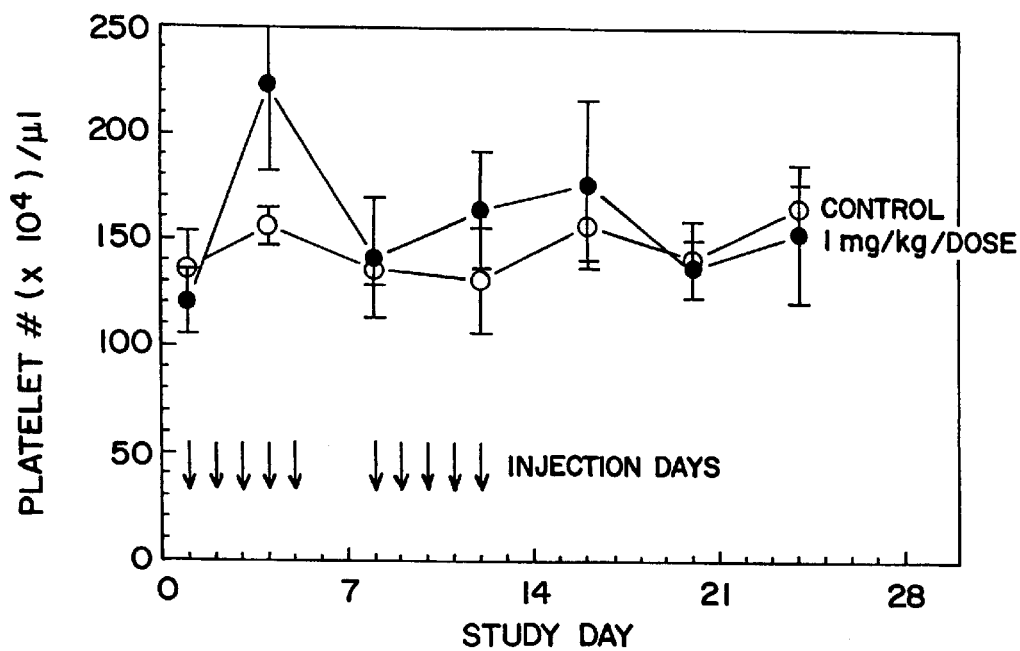
FIGS. 18A–C are graphs showing the effects of mutant rCRP produced by pIT13 on murine thrombopoiesis.
Figure 18B:
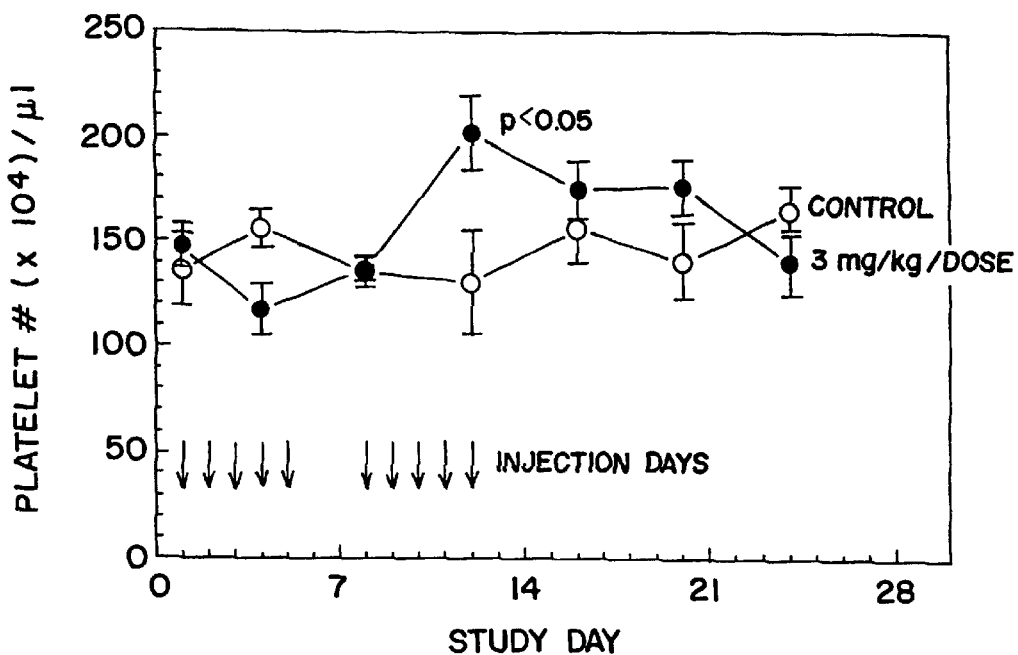
Figure 18C:
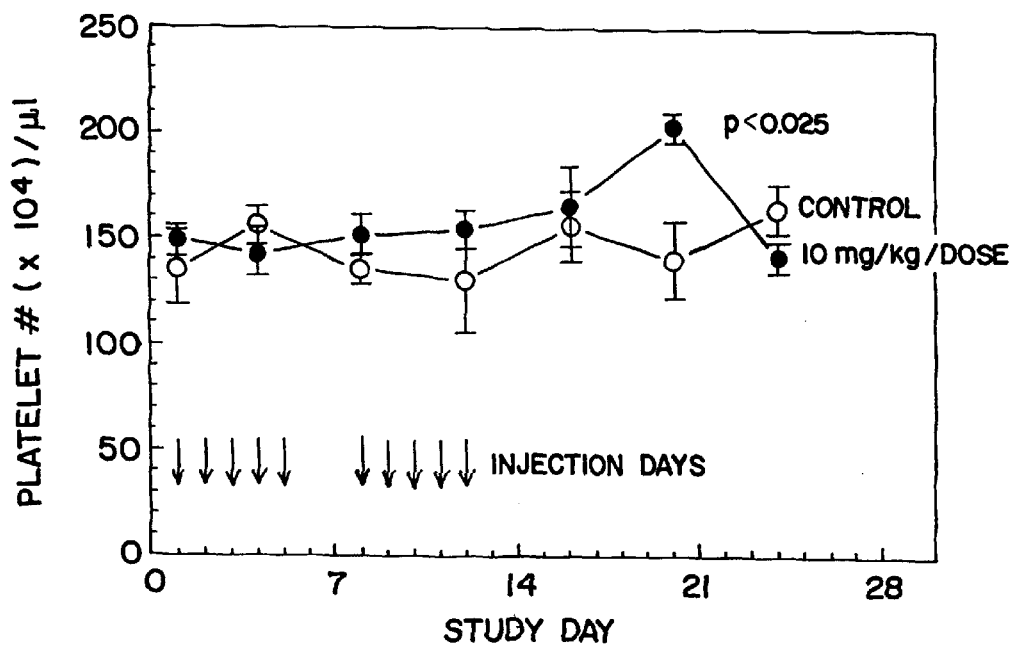

FIGS. 18A–C illustrate the results of this experiment. The thrombocytopoenia noted in experiment 1 was not apparent using the subcutaneous route of injection, and increases in peripheral blood platelet levels were again observed in all three dose groups during the experiment and within 8 days after the last injection. The same trend of statistically significant increases seen in the first experiment was noted in the second experiment, again being correlated with increasing mutant rCRP dose amounts. That is, the 1 mg/kg/dose group of animals showed a statistically significant increase over the control mean on study day 4 (FIG. 18A), the 3 mg/kg/dose group of animals showed a statistically significant increase over the control mean on study day 12 (FIG. 18B), and the 10 mg/kg/dose group of animals showed a statistically significant increase over the control mean on study day 20 (FIG. 18C).

C. Experiment 3

In the third experiment, the effect of multiple injections of mutant rCRP produced by pIT13 at the 3 mg/kg/dose level was compared to the effect of a similarly administered amount of the solution mCRP. Subcutaneous injections were performed done on days 1 through 4, and 8 through 16. Blood samples were drawn and analyzed for platelet counts on days 1, 4, 8, 12, 16, 20 and 24.

Figure 19:
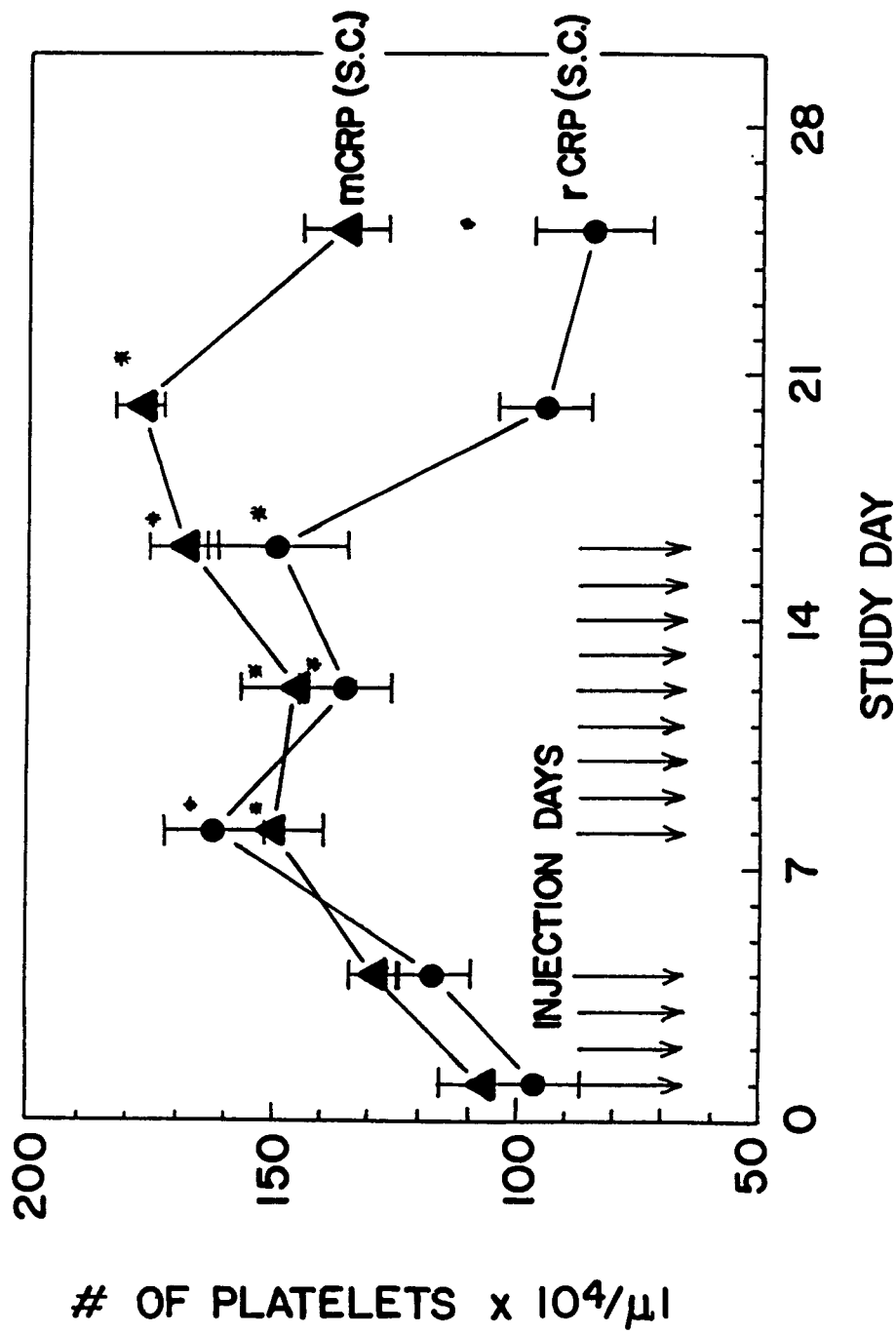
FIG. 19 is a graph showing the effects of mCRP and mutant rCRP produced by pIT13 on murine thrombopoiesis.

FIG. 19 shows that the effect of multiple subcutaneous injections of mutant rCRP and mCRP on increasing peripheral blood platelet counts in mice are similar. Platelet counts for both mutant rCRP and mCRP on study days 8, 12 and 16 (i.e., days on which injections were given) were statistically elevated to p values at least <0.02 (indicated by *), over the day 1 mean platelet counts in each group of animals. The increased platelet count persisted in mCRP-treated animals on day 20 (four days after the last injection). In both mutant rCRP-treated and mCRP-treated animals, the peripheral blood platelet values eventually dropped toward pre-injection levels after therapy was stopped.

What is claimed is:

1. An article of manufacture comprising:
   a container;
   a label on the container; and
   a composition contained within the container;
   wherein:
   the composition is effective for stimulating thrombocytopoiesis or megakaryocytopoiesis,
   the label on the container indicates that the composition is useful for stimulating thrombocytopoiesis or megakaryocytopoiesis, and
   the active agent in the composition comprises mutant rCRP expressing neo-CRP antigenicity, wherein the mutant rCRP has an amino acid sequence which is identical to an amino acid sequence of an unmutated CRP, except for four changes: 1) the N-terminal PCA amino acid of the unmutated CRP is preceded by a formylated-methionine; 2) the N-terminal PCA amino acid of the unmutated CRP has been changed to glutamine; 3) cysteine residue number 36 has been replaced by an alanine residue; and 4) cysteine residue number 97 has been replaced by an alanine residue.

2. The article of manufacture of claim 1 wherein the label on the container further indicates directions for in vitro or in vivo use of said composition.

3. A kit comprising:
   (1) a first container, a label on the first container, and a composition contained within the first container, wherein:
   the composition is effective for stimulating thrombocytopoiesis or megakaryocytopoiesis,
   the label on the first container indicates that the composition is useful for stimulating thrombocytopoiesis or megakaryocytopoiesis, and
   the active agent in the composition comprises mutant rCRP expressing neo-CRP antigenicity, wherein the mutant rCRP has an amino acid sequence which is identical to an amino acid sequence of an unmutated CRP, except for four changes: 1) the N-terminal PCA amino acid of the unmutated CRP is preceded by a formylated-methionine; 2) the N-terminal PCA amino acid of the unmutated CRP has been changed to glutamine; 3) cysteine residue number 36 has been replaced by an alanine residue; and 4) cysteine residue number 97 has been replaced by an alanine residue; and
   (2) a second container containing an isotonic buffer.

* * * * *